US009492500B2

(12) United States Patent
Call et al.

(10) Patent No.: US 9,492,500 B2
(45) Date of Patent: Nov. 15, 2016

(54) MICROCIN AND USES THEREOF

(71) Applicant: WASHINGTON STATE UNIVERSITY, Pullman, WA (US)

(72) Inventors: Douglas R. Call, Pullman, WA (US); Lauren Eberhart, Pullman, WA (US); Kelly A. Brayton, Pullman, WA (US); Thomas E. Besser, Pullman, WA (US); Ashish Sawant, Pullman, WA (US); Lisa Orfe, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 14/407,975

(22) PCT Filed: Jun. 14, 2013

(86) PCT No.: PCT/US2013/045937
§ 371 (c)(1),
(2) Date: Dec. 15, 2014

(87) PCT Pub. No.: WO2013/188794
PCT Pub. Date: Dec. 19, 2013

(65) Prior Publication Data

US 2015/0164983 A1 Jun. 18, 2015

Related U.S. Application Data

(60) Provisional application No. 61/660,616, filed on Jun. 15, 2012.

(51) Int. Cl.

| | |
|---|---|
| ***C12N 1/12*** | (2006.01) |
| ***C12N 1/20*** | (2006.01) |
| ***A61K 38/16*** | (2006.01) |
| ***C07K 14/245*** | (2006.01) |
| ***A01N 63/00*** | (2006.01) |
| ***A01N 63/02*** | (2006.01) |
| ***A61K 35/74*** | (2015.01) |
| ***C11D 3/38*** | (2006.01) |
| ***C12N 7/00*** | (2006.01) |

(52) U.S. Cl.
CPC ............. *A61K 38/164* (2013.01); *A01N 63/00* (2013.01); *A01N 63/02* (2013.01); *A61K 35/74* (2013.01); *C07K 14/245* (2013.01); *C11D 3/381* (2013.01); *C12N 7/00* (2013.01); *C12N 2710/10021* (2013.01); *C12N 2710/14021* (2013.01)

(58) Field of Classification Search
CPC .................................................... A61K 38/164
See application file for complete search history.

(56) References Cited

U.S. PATENT DOCUMENTS 5,512,282 A * 4/1996 Krivan ............... C07K 16/1232 424/164.1

OTHER PUBLICATIONS

Ashkenazi et al (Therapeutic Advances in Vaccines vol. 1 (3) pp. 113-123, 2013).*
Plotkin et al (Vacciines WB Saunders Company, p. 571, 1988).*

* cited by examiner

*Primary Examiner* — Albert Navarro
(74) *Attorney, Agent, or Firm* — Whitman, Curtis & Cook, P.C.

(57) ABSTRACT

Microcin MccPDI and bacteria harboring the mcpM gene which encodes MccPDI, limit growth of and/or kill pathogenic bacteria such as pathogenic *Escherichia coli* (*E. coli*) and/or *Shigella* bacteria via proximity-dependent inhibition (PDI).

8 Claims, 9 Drawing Sheets

MICROCIN AND USES THEREOF

ACKNOWLEDGEMENT OF FEDERAL FUNDING

Particular aspects of the present invention were, at least in part, supported by Grant Number 2010-04487 from the United States Department of Agriculture (USDA-AFRI-NIFA), and the United States government therefore has certain rights in the invention.

FIELD OF THE INVENTION

Aspects of the invention relate generally to bacteria, bacteriocins (e.g., colicins or microcins) and proximity-dependent inhibition (PDI), and in more particular embodiments to compositions and methods for controlling and/or killing pathogenic bacteria (e.g., enterohemorrhagic and/or enterotoxigenic strains of *E. coli*), comprising use of a novel microcin.

BACKGROUND

*Escherichia coli* are commonly found in the gut of both humans and animals. Most *E. coli* are considered symbiotic; however, pathogenic strains have been isolated that are associated with foodborne illness in people and animals e.g., pathogenic *E. coli* K88 and K99 affect swine and calves, respectively. Transmission of pathogenic *E. coli* occurs through fecal contamination of food or water, and is commonly associated with the consumption of under-cooked meat, raw milk, or contaminated vegetables.

Pathogenic *E. coli* includes the Shiga-toxin producing strains known as STEC. Shiga-toxin is named for its resemblance to the Shiga-toxin produced by *Shigella dysenteriae*. STEC infection can be asymptomatic, or include symptoms of fever, watery diarrhea, severe abdominal pain, hemolytic uremic syndrome (HUS) and even death, with more severe cases typically being reported in young children or the elderly. Enterohaemorrhagic *E. coli* (EHEC) are a subset of STEC, characterized by their ability to form attaching and effacing intestinal lesions. Cattle are the main reservoir for EHEC, the bacteria living asymptomatically in the cow intestine, although these bacteria have also been isolated from the intestinal tract of other domestic animals including sheep, pigs, goats, and dogs. These EHEC predominantly colonize the recto-anal junction of cattle, thereby increasing the risk of transmission to humans through fecal contamination. Numerous EHEC have been isolated including serotypes O111, O145, O103, O26, and O157. According to the Centers for Disease Control and Prevention, O157:H7 is the most common serotype that causing *E. coli*-linked food poisoning in the United States. The infectious dose is estimated to be as low as 10-100 bacteria. Currently, no treatment is available for EHEC infections. Furthermore, antibiotic treatment can worsen symptoms of an EHEC infection by inducing shiga-toxin production and increasing the risk of HUS.

The introduction of antibiotics as therapeutics in the mid-1940s was an important advancement for medicine in terms of reducing human morbidity and mortality. However, the subsequent emergence of antibiotic resistant bacteria indicates that bacteria adapt to antibiotic pressure. Resistance can be acquired and maintained within a population through horizontal transfer of resistant genes, and/or through selection for mutations that confer resistance. Unfortunately, the use of antibiotics is widespread and invariably selects for resistance as continual exposure to the drugs inhibit susceptible strains and allows resistant strains to emerge and dominate a population. Selection for resistance occurs for all bacteria exposed to antibiotics, not just the specific pathogens that are being targeted. Such as, when enrofloxacin was used to treat *E. coli* infections in poultry, it simultaneously selected for resistance in *Campylobacter jejuni*. The increasing prevalence of resistant bacterial pathogens threatens the effectiveness of currently available antibiotics and presents a difficult challenge in human and animal medicine. The development of novel strategies to control pathogenic bacteria is necessary to 1) combat infection by existing strains and 2) provide alternatives so that antibiotic use, and hence the emergence of resistant strains, can be decreased.

Some bacteria have developed the ability to inhibit other bacteria, and further characterization of how this occurs could be helpful in the design of new anti-bacterial strategies. For example, cell-cell inhibition mechanisms have been documented in the literature and range from contact-dependent inhibition (1, 20) to production of narrow-spectrum antimicrobial proteins called bacteriocins. Bacteriocins typically restrict the growth of closely related bacteria (reviewed in (28, 31)). *E. coli* produce numerous bacteriocins (31), classified as either colicins or microcins (2, 11). Colicins are high-molecular weight, whereas microcins are typically <10 kDa. Microcins can be either chromosomally or plasmid encoded, whereas colicins have only been found on plasmids (13, 29, 30). Colicin production is usually correlated with an SOS response to stress (22, 34) and release of the colicin typically occurs through cell lysis. Microcins are secreted from intact cells (8, 27). Bacteriocins have been identified that kill competitors through pore formation, nuclease activity, or by inhibiting protein synthesis (3, 23-25).

Sawant et al. recently described a novel bacterial inhibition phenotype whereby defined strains of *Escherichia coli* from cattle are able to inhibit growth of other *E. coli* strains including several strains of enterohemorrhagic *E. coli* (EHEC) and enterotoxigenic *E. coli* (ETEC) (32). During in vitro competition assays, susceptible strains declined an average 4-6 log in population size relative to their expected population density when grown as monocultures. The inhibition phenotype was called "proximity-dependent inhibition" (PDI) because of the apparent need for inhibitor and susceptible strains to be located in close physical proximity for the phenotype to be observed. Two different *E. coli* strains were described as expressing this trait (PDI$^+$); multidrug resistant *E. coli*-25 and antibiotic susceptible *E. coli*-264. *E. coli*-25 and *E. coli*-264 do not affect the growth of each other, indicating that immunity is either conferred actively through the presence of an immunity mechanism, or passively through the absence of a receptor ligand found on susceptible cells.

Certain characteristics of the PDI phenotype resemble that of microcin production. For example, inhibition is effective against closely related species; PDI is not dependent on an SOS response; and production presumably does not kill the inhibitor strain (32). Nevertheless, microcins are soluble proteins and when Sawant et al. (32) employed a split-well experiment they demonstrated that close cell-cell proximity is required for the PDI phenotype to function. These findings suggest that the inhibition mechanism is not due to a soluble molecule unless the concentration is so low as to require close proximity to be effective (32).

The initial report of PDI provided a detailed description of the phenotype and a similar phenotype has been described between *Bibersteinia trehalosi* and *Mannheimia haemo-*

*lytica* (4). Nevertheless, the exact mechanism of PDI and requisite genes for inhibition and immunity at the time that the PDI was originally described. Progress in this field could aid the development of strategies to combat the emergence and spread of pathogenic bacteria, and to provide treatments for infection with pathogenic bacteria.

SUMMARY OF EXEMPLARY ASPECTS

Particular embodiments of the invention demonstrate, for the first time, that "proximity-dependent inhibition" (hereinafter "PDI") results in death of the susceptible cells, and that PDI can be used for killing pathogenic *E. coli* in vitro on surfaces and materials of interest, and in vivo, and further the PDI can be used prophylactically and therapeutically.

Additional embodiments of the invention identify the PDI gene cluster, which resembles that of a class IIa microcin. The gene cluster includes ORFs putatively encoding proteins for microcin synthesis, immunity, and export. In addition, tolC is required for inhibition, thereby confirming that the microcin is secreted by a type I secretion system (T1SS).

According to further embodiments of the invention, the PDI phenotype is caused by a novel microcin, designated herein as MccPDI, and MccPDI is utilized in a number of different and beneficial applications. In some instances, the use of MccPDI and/or bacteria that produce MccPDI advantageously replaces the use of antibiotics.

Every strain from a genetically diverse panel of *E. coli* O157:H7 (n=25) and additional strains of *E. coli* serovar O26 were susceptible to the PDI phenotype. Live-dead staining was consistent with inhibition by killing of susceptible cells. Comparative genome analysis identified the genetic component of PDI, which is composed of a plasmid-borne (IncI1) operon encoding a putative microcin and associated genes for transport, immunity, and microcin activation. Transfer of the plasmid to a PDI' strain resulted in transfer of the phenotype and deletion of the genes within the operon resulted in loss of the inhibition phenotype. Deletion of chromosomally encoded tolC also resulted in loss of the inhibitory phenotype and this confirmed that the putative microcin is most likely secreted via a type I secretion pathway. Deletion of an unrelated plasmid gene had no effect on the PDI phenotype. Quantitative RT-PCR demonstrated that microcin expression is correlated with logarithmic-phase growth.

According to yet further embodiments of the invention, the ability to inhibit a diversity of *E. coli* strains indicates that this microcin has utility to influence gut community composition, and substantial utility for control of important enteric pathogens.

In some aspects, the bacteria that are killed (lysed, inhibited, damaged, etc.) are any that have (carry, bear, include, contain, etc.) the ompF protein in or as a component of their outer membrane. OmpF or "outer membrane protein F", (or OmpF porin), is an integral membrane protein located in the outer membrane of *E. coli* bacteria. OmpF porin is found in a trimer formation and is a non-specific transport channel that allows for the passive diffusion of small, polar molecules (600-700 Da in size) through the cell's outer membrane, e.g. water, ions, glucose, and other nutrients as well as waste products. Without being bound by theory, the microcin described herein appears to bind to OmpF when exerting its lethal effects.

DETAILED DESCRIPTION

Figure 1:
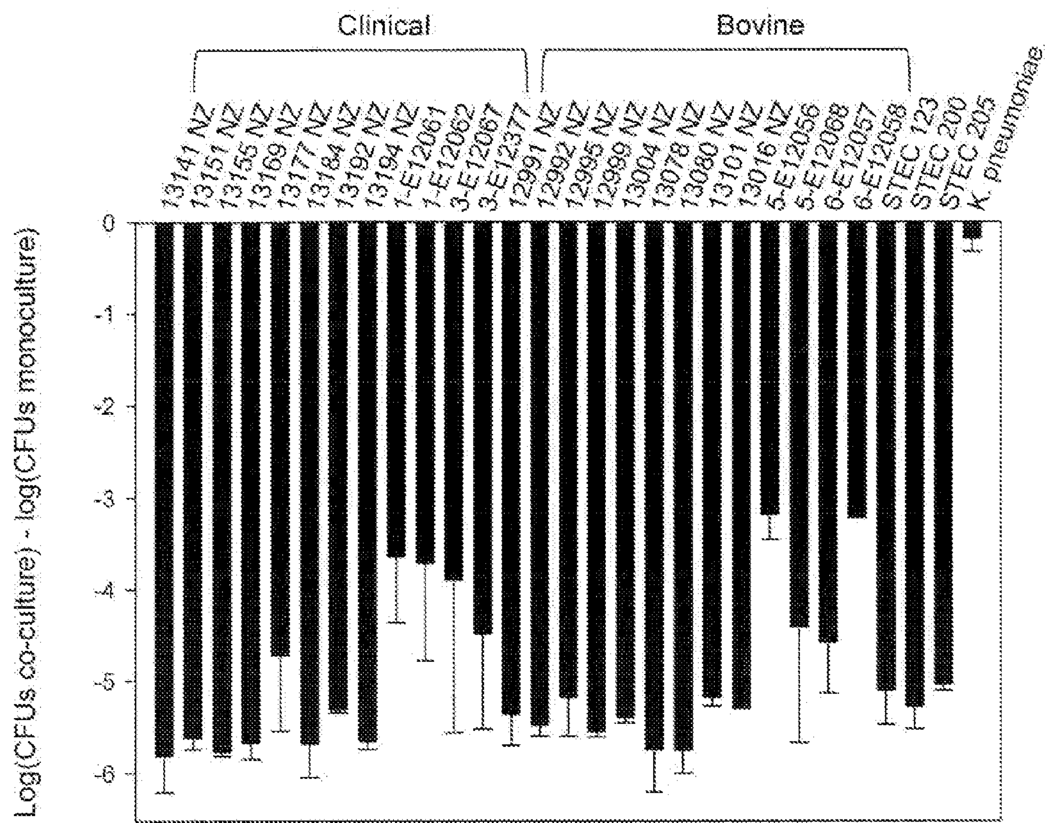
FIG. 1. PDI is effective against a broad panel of O157:H7 and STEC O26 *E. coli* isolates. On average, susceptible populations were reduced greater than 5-logs following 24 h co-culture with *E. coli*-25. Clinical and bovine-biased O157 genotypes are indicated (33). *Klebsiella pneumonia* was not inhibited by PDI and is included as a negative control. Error bars correspond to the standard error of the mean based on duplicate experiments.

The genetic components that are responsible for the PDI phenotype observed from *E. coli*-25 and *E. coli*-264 are, for the first time, identified herein. This 4.8-kb operon is present on pPDI (see Example 10 below) and is comprised of the genes mcpM, mcpI, mcpA, mcpD, and mcpB (see Example 9 below).

According to particular aspects, inhibition is mediated by the microcin encoded by mcpM, whose mature gene product is designated herein as MccPDI. A DNA probe designed from the sequence of the mcpA gene hybridized to a ~100 kb plasmid in both inhibitor strains. Plasmid DNA from the susceptible non-inhibitor strains, *E. coli*-6 and *E. coli*-82, did not hybridize to the mcpA-specific probe. pPDI was subsequently marked with a kanamycin resistant cassette (ΔtraM) and transferred to the PDI$^-$ strain, *E. coli*-4. Wild-type *E. coli*-4 does not exhibit the inhibitory phenotype, as indicated by competition assays with the susceptible *E. coli*-186 (Table 2; and see Example 6 herein below). *E. coli*-4 also exhibits susceptibility to PDI, based on CFU counts following co-culture with PDI$^+$ *E. coli*-264. Following transformation with pPDIΔtraM, *E. coli*-4 acquired the inhibitory phenotype and immunity (Table 2; and see Example 6). Together these results indicate PDI and self-immunity are encoded by the 98.8 kb plasmid (see Example 10 below).

To demonstrate the necessity for each gene in the operon for PDI function, genetic knockouts were constructed and used herein to show that disrupting any gene within the PDI operon blocked the inhibitory phenotype and, additionally, immunity to PDI was lost in the mcpM and mcpI mutants (FIG. 3). According to particular aspects, this indicated that all the genes were important for PDI, but immunity was dependent on only one or two genes. Due to the direct downstream location of mcpI, loss of immunity in the mcpM mutant was likely caused by a polar effect from ΔmcpM. This is consistent with the ability shown herein to complement immunity by the expression of mcpI alone. Although mcpI likely does not play a direct role in killing, it is necessary for self-immunity and for this reason is required for PDI. Deleting traM, a gene located ~20 Kb upstream of the PDI operon, did not affect either inhibition or immunity indicating that the methods used herein did not interfere with PDI. Furthermore, the tolC, mcpB, and mcpD mutants lost the ability to inhibit but retained immunity, consistent with a role in toxin transport.

According to particular aspects, and based on gene cluster and sequence analysis, MccPDI is best characterized as a Gram-negative class IIa microcin. The PDI gene cluster is relatively simple, consisting of two genes for export, one for immunity, one presumptively for microcin activation, and the microcin gene itself. Unlike class I and IIb microcins, which have several genes for post-translational modification, MccPDI only has one recognizable gene that is putatively required for microcin activation. The dedicated transport system involves the products of two plasmid-encoded genes, mcpB and mcpD. These two PDI genes have homology with hlyB and hlyD) of the *E. coli* α-hemolysin T1SS (9). This multicomponent export system has similar organization to transport systems for other class II microcins, including MccE492, MccL, and MccV (10, 18, 26). McpB contains the transmembrane domains and nucleotide-binding domains, including the highly conserved Walker A and B motifs and ABC signature, characteristic of the ABC-transporter superfamily of proteins (21). McpD is thought to act as a membrane fusion protein, forming a channel through the periplasm and connecting to the outer membrane protein TolC, the third component of class I microcin export machinery (7, 10, 18, 26). In total, these proteins form the export system allowing secretion of protein from the cytoplasm across the periplasmic space and into the extracellular medium. McpM has homology to other microcin precursors within the N-terminal sequence, which encodes a putative signal peptide (6) that is consistent with T1SS transport. The presence of a conserved double glycine suggests the McpM precursor contains an 18 residue signal peptide that is cleaved to produce a mature MccPDI. There is no apparent sequence identity with other microcins in the activity region (C-terminal sequence) (6).

This indicates that a unique receptor is probably involved with the uptake of MccPDI and that the mechanism of killing is different from other microcins. The fact that only *E. coli* and *Shigella* (data not shown) are currently known to be susceptible to this PDI (MccPDI) suggests target cell recognition occurs through a specific receptor, possibly only expressed in these species.

Class IIa microcin gene clusters are typically composed of only four genes: two necessary for microcin export, one for immunity, and one encoding the microcin. The PDI operon is unique because it also includes a gene presumably involved with microcin processing or export. Deleting mcpA in *E. coli*-25 interrupts the inhibitory phenotype but does not affect immunity. It is possible this mutant has downstream effects on the microcin transport system (i.e. a polar effect); however, not to be bound by theory, bioinformatic analysis suggests the protein product is likely to be involved with post-translational modification of McpM. McpA has similarity to McmM and MceF (both 29% identity) of the MccM and MccE492 gene clusters, respectively. Wilkens et al. (36) showed an mceF mutant had a non-inhibitory phenotype and the microcin product collected from cell lysate was found at a higher molecular weight than mature MccE492, suggesting the presence of an inactive microcin precursor. Consistent with a role in protein modification, McpA contains a CaaX amino terminal protease domain (PF02517) that functions in post-translation modification of proteins with the CaaX sequence motif (35). Furthermore, the McpM C-terminus putatively contains a modified terminal CaaX sequence, suggesting McpM may be processed either before or during transport, resulting in the fully mature MccPDI.

Although microcins are released extracellularly to inhibit competing bacteria, no antimicrobial compounds were detected through membrane-divided competitions or spent media assays in previous work (32). It is possible the PDI microcin requires contact between competing cells or some other signal to become active in the media. Alternatively, the methods used in the Examples section herein may interfere with the detection of a soluble microcin in these assays, or the concentration of secreted microcin is too low to have a biological effect except when inhibitor cells express the microcin in close proximity to susceptible strains. Without being bound by theory, it is likely that MccPDI interacts with an outer membrane protein OmpF, which is highly conserved in all sequenced *E. coli* and *Shigella*. Data presented in Example 12 below shows that six genes (atpA, atpF, dsbA, dsbB, ompF, and ompR) were required for susceptibility to PDI, suggesting that OmpF acts as the receptor for MccPDI and the other genes required for sensitivity are necessary for expression and folding of OmpF, and/or they are required to translocate MccPDI across the cellular membrane.

Figure 4:
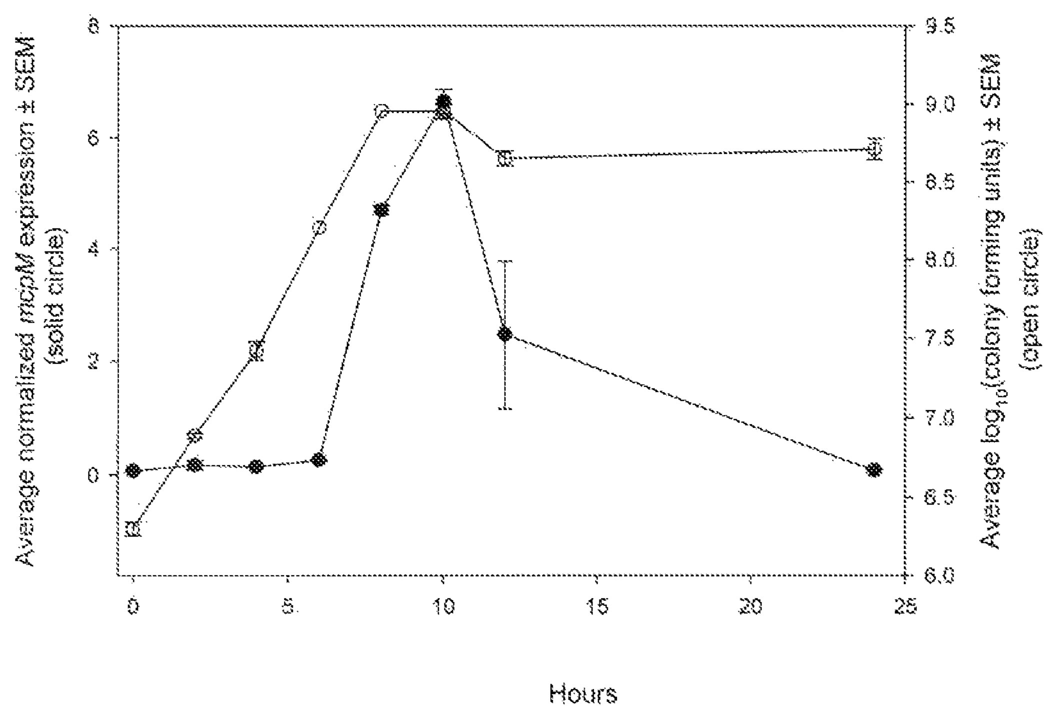
FIG. 4. Expression of mcpM by *E. coli*-25 is correlated with growth phase. Expression of mcpM was measured during 24 hr culture in M9. Closed circles are the mean normalized mcpM expression±SEM (n=2 replicates). Open circles are the mean colony forming units (CFU)±SEM (n=2 replicates).

Like other microcins, MccPDI is a low molecular weight protein that inhibits the growth of closely related species. However, where the activity of some microcins extends to a range of Gram-negative bacteria including *Escherichia, Klebsiella, Salmonella*, and *Pseudomonas* (6), MccPDI has only been observed to inhibit *Escherichia*, and testing has also shown inhibition of *Shigella* but not *Salmonella* or *Klebsiella* (data not shown). In Examples presented below, the PDI$^+$ strain *E. coli*-25 was competed against a panel of pathogenic *E. coli* O157:H7 (n=25) and *E. coli* O26 (n=3). All the strains were susceptible to killing (FIG. 1) and the average reduction following co-culture was greater than 5 logs. The degree of killing may actually be much greater as our methods to determine cell counts were limited to $2\times10^3$ CFU/m. Calculations for the degree of killing were determined using $2\times10^3$ CFU/ml for instances where the susceptible population was undetectable. Nonetheless, PDI effectively kills greater than 99% of the competing population. Because many of these pathogens are significant in diseases of both animals and humans (33), MccPDI has application in clinical medicine, food safety and other fields. FIG. 4 shows that native mcpM transcription occurs primarily during rapid growth of the inhibitor population.

The invention provides methods and compositions for killing and/or for preventing or decreasing the adverse effects of pathogenic bacteria such as pathogenic *Escherichia coli* (*E. coli*). The methods involve contacting the pathogenic bacteria with the novel microcin described herein, microcin MccPDI, the amino acid sequence of which is presented in SEQ ID NO: 24. The contact may be via a preparation of the microcin itself, or via a preparation of a bacterium encoding the microcin, as described in detail below.

Hosts, Pathogens and Sources of Contamination

While most *E. coli* strains are harmless, some serotypes can cause serious and even deadly diseases in a host, either as the result of exposure to the pathogenic bacteria via direct transmission from another infected host or by ingestion of or exposure to (e.g. handling) contaminated food products or from other sources of the bacteria (e.g. fomites). In particular, the targeted pathogenic bacteria include *E. coli* strains expressing the OmpF protein, which are known to be vulnerable to the MccPDI microcin. The methods and compositions are also effective for killing (e.g. lysing) or preventing or decreasing the adverse effects of pathogenic *Shigella* sp. Those of skill in the art will recognize that phylogenetic studies indicate that *Shigella* is more appropriately treated as a subgenus of *Escherichia*, and that certain strains generally considered *E. coli* (e.g. *E. coli O*157:H7) could be classified as *Shigella*. Herein, the phrases "pathogenic bacteria" and "pathogenic *E. coli*" encompasses both pathogenic *E. coli* and pathogenic *Shigella*, although the two may be discussed separately, for clarity and to accord with historic designations.

The term "pathogenic" refers to the ability of the bacterium to cause disease symptoms in one or more hosts. The targeted bacterium need not cause disease in all hosts that is it capable of colonizing. Successful colonization of some hosts by the bacterium may be entirely benign (asymptomatic, harmless, etc.). However, such non-susceptible hosts may serve as reservoirs of the pathogenic bacteria which, when transmitted to a susceptible host, cause disease. Herein, these two genres of hosts may be referred to as "disease susceptible hosts" and "non-disease susceptible hosts", respectively, or simply as "susceptible hosts" and "non-susceptible hosts". It will be understood that the methods of treatment described herein may be advantageously applied to both susceptible and non-susceptible hosts. For the susceptible hosts, treatment may prevent, cure (fully or partially) or ameliorate disease symptoms, or prevent or decrease adverse effects that would otherwise be caused by pathogenic bacteria. These beneficial effects are brought about by killing and/or damaging established pathogenic bacteria, or by preventing, slowing or minimizing the growth of pathogenic bacteria to which the host is newly exposed. For non-susceptible hosts, treatment may destroy or lessen the number of pathogenic bacteria that can colonize the host or that might otherwise colonize the host, but for intervention using the methods and compositions described herein, thereby lessening or eliminating transmission of the pathogenic bacteria to other disease susceptible and non-susceptible hosts.

Susceptible hosts that may be subject to diseases caused by pathogenic *E. coli* are usually endotherms and may be mammals. Such mammals include but are not limited to: primates (e.g. humans), livestock e.g. cattle, pigs, sheep goats, etc., especially neonates, juveniles, elderly or immune compromised individuals; etc. Alternatively, various avian species may also be subject to such infections, including but not limited to: chickens, turkeys, ducks, etc. Non-susceptible hosts that may act as reservoirs of pathogenic bacteria that are passed to susceptible hosts include substantially the same endotherms described above as susceptible hosts.

Further, pathogenic bacteria may be transmitted among members of a particular host group (e.g. from person to person, among cows in a herd, etc.) or even from one area of an individual host organism to another area of the same organism, e.g. pathogenic bacteria may be transmitted from the anus to the urethra via fecal contamination, causing urethral infection.

Particular combinations of susceptible hosts and pathogenic bacteria include the following exemplary animal pathogens of interest:

Poultry—avian pathogenic *E. coli* (APEC)
Calves—*E. coli* K99 (which causes calf diarrhea)
Swine—*E. coli* K88 (which causes post-weaning diarrhea)
For food safety:
*E. coli* O157:H7
The United States Department of Agriculture (USDA) "Big 6" STEC *E. coli* pathogens: *E. coli* serovars O26, O45, O103, O111, O121 and O145.
Diarrhoeagenic *E. coli* human pathovars:
various enteropathogenic *E. coli* (EPEC)
various enterohaemorrhagic *E. coli* (EHEC)
various enterotoxigenic *E. coli* (ETEC)
various enteroinvasive *E. coli* (EIEC; including *Shigella*)
various enteroaggregative *E. coli* (EAEC)
various so-called diffusely adherent *E. coli* (DAEC)
Extraintestinal *E. coli* (ExPEC) human pathovars:
uropathogenic *E. coli* (UPEC)
neonatal meningitis *E. coli* (NMEC)

Exemplary pathogenic *Shigella* species of interest which may be killed by the compositions and methods of the invention include but are not limited to: Serogroup A: *S. dysenteriae*, Serogroup B: *S. flexneri*, and Serogroup D: *S. sonnei*, and serotypes and serovars thereof.

In addition, contamination with pathogenic bacteria can occur via other routes of transmission such via fomites, (inanimate objects such as countertops, cutting boards, utensils, towels, money, clothing, dishes, toys, dirt, excreted feces, diapers, surfaces in barns and stockyards, etc.), or via unpasteurized milk, dairy products, juices, etc.; or via contaminated water (e.g. drinking water, ponds and lakes, swimming pools, etc.); or via contaminated animals, meat, or produce; or fruits, etc.

In some aspects, the methods of the invention involve contacting pathogenic bacteria with the microcin MccPDI. Accordingly, the invention provides i) substantially purified MccPDI microcin protein; and ii) substantially pure cultures of bacteria that produce the microcin protein.

Proteins and Nucleic Acids

In some aspects, the invention provides MccPDI microcin protein and/or a gene that encodes the protein (e.g. SEQ ID NOS: 23 or 33 and 24) as well as proteins/polypeptides of the operon disclosed herein, and the genes which encode them (e.g. SEQ ID NOS: 25-32).

Substantially purified MccPDI microcin protein may be produced either recombinantly, or from a native or naturally occurring source such as the bacteria described herein. Those of skill in the art are familiar with techniques for genetically engineering organisms to recombinantly produce or overproduce a protein of interest such as MccPDI. Generally, such techniques involve excision of a gene encoding the protein from a natural source e.g. using nucleases or by amplifying the gene e.g. via PCR using primers complementary to sequences that flank the gene of interest. The gene can then be inserted into and positioned within a vector (e.g. an expression vector such as a plasmid or virus) so that it is able to be expressed (transcribed into translatable mRNA). Typically, the gene that is to be transcribed is juxtaposed to one or more suitable control elements such as promoters, enhancers, etc. which drive expression of the gene. Suitable vectors include but are not limited to: plasmids, adenoviral vectors, baculovirus vectors (e.g. so-called shuttle or "bacmid" vectors, and the like). Suitable vectors may be chosen or constructed to contain appropriate regulatory sequences, including promoter sequences, terminator sequences, polyadenylation sequences, enhancer sequences, marker genes, and other sequences. The vectors may also contain a plasmid or viral backbone.

Typically, the vector is used to genetically engineer or infect a host organism where the gene is transcribed and translated into protein. In the host, the gene may be expressed from the vector (transcribed extrachromasomally) and may be overexpressed, i.e. expressed at a level that is higher than normally occurs in its native bacterial host. Alternatively, the gene may be inserted into the chromosome of the host. Exemplary expression systems that may be utilized include but are not limited to bacteria (such as *E. coli*), yeast, baculovirus, plant, mammalian, and cell-free systems. Host bacteria may be heterologous, i.e. they may be non-native bacteria in which the gene is not present in nature. Alternatively, they may be native bacteria that are natural hosts, but which are genetically engineered to produce the microcin in greater abundance (at higher levels or concentrations) than in the native, non-engineered host. Exemplary heterologous bacterial hosts include but are not limited to: various *lactobacillus* species such as *Lactobacillus casei, Lactobacillus acidophilus, Lactobacillus fermentum, Lactobacillus gasseri, Lactobacillus pentosus, Lactobacillus plantarum, Lactobacillus sporogenes, Lactobacillus brevis, Lactobacillus delbrueckii, Lactobacillus salivarius, Lactobacillus hilgardii, Lactobacillus lactis, Lactobacillus rhamnous, Lactobacillus johnsonii. Lactobacillus leishmanis, Lactobacillus jensenii, Lactobacillus reuteri, Lactobacillus sakei, Lactobacillus cellobiosus, Lactobacillus crispatus, Lactobacillus curvatus, Lactobacillus caucasicus*, and *Lactobacillus helveticus*, and others taught, for example, in United States patent application 20090169582 (Chua), the complete contents of which is hereby incorporated by reference in entirety; and other types of bacterial, fungal and/or viral recombinant hosts. Mammalian cells available in the art for heterologous protein expression include lymphocytic cell lines (e.g., NSO), HEK293 cells, Chinese hamster ovary (CHO) cells, COS cells, HeLa cells, baby hamster kidney cells, oocyte cells, and cells from a transgenic animal, e.g., mammary epithelial cell. For details, see Sambrook et al., Molecular Cloning: A Laboratory Manual, 2nd ed., Cold Spring Harbor Laboratory Press (1989). Many established techniques used with vectors, including the manipulation, preparation, mutagenesis sequencing, and transfection of DNA, are described in Current Protocols in Molecular Biology, Second Edition, Ausubel et al. eds., John Wiley & Sons (1992).

The vector or chromosome from which the microcin is transcribed includes at least a genetic sequence encoding the microcin described herein and may comprise one or more additional genes of the operon described herein, i.e. genes mcpM (SEQ ID NO: 23), mcpI (SEQ ID NO: 25), mcpA (SEQ ID NO: 27), mcpD (SEQ ID NO: 29), and mcpB (SEQ ID NO: 31), each of which encodes a respective protein or functional variant thereof (see below for explanation of "variant". The one or more (at least one) gene(s) in the vector or chromosome is/are expressable and are operably (functionally, expressibly) linked to one or more control or expression elements, e.g. promoters, enhancers, etc. in a manner that facilitates, causes or allows expression of the gene(s). In some aspects, the genes are present on a plasmid such as the plasmid with the nucleotide sequence shown in SEQ ID NO: 33), or a plasmid with at least about 55, 60, 65, 70, 75, 80, 85, 90, or 95% or more (e.g. 96, 97, 98, 99%) identity. The plasmid may be located in a native host bacterium, e.g. E-25 (which is resistant to tetracycline, streptomycin and sulfa drugs) and/or E-264 (which is not antibiotic resistant).

The protein that is produced is the microcin MccPDI (or another protein encode by the operon as described above) or a physiologically active variant thereof. By "physiologically active variant" or "active variant" or "functional variant", we mean a protein sequence that is able to kill pathogenic bacteria as described herein. The protein may have the sequence shown in SEQ ID NO: 24, or may include this sequence, or a sequence that shares at least about 95% identity to SEQ ID NO: 24 (e.g. that is about 95, 96, 97, 98 or 99% identical thereto, as determined by alignment methods that are well-known), but that retains the ability to kill and/or impede growth/reproduction of and/or colonization by pathogenic bacteria. Compared to the wild type microcin, such variants are at least about 50%, and usually about 55, 60, 65, 70, 75, 80, 85, 90, or 95% or more as potent re killing, impeding growth and/or colonization, etc. In some embodiments, the variant may be more potent than the native microcin.

The variants of MccPDI that may be used in the practice of the invention may include those in which one or more amino acids are substituted by conservative or non-conservative amino acids, as is understood in the art. Further, deletions or insertions may also be tolerated without impairing the function. In addition, the microcin may be included in a chimeric or fusion protein that includes other useful sequences, e.g. tagging sequences (e.g. histidine tags), various targeting sequences (e.g. sequences that promote secretion or target the protein to a subcellular apartment or to the membrane), other antimicrobial sequences (e.g. other microcins), and the like, as well as spacer or linking sequences. The sequence of the microcin may be altered to prevent or discourage proteolysis, to promote solubility, or in any other suitable manner.

Some aspects of the invention provide a microcin with a sequence such as that shown in SEQ ID NO: 24, but which is foreshortened by 18 amino acids at the amino terminus, i.e. the 18 amino terminal residues present in SEQ ID NO: 24 are absent in this sequence, which is shown below as SEQ ID NO: 35. As described above for SEQ ID 24, active variants of the sequence represented by SEQ ID NO: 35 are also encompassed by the invention.

```
                                        (SEQ ID NO: 35)
N A N S N F E G G P R N D R S S G A R N S L

G R N A P T H I Y S D P S T V K C A N A

V F S G M I G G A I K G G P I G M A R G T I

G G A V V G Q C L S D H G S G N G S G N

R G S S S S C S G N N V G T C N R.
```

The invention also encompasses nucleic acid sequences that encode the microcin and active variants thereof as described herein. For example, the encoding sequence may be that which is represented in SEQ ID NO: 23, but this is not always the case. Variants of SEQ ID NO: 23, usually having at least about 95, 96, 97, 98, or 99% identity thereto, are also contemplated. However, those of skill in the art will recognize that the identity may be much lower (e.g. about 50, 55, 60, 65, 70, 75, 80, 85 or 90%) and the sequence may still encode a fully functional microcin, e.g. due to the redundancy of the genetic code.

Calculations of "homology" and/or "sequence identity" between two sequences may be performed as follows: The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference (native) sequence. The amino acid residues or nucleotides at corresponding amino acid positions or nucleotide positions are then compared. When a position the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In an exemplary embodiment, the percent identity between two amino acid sequences is determined using the Needleman and Wunsch (1970, J. Mol. Biol. 48:444-453) algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In an exemplary embodiment, the percent homology/identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that may be used if the practitioner is uncertain about what parameters may be applied to determine if a molecule is within a sequence identity, or homology limitation of the invention) are a Blossum 62 scoring matrix with a gap penalty of 12, a gap extend penalty of 4, and a frame shift gap penalty of 5. The percent identity/homology between two amino acid or nucleotide sequences can also be determined using the algorithm of E. Meyers and W. Miller ((1988) CABIOS, 4:11-17) that has been incorporated into the ALIGN program (version 2:0); using a PAM120 weight residue table, a gap length penalty of 12 and a gap penalty of 4.

The culturing and the maintenance of cultures of microorganisms such as the bacteria of the invention is carried out e.g. as described herein in the Examples section. Bacterial preparations may be lyophilized or freeze-dried.

The production of the substantially purified microcin protein is carried out by methods known to those of skill in the art, e.g. by collecting unpurified protein from a source such as the bacteria (or other expression system) that make the protein, and purifying and characterizing the protein using known steps, e.g. various separation techniques and identification techniques which include but are not limited to: centrifugation, column chromatography, affinity chromatography, electrophoresis, precipitation, sequencing, spectroscopy, etc. Preparations may be lyophilized or freeze-dried. By "substantially purified" we mean that the microcin is provided in a form that is at least about 75 wt %, preferably at least about 80 wt %, more preferably at least about 90 wt %, and most preferably at least about 95 wt % or more free from other macromolecules such as other peptides, proteins, nucleic acids, lipids, membrane fragments, etc., as is understood by those of skill in the art.

Compositions

The microcins and/or bacteria producing microcins (both of which may be referred to herein as "active agent(s) or "active ingredient(s))" of this invention will generally be used as a bactericidal active ingredient in a composition, i.e. a formulation, with at least one additional component such as a surfactant, a solid or liquid diluent, etc., which serves as a carrier. The formulation or composition ingredients are selected to be consistent with the physical properties of the active ingredient, the mode of application and environmental factors at the site of use, e.g. such as surface type, (e.g. soil or solid substrate, etc.), moisture, temperature, etc. If the composition is to be administered to a host, the ingredients are selected so as to be physiologically compatible with the host. Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspoemulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, films, filled or layered films, coatings, impregnations, gels, cakes, and the like, which can be water-dispersible ("wettable") or water-soluble. Films and coatings formed from film-forming solutions or flowable suspensions may be useful for some applications. Active ingredients can be (micro) encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions may be used as intermediates for further formulation.

Sprayable formulations are typically extended in a suitable medium before spraying. Liquid and solid formulations are formulated to be readily diluted in the spray medium, which may be aqueous-based, e.g. water. Spray volumes can range from about one to several thousand liters, sprayable formulations may be tank mixed with water or another suitable medium for treatment by aerial or ground application, e.g. of stockyards, barns, stables, stalls, bins containing produce, etc. Smaller volume spray formulations for use on smaller surfaces (e.g. countertops, for application to small quantities of food stuffs, etc.) are also contemplated.

The formulations will typically contain effective amounts of active ingredient in the range of about 1 to about 99 percent by weight.

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., Handbook of Insecticide Dust Diluents and Carriers, 2nd Ed., Dorland Books, Caldwell, N.J., the complete contents of which is hereby incorporated by reference in entirety.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and .gamma.-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, Solvents Guide, 2nd Ed., Interscience, New York, 1950, the complete contents of which is hereby incorporated by reference in entirety.

The solid and liquid compositions of the present invention may include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents. Surfactants can be classified as nonionic, anionic or cationic. Exemplary suitable surfactants can be found, for example, in United States patent application 20130143940 to Long, the entire contents of which is hereby incorporated by reference. Also useful for the present compositions are mixtures of nonionic and anionic surfactants or mixtures of nonionic and cationic surfactants. Nonionic, anionic and cationic surfactants and their recommended uses are disclosed in a variety of published references including McCutcheon's Emulsifiers and Detergents, annual American and International Editions published by McCutcheon's Division, The Manufacturing Confectioner Publishing Co.; Sisely and Wood, Encyclopedia of Surface Active Agents, Chemical Publ. Co., Inc., New York, 1964; and A. S. Davidson and B. Milwidsky, Synthetic Detergents, Seventh Edition, John Wiley and Sons, New York, 1987, the complete contents of each of which is hereby incorporated by reference in entirety.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co., the complete contents of which is hereby incorporated by reference in entirety.

The active agents described herein and any other active ingredients are typically incorporated into the present compositions by dissolving or suspending the active ingredient in a solvent or by grinding in a liquid or dry diluent. Solutions, including emulsifiable concentrates, can be prepared by simply mixing the ingredients. The preparation may be lyophilized (freeze dried). If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084, the complete contents of which is hereby incorporated by reference in entirety) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", Chemical Engineering, Dec. 4, 1967, pp 147-48, Perry's Chemical Engineer's Handbook, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566. For further information regarding the art of formulation, see T. S. Woods, "The Formulator's Toolbox-Product Forms for Modern Agriculture" in Pesticide Chemistry and Bioscience, The Food-Environment Challenge, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, Weed Control as a Science, John Wiley and Sons, Inc., New York, 1961, pp 81-96; Hance et al., Weed Control Handbook, 8th Ed., Blackwell Scientific Publications, Oxford, 1989; and Developments in formulation technology, PJB Publications, Richmond, UK, 2000. The complete contents of each of these references is hereby incorporated by reference in entirety.

In addition, the formulations may include other suitable active agents, e.g. other antimicrobial agents such as other microcins, antibiotics, etc.; or broadly defined antimicrobials such as antiseptics or heavy metals, etc.

Incorporation into Various Products

The active agents described herein may be incorporated into and/or used as an amendment to many different products, e.g. substrates and media which include but are not limited to: so-called "hand-sanitizing" preparations and soaps, gels, etc.; various sprays and washes; detergents and various cleaning agents; fabrics e.g. linings for materials such as diapers and other garments that may be contacted by feces; "booties" that are used to cover and protect shoes; disposable or non-disposable gloves; disposable or non-disposable food preparation surfaces, e.g. as sheets of material that can be placed on a cutting surface, or in a cutting surface itself, in storage apparatuses for implements used in food preparation (e.g. knife blocks, or holders, etc.); and others.

In some aspects, the active agents described herein are incorporated into packaging materials, e.g. packaging materials designed to contain meat or meat products or produce. For example, the packaging material may be impregnated with the active agent either during or after manufacture, or may be coated onto one or more surfaces of the material. The packaging material may be a film e.g. formed from a flexible polymer that may be transparent, or may be a rigid or semi-rigid container formed from e.g. plastic resin, styrofoam, wood, cardboard or pasteboard or other molded cellulose product, or made from some other so-called "natural" material. The packaging material may be in the form of "peanuts". The material may be biodegradable. United States patent applications 20120259295 (Bonutti) and 20030234466 (Rasmussen) and references cited therein, the complete contents of all of which are hereby incorporated by reference in entirety, discuss the preparation of various types of packaging materials.

The active agents may be incorporated into probiotic formulations. Such formulations may be designed or tailored to suit the mode of administration and the host to which the probiotic is administered. For example, if the targeted host is a human, the active agents may be added to other known probiotic products (kefir, yogurts, "smoothies", etc.) and/or other ingredients that increase palatability may be added (e.g. flavorings, thickeners, coloring agents, etc.). The formulation may be chewable (e.g. a gum or tablet) or taken as a pill. Other organisms may also be present in the probiotic preparation e.g. lactic acid bacteria (LAB), bifidobacteria, yeasts and various bacilli. If the recipient host is a juvenile such as a calf, the probiotic may be a milk substitute formulation. If the recipient is a bird or fowl, the probiotic may be a formulation of drinking water. Probiotics may also be formulated as suppositories.

Methods and Uses

In some aspects, the invention provides methods of using the microcins and bacteria that produce the microcins described herein, for preventing or decreasing the transmission of pathogenic *Escherichia coli* (*E. coli*) bacteria from a first location to a second location, e.g. from a first host (that may or not be a susceptible host) or first contaminated area, to a second host or previously uncontaminated area. The second host may or may not be susceptible. The first location may be a "reservoir" host or area/location that is already colonized by the pathogenic bacteria. Alternatively, the first host or location may be likely to be colonized or possible to colonize.

Administration to Hosts

If the first location is a susceptible (or non-susceptible) first host, the method comprises administering to the first host the microcin described herein or a bacterium that contains and expresses a nucleotide sequence encoding the microcin. By "administering" we mean the deliberate, intentional, active introduction of the bacterium into the first host (i.e. the purposeful inoculation of the first host), usually by a human or by a device, instrument or machine designed and operated by a human. In other words, the bacterium is not inadvertently, passively or accidentally transmitted, or is not transmitted as the result of an act of nature, or as the result of contamination of a source of the bacteria. Generally, the "bacterium" that is deliberately administered is a substantially pure, genetically homogenous population of substantially identical bacteria, or part of a mixture of several types of such substantially pure bacteria (e.g. several different serotypes, serovars, or strains. The bacteria that are so administered are generally cultured in vitro for a time prior to administration, and the method may involve culturing the bacteria from a natural source, selecting a single colony for propagation, and propagating the bacteria to form a culture that is sufficiently large or populous to successfully inoculate a host.

Administration results in contact between pathogenic bacteria that reside in/on the first host and the killing or damaging, etc. of the pathogens. Alternatively, administration may be prophylactic, i.e. the first host is not already infected with the pathogen, and infection is prevented or decreased. If bacteria are administered, the step of administering may also result in colonization of a host that is treated with the administered bacteria, i.e. bacteria that have the gene encoding the microcin. Thus, in some aspects, the step of administering results in an alteration of the microflora (e.g. "gut" or "digestive tract" microflora) of the recipient host, and the bacteria thus are a "probiotic" as discussed elsewhere herein, competing for nutrition and attachment sites to within the host. "Digestive tract" includes e.g. the mouth, esophagus, stomach, small intestine and large intestine (which includes the cecum, colon and rectum). In general, the amount of microcin that is administered in order to be effective is in the range of from about the amount of microcin would range between about 1 ug and 100 mg depending on the application and dilution factor; and the amount of bacteria that is administered in order to be effective is in the range of from about $10^3$ to about $10^{12}$, and is preferably in the range of from about $10^6$ to about $10^9$. Those of skill in the art will recognize that variations may occur, depending e.g. on how much microcin is produced by the bacterial strain in question, by the species, size, age, etc. of the subject to whom the microcin and/or the bacteria (or other recombinant host that produces the microcin) is administered.

When the microcin is administered, it may be in any suitable form or incorporated into any suitable vehicle. Exemplary vehicles for administering the microcin include but are not limited to: liquids such as drinking water, formula, and the like; and solid or semi-solid forms such as suppositories, pills, tablets, etc. The vehicle may be a solid "slow release" vehicle. The vehicle may include or be contained within e.g. a permeable or semi-permeable bag or pouch which can be suspended or retained indefinitely in the gut of a host organism (e.g. a cow), from which the active agent leaches or is released over time. The bag or pouch may be biodegradable.

For avian hosts (e.g. chickens), an exemplary mode of administration is addition of microcin-producing bacteria to drinking water or feed. Administration in this manner may be termed "probiotic" because the goal is to encourage colonization of the bird's digestive system with the harmless, protective bacteria, although colonization is not a requirement for positive effects to accrue. The protective microcin-producing bacteria can destroy or kill and thus outcompete pathogenic bacteria encountered by the bird, preventing colonization by the pathogens, or a least decreasing the level of colonization of, and hence transmission from, the bird. If the microcin itself is added to the drinking water or feed, it will destroy or kill pathogenic bacteria encountered by the bird, preventing colonization by the pathogens, or a least decreasing the level of colonization of, and hence transmission from, the bird, and possibly allow other non-pathogenic bacteria to flourish.

Similar strategies may be employed for bovine hosts, e.g. addition of microcin-producing bacteria or the microcin itself to drinking water, feed, salt licks, calf formula, etc., or administration of the bacteria as a probiotic to encourage the establishment of microcin-producing bacteria as described herein, or to provide a protective shield against infection by pathogenic bacteria.

Application to Surfaces

Those of skill in the art will recognize that it is also beneficial to prevent (discourage, impede, lessen, decrease, etc.) transmission of pathogenic bacteria from non-host sources to possible hosts, e.g. to prevent transmission from surfaces or areas which harbor the pathogens. The invention also comprises methods of doing so by applying the microcin of the invention and/or bacteria encoding the microcin, to surfaces which harbor the pathogens, or which are suspected or harboring the pathogens, or which could become contaminated with pathogens. Applying or treating such surfaces may be accomplished by any of many methods, e.g. by spraying a preparation of the microcin or bacteria, by applying a composition comprising a powder or granules, etc. Suitable compositions are described above. In general, the amount of microcin that is applied to a surface in order to be effective is in the range of from between about 1 ug and 100 mg; and the amount of bacteria that is applied is in the range of from about $10^3$ to about $10^{12}$, and is preferably in the range of from about $10^6$ to about $10^9$.

Areas that are particularly prone to contamination with pathogenic bacteria include those which house of livestock or fowl. Such areas, especially commercial areas, may be treated using the compositions of the invention, especially spray formulations. The areas may or may not be associated with a commercial enterprise, e.g. they may be associated with for profit or non-profit farms, stables, etc. The areas may also be set aside for animals e.g. as reserves, zoos, stockyards etc., or may be located at veterinary facilities. The compositions of the invention may be applied to any suitable surface where the microcin may be useful to kill pathogenic bacteria, e.g. soil or grass, flooring, stalls, pens, milking carousels, feed lot surfaces, drinking and/or feeding containers, cages, crates, truck beds, etc. Exemplary animals which are housed in such areas and are potential hosts of pathogenic bacteria include but are not limited to: livestock e.g. horses, mares, mules, jacks, jennies, colts, cows, calves, yearlings, bulls, oxen, sheep, goats, lambs, kids, hogs, shoats, pigs, bison, and others; and avian species such as land and water fowl e.g. chickens, turkeys, ducks, geese, ostriches, guinea fowl, etc. The preparations of the invention may be applied to the animals themselves, or to specific areas of the animals, e.g. to feet, the anal area, etc.

In addition, the preparations of the invention may be applied to various products, especially products derived from animals that are susceptible to infection with and/or to disease caused by pathogenic bacteria. The preparations may be applied to or included in (mixed into), for example, meats or meat products (including both raw and so-called "ready to eat" meat and poultry products), eggs, hides, carcasses, horns, hooves, feathers, etc.

Diseases Prevented or Treated

The types of diseases and conditions that may be prevented or treated using the methods and compositions disclosed herein include any of those which are caused by pathogenic *E. coli*, including but are not limited to: food poisoning (e.g. in humans), gastroenteritis, diarrhea, urinary tract infections, neonatal meningitis, hemolytic-uremic syndrome, peritonitis, mastitis, septicemia and Gram-negative pneumonia, shigellosis, dysentery, etc. In some aspects, probiotic preparations are contemplated, e.g. liquid or solid preparations that are taken prophylactically to prevent or treat disease symptoms or so-called Traveler's diarrhea prior to or during travel.

Herein, where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

EXAMPLES

Example 1

Materials and Methods

Bacterial Strains, Media, and Culture Conditions.

*E. coli* strains (Table 1) were cultured in Luria-Bertani (LB) media (Fisher Scientific, Pittsburgh, Pa.) or in M9 minimal media (6 g/L $Na_2HPO_4$, 3 g/L $KH_2PO_4$, 0.5 g/L NaCl, 1 g/l $NH_4Cl$, 2 mg (L thiamine, 1 mM $MgSO_4$ 0.1 mM $CaCl_2$ and 0.2% glucose) at 37° C. with shaking (200 rpm), unless stated otherwise. Components for the M9 media were purchased from Fisher Scientific (Pittsburgh, Pa.), Sigma-Aldrich (St. Louis, Mo.) and J. T. Baker Reagents and Chemicals (Phillipsburg, N.J.). Antibiotics were added to media at the following concentrations: ampicillin (amp) 100 μg/ml (Fisher Biotech, Fair Lawn, N.J.); kanamycin (kan) 50 μg/ml (Fisher Scientific. Pittsburgh, Pa.); nalidixic acid (nal) 30 μg/ml (MP Biomedicals, Solon, Ohio); and tetracycline (tet) 50 μg/ml (Fisher Scientific, Pittsburgh, Pa.). Strains that would otherwise be antibiotic susceptible were selected for nalidixic acid resistance through successive passage in LB media with increasing nalidixic acid concentrations until the strains were capable of growth at 30 μg/ml.

TABLE 1

*E. coli* strains and PCR primer sequences used in this work.

| Strain | Genotype/phenotype | Primers: Homologous extensions (H1[a] and H2[b]); PDI, rpoD, and mcpM loci | Ref. |
|---|---|---|---|
| *E.coli*-25 | Wild-type, $SSuT^R$, $PDI^+$ | PDI fwd: TAGTTGCAGGGGCATAAGAA (SEQ ID NO: 1)<br>PDI REV: AGGAAACGCAAACAGCAACT (SEQ ID NO: 2)<br>rpoD fwd: CAGGTTCAATGCTCCGTTGC (SEQ ID NO: 3)<br>rpoD rev: GCGACCTTTCGCTTTGATGG SEQ ID NO: 4)<br>mcpM fwd: CCGTAATGACCGTTCCAGT (SEQ ID NO: 5)<br>mcpM rev: CCATTTCCACTACCATGATCT (SEQ ID NO: 6) | (17) |
| *E. coli*-25ΔtolC | $SSuT^R$, $Kan^R$, ΔtolC, $PDI^-$ | H1: ATAACCCGTATCTTTACGTTGCCT TACGTTCA (SEQ ID NO: 7)<br>H2: CTAGAATCCGCAATAATTTTACAGTTTGAT (SEQ ID NO: 8) | This work |

TABLE 1-continued

| *E. coli* strains and PCR primer sequences used in this work. | | | |
|---|---|---|---|
| Strain | Genotype/phenotype | Primers: Homologous extensions (H1[a] and H2[b]); PDI, rpoD, and mcpM loci | Ref. |
| *E. coli*-25ΔtraM | $SSuT^R$, $Kan^R$, ΔtraM, $PDI^+$ | H1: AATAACGTGATTGCATATTACT TATCTCAGGAGTTC (SEQ ID NO: 9) H2: ATCCCTGGAAGGACTACAACC TATGACCGAAAATAC (SEQ ID NO: 10) | This work |
| *E. coli*-25ΔmcpM | $SSuT^R$, $Kan^R$, ΔmcpM, $PDI^-$ | H1: GTAATTTAATAAACATAGTAG CGCCCTCCATTATATCTAT (SEQ ID NO: 11) H2: AACGCACAAAATAACAAACAA CCGATAGGGGAAATATGAT (SEQ ID NO: 12) | This work |
| *E. coli*-25ΔmcpMΔmcpI | $SSuT^R$, $Kan^R$, ΔmcpMΔmcpI, $PDI^-$ | H1: ATTATCTTTACTATATTTATAT ATGTTATCATTCATAATG (SEQ ID NO: 13) H2: AACGCACAAAATAACAAACAA CCGATAGGGGAAATATGAT (SEQ ID NO: 14) | This work |
| *E. coli*-25ΔmcpMΔmcpI + pMcpI | $SSuT^R$, $Kan^R$, ΔmcpMΔmcpI, $PDI^-$, immune to PDI | H1: TGGTGATGAATTCCTGTCAAA (SEQ ID NO: 15) | |
| *E. coli*-25ΔmcpB | $SSuT^R$, $Kan^R$, ΔmcpB, $PDI^-$ | H2: TACCAGTTTCACCCGTCACA (SEQ ID NO: 16) | This work |
| *E. coli*-25ΔmcpD | $SSuT^R$, $Kan^R$, ΔmcpD, $PDI^-$ | H1: TCAGCCATTCCCATAAATGAC GAGTATCAAGGTTGACG (SEQ ID NO: 17) H2: TTGACGGAAAGGTTACTTATTG TATTAAAAATAATG (SEQ ID NO: 18) | This work |
| *E. coli*-25ΔmcpA | $SSuT^R$, $Kan^R$, ΔmcpA, $PDI^-$ | H1: GATATACATCTGACCTGTGTGA TGTTAAAGTTTTATACTA (SEQ ID NO: 19) H2: ATAGAAAAAATAAGAACAATC TCCGCGAAATAGCATTATG (SEQ ID NO: 20) | This work |
| *E. coli*-4 | Wild-type, $SSuT^R$, $PDI^-$ | | (32) |
| *E. coli*-4pPDI | $SSuT^R$, $Kan^R$, pPDI, $PDI^+$ | | This work |
| *E. coli*-6 | Wild-type, $SSuT^R$, $PDI^-$ | | (32) |
| *E. coli*-82 | Wild-type, $SSuT^R$, $PDI^-$ | | This work |
| *E. coli*-186 | Wild-type, $Nal^R$, $PDI^-$ | | (32) |
| *E. coli*-264 | Wild-type, $Nal^R$, $PDI^+$ | | (32) |

TABLE 1-continued

*E. coli* strains and PCR primer sequences used in this work.

| Strain | Genotype/phenotype | Primers: Homologous extensions (H1[a] and H2[b]); PDI, rpoD, and mcpM loci | Ref. |
|---|---|---|---|
| O157:H7 Sakai | Wild-type | | (15) |
| *E. coli* K12 | $Nal^R$ | | (19) |

[a]*E. coli*-25 gene-specific sequences are shown. For gene deletion mutants, homologous extensions also had the kanamycin primer site: TGTGTAGGCTGGAGCTGCTTCG (SEQ ID NO: 21), 3' to the *E. coli*-25 specific sequence.
[b]*E. coli*-25 gene-specific sequences are shown. For gene deletion mutants, homologous extensions also had the kanamycin primer site: CATATGAATATCCTCCTTA (SEQ ID NO: 22), 3' to the *E. coli*-25 specific sequence.

Competition Assays to Measure Inhibition Phenotype.

Bacterial strains were grown individually overnight in LB. Equal volumes of each competing strain were inoculated into fresh M9 media at a 1:200 dilution, for a final 1:100 dilution of total cells. Cultures were then incubated at 37° C. for 8 to 24 h. It was previously shown that the PDI phenotype does not differ significantly between 8 and 24 h competitions (32). Mixed cultures were then serially diluted, plated on LB supplemented with the appropriate antibiotic to select for each competing strain, and enumerated.

Live/Dead Staining and Flow Cytometry.

Viability assays were conducted using the Live/Dead® BacLight™ Bacterial Viability Kit (L34856, Molecular Probes, Invitrogen, Eugene, Oreg.). Cell cultures were grown in M9 media for six hours at 37° C. and then 1 ml of each culture was collected by centrifugation, washed in 0.85% NaCl, and resuspended in 0.85% NaCl. Cells were then diluted 1:10 in 0.85% NaCl that contained 1.5 μl of 3.34 mM SYTO 9 and 1.5 μl of 30 mM propidium iodide. Samples were incubated at room temperature in the dark for 15 min. Flow cytometry was performed on a FACCalibur flow cytometer (BD Biosciences) and data was analyzed using FCS Express software (De Novo software, Thornton, Ontario, Canada). Initial parameters were established by analyzing cell suspensions with known live- and dead-cell populations. These bacterial suspensions were prepared as follows: cells were grown in M9 minimal media to late-log phase and 1 ml aliquots of the cultures were collected by centrifugation, washed in 0.85% NaCl, and resuspended in either 0.85% NaCl (live portion) or 70% isopropyl alcohol (dead portion). Samples were incubated at room temperature for 30 min, then processed and analyzed by flow cytometry as described above. Ratios of live to dead cells used for the standard were (live: dead): 0:100, 50:50, and 100:0. Gates specific to our *E. coli* (based on side and forward light scatter) were used to collect data on 50,000 cell events. Green versus red fluorescence was measured to distinguish between SYTO 9 stained live cells and propidium iodide-SYTO 9 stained dead cells. Nonspecific signal was excluded at the time of data acquisition.

Sequencing and Analysis.

Genomic extractions of *E. coli*-25, *E. coli*-82, and *E. coli*-264 were prepared using the DNeasy Blood & Tissue kit (Qiagen, Valencia, Calif.) according to the manufacturer's instructions. Sequencing was conducted at the Genomics Core Lab at Washington State University using a Roche 454 FLX Titanium Genome Sequencer to a depth of 24× represented by 399,076 reads. Sequences were assembled using Newbler (version 2.5.3). Annotation employed Glimmer version 3.02 for gene calling, and then the data was piped into CLC Genomics Workbench (CLC Bio, Cambridge, Mass.) where the resulting genes were screened against the current BLAST, SignalP and Pfam databases for functional predictions. The annotated sequence has been deposited in GenBank under (note: sequence submitted, accession number pending).

Site-Directed Gene Deletion.

Gene-specific knockouts were generated using the methods described by Datsenko and Wanner (5). Briefly, the gene of interest was replaced with a PCR-generated kanamycin resistance marker. PCR primers were designed to amplify the kanamycin resistance gene from the template plasmid pKD4. Each primer incorporated 36-50 nt of the region flanking the gene of interest (Table 1). PCR products were column purified (Qiagen, Valencia, Calif.), digested overnight at 37° C. with DpnI (New England Biolabs. Ipswich, Mass.), purified again, and suspended in 30 μl 10 mM Tris, pH 8.0. *E. coli*-25 carrying the λ Red plasmid pKD46 ($Amp^R$) were grown in SOB (2% bactotryptone, 0.5% yeast extract, 10 mM NaCl, 2.5 mM KCl, 10 mM $MgCl_2$, 10 mM $MgSO_4$) with 1 mM L-arabinose at 30° C. to an $OD_{600}$ of ~0.6. The cells were then made electrocompetent by washing twice with ice-cold water, once with 10% glycerol, and concentrating the cells 100-fold in 10% glycerol. Electrocompetent cells (50 μl) were pulsed with ~100 ng of PCR product using the Gene Pulsar 1 (Bio-Rad, Hercules, Calif.). SOC media (12) was immediately added to the cells that were then incubated 2 h at 30° C. Cells were plated on LB with kanamycin and incubated overnight at 30° C. to select for transformants. PCR amplification using primers within the kanamycin resistance gene combined with genomic primers adjacent to the sequence of interest were used to verify that the resistance cassette integrated at the desired location.

Complementation of mcpI Knockout.

A pET100 TOPO® vector (Invitrogen, Grand Island, N.Y.) was used for inducible expression of the putative immunity gene. This gene was PCR amplified from *E. coli*-25 using primers that produce a 3' single-stranded overhang identical to the 5' end of the pET100 vector, allowing directional joining of our gene of interest and the vector. Ligation and transformation was conducted according to the instructions of the Champion™ pET Directional TOPO® Expression kit. Briefly, 2 μl of PCR product was added to 1 μl Salt Solution (provided in kit), 1 μl TOPO vector, and 2 μl sterile water. This reaction incubated at room temperature for 25 min and then was placed on ice for 30 min. An aliquot (3 μl) was added into 50 μl chemically competent Top10 *E. coli* and incubated on ice for 2 min. Cells were heat shocked for 30 sec at 42° C. then transferred to ice. SOC media (250 μl) was added and the cells were incubated 1 h at 37° C. Cells were then plated on LB agar containing ampicillin and incubated overnight at 37° C. Transformants were screened by PCR using the universal T7 forward and reverse primers to identify clones containing the pET100 vector with an insert. Five transformants were selected for sequencing to verify they contained the correct insert. Plasmid was then isolated using the PureYield™ Plasmid Miniprep System (Promega. Madison, Wis.) and transferred to a host cell by electroporation as described above. Transformants were selected by their growth on LB with ampicillin.

Transforming *E. coli*-4 with the PDI Plasmid.

The pPDIΔtraM plasmid was purified using the MiniPrep Express™ Matrix (MP Biomedicals, Solon, Ohio). *E. coli*-4 was then made electrocompetent and transformed (as described above for the gene deletion mutants) with pPDIΔtraM. Successful transformants were selected on LB with kanamycin and PCR verified for the presence of the PDI region.

Plasmid Mating Experiments.

*E. coli*-25ΔmcpM and *E. coli* K12 were grown overnight in LB media with kanamycin or nalidixic acid, respectively. Equal amounts of plasmid-bearing strain *E. coli*-25ΔmcpM were mixed with non-plasmid-bearing *E. coli* K12 and centrifuged for 3 min at 16,000×g. The cells were washed and concentrated 100-fold in 10 mM $MgSO_4$. Cell suspensions were then pipetted onto a nitrocellulose membrane placed on a non-selective LB-agar plate. Following 24 h incubation at 30° C., the cells were resuspended in sterile PBS and dilutions plated on LB-agar containing nalidixic acid and/or kanamycin. The conjugation efficiency was calculated by dividing the CFU of transconjugants by the CFU of donor cells. Plasmid profiles were prepared for a subset of transconjugants to confirm the presence of plasmid. Profiles were conducted as described by Kado and Liu (14). The same experiments, using kanamycin and tetracycline for selection, were then repeated using the K12 pPDIΔmcpM transconjugant and *E. coli*-6 to determine whether the plasmid is self-mobilizable.

RNA Isolation, First-Strand cDNA Synthesis, and microcin RT-qPCR.

*E. coli*-25 encoding McpM was inoculated into 5 ml M9 minimal media containing tetracycline and incubated overnight at 37° C. One ml of overnight culture was inoculated into 300 ml of room temperature M9 media and incubated at 37° C. Aliquots containing approximately $10^8$-$10^9$ cells were removed immediately after inoculation (0 h), and 2 h, 4 it, 6 h, 8 h, 10 h, 12 h, and 24 h post-inoculation. Cells were pelleted by centrifugation at 4° C. and total RNA was isolated and DNase treated using RiboPure-bacteria kit (Ambion) according to manufacturer instructions. RNA concentrations were determined using a NanoDrop ND-1000 spectrophotometer. RNA samples from a given time course experiment were diluted to the same concentration as the least concentrated sample. To assess DNA contamination in RNA samples prior to cDNA synthesis and expression analysis, equivalent RNA concentrations to be used in the corresponding cDNA RT-qPCR reactions were run under identical conditions used for RT-qPCR analysis using polymerase sigma subunit rpoD primers (Table 1). RNA samples with cycle threshold (Ct) values less than 37.5 cycles were again treated with DNase and Ct values reanalyzed prior to cDNA synthesis. First-strand cDNA synthesis was completed using 8 μl of RNA (2-20 ng/μl), random hexamers and SuperScript III reverse transcriptase (Invitrogen) in a final reaction volume of 20 μl according to manufacturer instructions. To verify the specificity of the mcpM primers (Table 1), a single PCR product of the correct size (213 bp) was detected in $PDI^+$ strains but not in $PDI^-$ strains when analyzed on agarose gels. rpoD primers, described above, amplified a single PCR product of the correct size (336 bp) when analyzed on agarose gels from all $PDI^+$ and $PDI^-$ *E. coli* strains tested. The amplification efficiency of primer sets was then determined using plasmid DNA encoding their respective targets under identical conditions used for RT-qPCR.

All RT-qPCR reactions were performed as a single-plex reaction in triplicate in 96-well plates. Positive controls and no template controls were included in duplicate for each primer set. Each reaction was performed using 2 μl of cDNA, 500 nM final concentration per primer, and SsoFastEva Green Supermix (Bio-Rad) in a final volume of 20 μl. All PCR reactions were performed on a CFX96 Real-Time PCR Detection System with version 2.1 software (Bio-Rad) with the following cycling conditions: 95° C. for 30 s, 40 cycles of 95° C. for 1 s, 55° C. for 5 s, and 72° C. for 15 s. Normalized (ΔΔCt) microcin expression was automatically computed using the Bio-Rad CFX Manager Software version 2.1 using rpoD as the reference gene.

Example 2

PDI is Effective Against a Broad Range of *E. coli*

In this Example, PDI was shown to be effective against a broad range of *E. coli*. Because *E. coli* O157:H7 is represented by a diversity of genetic types (33) we first determined if the PDI phenotype was effective against the representative panel of strains. Strains representing bovine-biased and clinical-biased genotypes (33) from both the U.S. and New Zealand were highly susceptible to the PDI phenotype with an average reduction >5 log compared to the population for their respective monocultures (FIG. 1). Three strains of *E. coli* O26 were also tested, and similar reductions were found in population numbers (FIG. 1).

Example 3

Live/Dead Staining Indicated that PDI is Bactericidal

In this example, Live/dead staining indicated that PD is bactericidal. Although susceptible cells show a substantial reduction in their CFU/ml following competition with $PDI^+$ strains, it was not clear if the effect is bacteriostatic or bactericidal. Live/dead staining was used in conjunction with flow-cytometry to address this question using *E. coli*-25 and *E. coli O*157:H7 Sakai in mono- or co-culture. The percent of dead cells detected from the two mono-cultures was 0.50±0.06% and 0.11±0.01%, respectively (mean±SEM). When co-cultured for six hours the percent of dead cells increased to 1.27±0.09% consistent with killing of *E. coli O*157:H7 Sakai. When this susceptible strain was co-cultured with a $PDI^-$ strain (*E. coli*-6), the percentage of dead cells was 0.33±0.03%. These results, which were based on 3 independently replicated assays, indicate that PDT functions by killing susceptible cells.

Example 4

The Microcin-Encoding Gene Cluster was Identified

In this example, the microcin-encoding gene cluster was identified. In addition to the two PDI$^+$ strains, *E. coli*-82 was identified from earlier work (16) as genetically similar (no differences) to *E. coli*-25 based on Xba-I macro-restriction, pulsed-field gel electrophoresis (PFGE) profile (unpublished data). Despite having a comparable genetic profile. *E. coli*-82 does not express the PDI phenotype. Genome sequencing of these two strains allowed an in-depth comparison that identified one relatively large region of sequence difference that was located on a large plasmid in *E. coli*-25. Although previous work using a different method did not detect the presence of plasmids in *E. coli*-25 (32), these results were verified by plasmid purification (14) and subsequent Southern analysis probing for mcpA (data not shown). PCR amplification of the PDI locus (primers available in Table 1) confirmed this region is present in the PDI$^+$ strains *E. coli*-25 and *E. coli*-264, but not the PDI$^+$ strains *E. coli*-6, *E. coli*-82, or *E. coli*-186.

Figure 2:
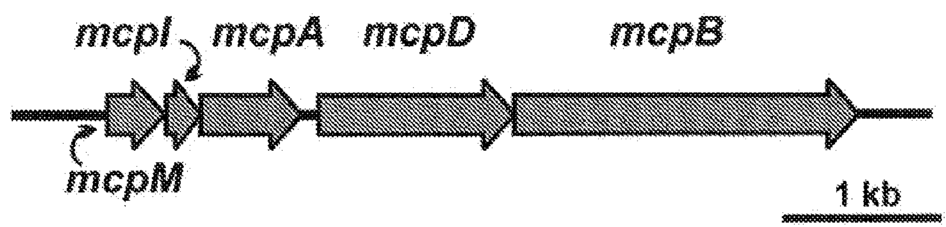
FIG. 2. Schematic of the putative PDI sequence (~5 kb). Whole genome sequencing identified a large plasmid containing a unique region that is present in PDI$^+$ strains but not PDI$^-$ strains (GenBank accession JQ901381) (SEQ ID NO:). Bioinformatics identified five open reading frames putatively corresponding to genes for microcin synthesis (mcpM and mcpA), immunity (mcpI), and export (mcpD and mcpB).

The *E. coli*-25 IncI1 microcin-containing plasmid is 98,809 bp with a G+C content of 49% and a coding density of 88%. Annotation of the 132 coding sequences revealed that most of the plasmid content is devoted to genes involved in transfer, including a Ira system and a pil system, or encodes proteins of unknown function. The novel region of interest is a locus of approximately 4,800 bp that encodes five genes (FIG. 2). Two genes, which we have designated mcpB and mcpD, encode homologs of HlyB and HlyD that are known to be the structural components of a microcin transfer system along with chromosomally encoded tolC (7, 10, 18, 26). McpA, which contains a CaaX protease domain (PF02517), is thought to be the "activity" protein that processes the microcin, encoded by mcpM, to its mature form prior to transfer from the cell. mcpI likely encodes an immunity protein. This novel sequence was also found in a recent GenBank submission of *E. coli* DEC10F (Accession AIGU01000076; version: AIGU01000076.1 GI:378122919; incorporated by reference herein in its entirety).

Example 5

Knockout Mutations from *E. coli*-25 Blocked PDI

Figure 3A:
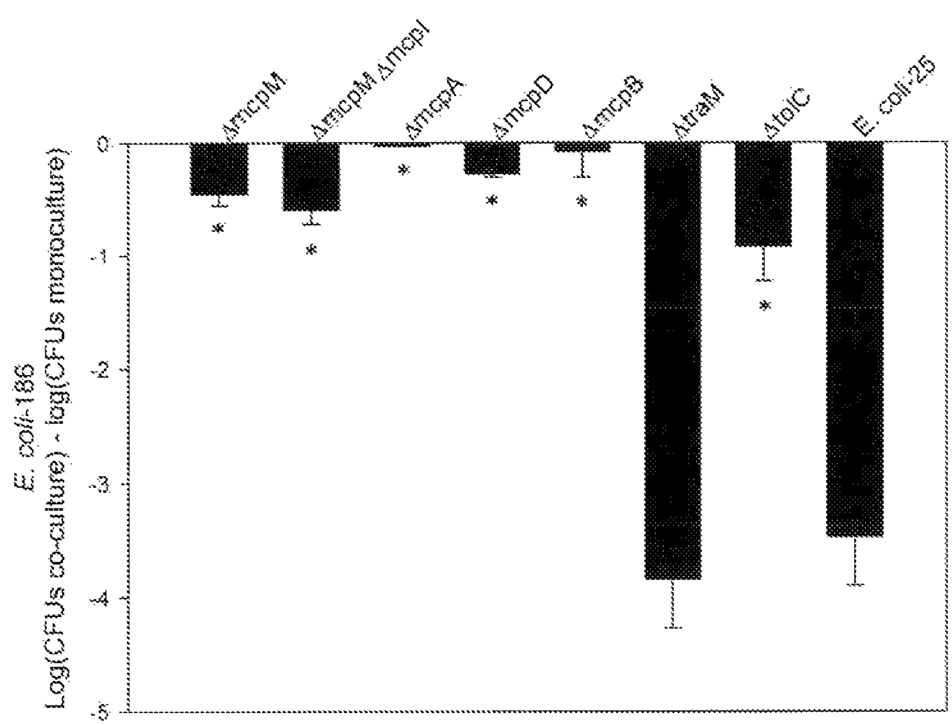
FIGS. 3A-B. Targeted gene deletion results in the loss of the PDI phenotype. A. CFUs of PDI$^+$ *E. coli*-186 following co-culture with wild-type *E. coli*-25 or *E. coli*-25 knockout mutants. Results are expressed as the difference in CFUs of the sensitive strain grown in co-culture and monoculture. B. Competitions with PDI$^+$ *E. coli*-264 indicate which knockout mutants no longer exhibit immunity to PDI. Immunity to PDI is restored in the mcpI complemented clone. Results are expressed as the difference of log CFUs during co-culture and individual culture. Experiments were conducted in triplicate with error bars representing the standard error of the mean. *, statistically significant ANOVA (p-value<0.01 with Dunnett's upper one-sided multiple-comparison test with control).
Figure 3B:
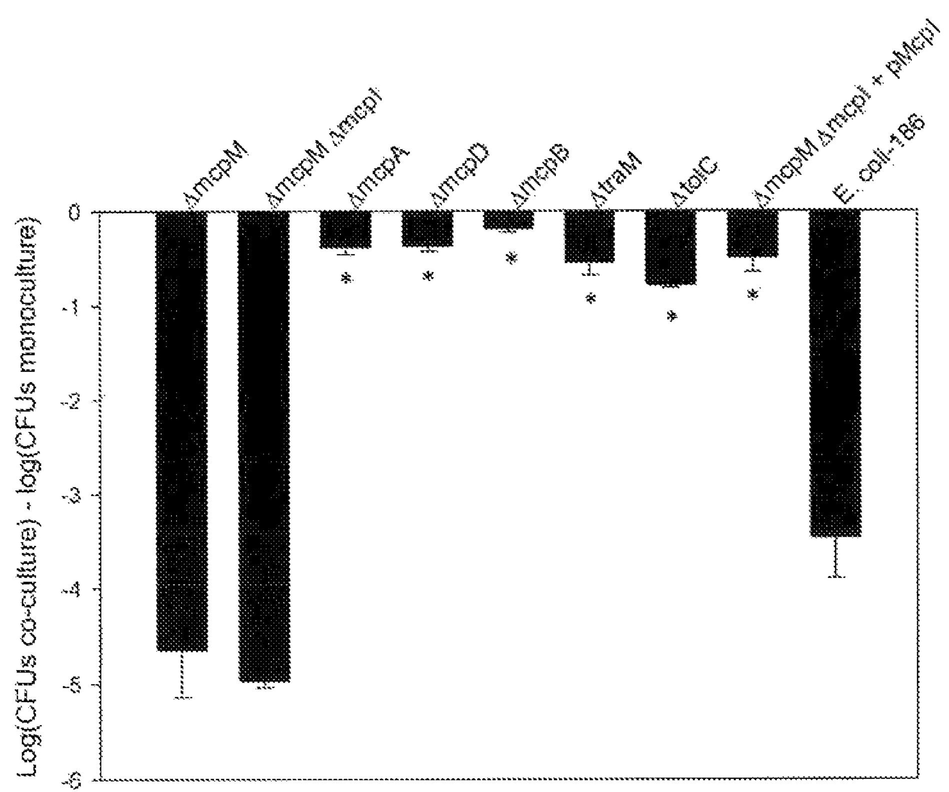

This example shows that knockout mutations from *E. coli*-25 blocked PDI. Four of the five putative microcin genes (FIG. 2) were individually knocked out in *E. coli*-25 to analyze their role in PDI. The mcpI gene knockout was constructed as a double knockout, ΔmcpM ΔmcpI. Each region of interest was replaced with a kanamycin resistant cassette and verified by PCR for the correct insertion site. Subsequently each knockout mutant was put into competition with the PDI$^+$ *E. coli*-186 to determine whether the deletion affected the PDI phenotype. CFU counts following co-culture in M9 minimal media showed that *E. coli*-186 was greatly inhibited by *E. coli*-25 but was no longer inhibited by the ΔmcpD, ΔmcpB, ΔmcpM, ΔmcpMΔmcpI, and ΔmcpA mutants (FIG. 3A). Conversely, each mutant was also competed with *E. coli*-264 to determine how each knockout affected immunity to PDI (FIG. 3B). Only the ΔmcpM and ΔmcpMΔmcpI strains became susceptible to PDI indicating that the other knockout strains retained immunity. Immunity was fully restored when mcpI was complemented back into the ΔmcpMΔmcpI strain, verifying that this gene is required for resistance to killing by PDI$^+$ strains (FIG. 3B). Expression of mcpI in a PDI$^+$ strain does not confer immunity, indicating this gene alone is insufficient to prevent inhibition from the microcin (data not shown).

Class II microcins are typically secreted by a T1SS and the presence of the putative ABC transporter and membrane-fusion genes, mcpB and mcpD, is consistent with this structure in *E. coli*-25. These secretion systems require co-expression of a chromosomally encoded TolC protein on the cell surface (7, 10, 18, 26). Consequently, a ΔtolC strain was constructed and this disrupted the ability of *E. coli*-25 to inhibit *E. coli*-186 (FIG. 3A) but it did not influence immunity (FIG. 3B). These results are consistent with the requirement for a T1SS for PDI function. To verify that the gene knockout procedure was not producing artifacts, a gene deletion in an unrelated region of the plasmid was also generated. As expected, deleting traM did not affect inhibition or immunity (FIG. 3).

Example 6

Transferring the PDI Plasmid to a Non-Inhibitor *E. coli* Conferred the Inhibitory Phenotype This example shows that transferring the PDI plasmid to a non-inhibitor *E. coli* conferred the inhibitory phenotype. Although the above knockout mutants verified that the genes involved with PDI had been identified, it was desirable to confirm from the mutants that all the genes unique to PDI were included on pPDI. Generating the traM mutant in *E. coli*-25 provided a selectable marker on pPDI that did not interfere with the PDI phenotype (see above). Following transformation with pPDIΔtraM, *E. coli*-4 acquired the ability to inhibit susceptible strains, and immunity to inhibition by *E. coli*-264 (Table 2).

Table 2 shows competition results of wild-type *E. coli*-4 and *E. coli*-4 carrying the PDI plasmid verifies the PDI genes are present on the plasmid. CFUs of PDI$^+$ *E. coli*-186 following co-culture with wild-type *E. coli*-4 or *E. coli*-4+pPDI verifies the plasmid confers the inhibitory phenotype. Immunity to PDI is also maintained on the plasmid, as indicated by the ability of *E. coli*-4+pPDI to survive co-culture with the PDI$^+$ strain *E. coli*-264. Results are expressed as log CFUs/ml±the SEM of 3 replicates.

This data indicates that all the PDT-specific genes are present on pPDI. Nevertheless, there is a possibility that other chromosomally-encoded genes common to *E. coli*-25 and *E. coli*-264 are involved with PDI expression or function.

TABLE 2

Competition results of wild-type *E. coli*-4 and *E. coli*-4 carrying the PDI plasmid verified the PDI genes are present on the plasmid.

| Competition | $Log_{10}$(CFU)/ml | |
|---|---|---|
| | *E. coli*-4 | Competitor |
| *E. coli*-4 (PDI) | | |
| vs. *E. coli*-186 (PDI$^-$) | 8.83 ± 0.05 | 8.64 ± 0.06 |
| vs. *E. coli*-264 (PDI$^+$) | 4.70 ± 0.28 | 9.14 ± 0.02 |
| *E. coli*-4 + pPDI | | |
| vs. *E. coli*-186 (PDI$^-$) | 9.18 ± 0.06 | 4.03 ± 0.61 |
| vs. *E. coli*-264 (PDI$^+$) | 8.88 ± 0.03 | 8.76 ± 0.02 |

Example 7

The PDI ΔmcpM Plasmid was Shown to be Self-Transmissible

This example shows that the PDI ΔmcpM plasmid is self-transmissible. Filter mating experiments between the ΔmcpM mutant and *E. coli* K12 showed the PDI plasmid is mobile with a conjugation efficiency ranging between $4.81\times10^{-6}$ and $3.66\times10^{-6}$. Plasmid profiles of K12 $Kan^R$ verified the presence of a single plasmid of ~100 Kb, consistent with the PD) plasmid. Another series of conjugation experiments between the K12 transformants and *E. coli*-6 confirmed that the plasmid is self-transmissible. Using this assay conjugation of the PDI plasmid was not detected when there was a functional microcin system, presumably because recipient cells are killed.

Example 8

The Kinetics of the Expression of mcpM were Determined

This example shows the kinetics of the expression of mcpM. Expression of the PDI phenotype has been observed throughout log-phase growth, but this function appears to subside when cells enter stationary phase (32). This earlier work was limited by the analytic sensitivity of the phenotypic assay and thus to better describe the kinetics of microcin expression we employed a quantitative PCR assay. RT-qPCR data confirmed that expression of the microcin increases rapidly during the log-phase growth and drops off rapidly in stationary phase (FIG. 4).

Example 9 cDNA Sequences and Protein Sequences for mcpM, mcpI, mcpA, mcpD, and mcpB were Determined This example shows the cDNA sequences and protein sequences encoded by mcpM, mcpI, mcpA, mcpD, and mcpB:

cDNA sequence and protein sequence for mcpM (SEQ ID NOS: 23 and 24)

ATGGCAAATATAAGAGAATTAACTTTAGATGAGATAACGCTTGTCAGCGGAGGA

ACAGCAACTTTGAAGGTGGCCCCCGTAATGACCGTTCCAGTGGGGCTCGTAACTC

ACTGGGTCGAAACGCACCAACTCATATTTATAGTGATCCAAGCACTGTAAAATGC

GCTAACGCTGTATTTAGTGGAATGATTGGTGGTGCGATCAAAGGAGGTCCCATAG

GAATGGCAAGAGGTACCATTGGTGGAGCCGTTGTTGGTCAATGTCTCTCAGATCA

TGGTAGTGGAAATGGAAGTGGTAACAGAGGAAGTTCCAGTAGTTGTTCAGGTAA

TAATGTTGGCGGAACATGTAACCGATAA

M A N I R E L T L D E I T L V S G G N A N S N F E G G P R N D R S S G A R N S L G R

N A P T H I Y S D P S T V K C A N A V F S G M I G G A I K G G P I G M A R G T I G G

A V V G Q C L S D H G S G N R G S S S S C S G N N V G G T C N R Stop cDNA sequence and protein sequence for mcpI (SEQ ID NOS: 25 and 26)

ATGGAGGGCGCTACTATGTTTATTAAATTACTTTCCTTTATATGTGGTTTGTTACT

GGGATTTGCACTATTGAGTGGCTCCTCTGTTATTGATTTATACTGGTTTTCACTAC

CTTCCGAGTTTTCAAAGATTGTAGTCATGCTGATCACTCTTTTTTCCACGGCAAGA

TTCATGGACTATATCATAGAAAAAATAAGAACAATCTCCGCGAAATAG

M E G A T M F I K L L S F I C G L L L G F A L L S G S S V I D L Y W F S L P S E F S F K

I V V M L I T L F S T A R F M D Y I I E K I R T I S A K Stop cDNA sequence and protein sequence for mcpA (SEQ ID NOS: 27 and 28)

ATGAATGATAACATATATAAATATAGTAAAGATATAATGCGATAGCGtTTCTTCTAC

TTGTTGTTATATCAACAGTTGTGATATTCACACCGGCATTCACCATACAATATATT

GGTTTGGATCTGGCATTTTCCTTTGTCTTTATTACTGAAATTTTAATGTCAACTTC

ATTTTATATTTTTTACTTAAGAAGAATACCAGGTTGTAAAATCACCATAAAGACA

AATGCGAAAACATTAAAGCTATTAGTAATATCATTTGCTGTGATTGCTCTCATGC

AACTGCTTATTTTTGCTTATAGAGACAATTTGAACAATAGTGAATCAACTTCACTT

AATTGGATTGAAATATTTATACTGGTCCTGACAGTTCCGTATTATGAAGAAATTG

-continued

TTTACCGAACATGTCTATTCGGTCTTCTATGTACGACTTATaAAAAAGAATTATTT

AcCCCCTGCGTGTGTACATCTTTAtTTTTCTGCCTGATGCATCCGCAGTATTATAAT

GTGGCTGATCAAATTATTCTGTTTATTATGTCAATGTTATTGTTGAATATAAGGAT

TTGCAGTAAGGGGATTTTCTATCCAATGCTGTTACATGCGGGAATAAACGGCTTT

GTTATATTGTTAAATATATTATAG

M N D N I Y K Y S K D N A I A F L L L V V I S T V V I F T P A F T I Q Y I G L D L A F

S F V F I T E I L M S T S F Y I F Y L R R I P G C K I T I K T N A K T L K L L V I S F A

V I A L M Q L L I F A Y R D N L N N S E S T S L N W I E I F I L V L T V P Y Y E E I V

Y R T C L F G L L C T T Y K K E L F T P C V C T S L F F C L M H P Q Y Y N V A D Q I

I L F I M S M L L L N I R I C S K G I F Y P M L L H A G I N G F V I L L N I L Stop cDNA sequence and protein sequence for mcpD (SEQ ID NOS: 29 and 30)

ATGAATATATTCAGAAGTGAAGCAATAGAACATCATAATGACACTGAATATGGT

GACATTATTTTACCAACATCATTTAGCCTATCCGTATGTGCAACAGTTACATTATT

CATTATGTTAAGTCTGACTGTATTCATATATTACGGTAGCTATACAAGGAAAGCG

CATCTTACAGGTATCGTCATGCCCTCATCAGGACTGGTAAAAATAATTCCTCAAT

ATGCAGGATATGTAACACAACTGACTGTATCCGAAGGAGAACACGTAACTGCAG

GGACACAACTCTATCATATAAGTGGAGAACATTATAACGGTAACGGAACTGGCA

CATTAGCAACGATGAGTATTTCCCTGAAGACTCAGTATATTATGTTGGCCTCCCA

GCAATCCTTTGAGTCGCGAGATAATAGTCAACAACAGGAAGCCATACGGCAAAG

GATGATATCACTTGAGCCGCAAATAAGAAGTGCAGAACAAAGACTTCAGCTTGC

TGAACGTCAGGCAGAACTGGCTATATCCGTCATGGAACGCTATAAAAAATTGGC

TGGTACGCATTATGTGTCAGATATCGAATTCCAACAGAAACAAATTGATGTTTCT

GCCGCTCAACAAAACGTTGAAGATCAGCGTCAGGGGCTTCTCCAGTTACATACTG

CAATGGACACAGCCAAAGATGAACTAAATCATCTTATTGTTCAGGGGAAAAGCC

GTAAAGCAGAACTCGACAGACAATTGCAGGTGCTAAAACAACAACAGGATGAAC

TCGCCGGACAAGAAAAAATTTACACTGAGGGCTCCAGTATCCGGGACTATTGCTGC

TGTACTGATCAAACAGGGGCAGTCTGTGAAAGCATCTGAACCGGTCATGACTCTC

ATTCCCGATAATGCTCATTTACAAATTGAGCTTTATGCTACCAGCCAGAAAGCCG

GTTTTATCCGACCAGGTCAACGGGTATCTCTGAAGTTTTCGGCCTTCCCTTATCAG

AAATTTGGTATCCAGTACGGCACAATTCGTAAAATCAGTCATACGACTCTGGCTC

CTTCCGACTTATTACCAGTTTCACCCGTCACATGGAAAGAAAACGAAGGGCATTA

TCGCGTTATTGTTGAACCTGAAAATACATTTATATTTGCATACGGAAAAAAAGAA

CCGCTAAGACCAGGCATGACTCTGGAAGGAGACGTCAACCTTGATACTCGTCATT

TATGGGAATGGCTGACAGAGCCCCTATGGAGCATGAAAGGAAATCTGTAA

M N I F R S E A I E H H N D T E Y G D I I L P T S F S L S V C A T V T L F I M L S L T

V F I Y Y G S Y T R K A H L T G I V M P S S G L V K I I P Q Y A G Y V T Q L T V S E

G E H V T A G T Q L Y H I S G E H Y N G N G T G T L A T M S I S L K T Q Y I M L A

S Q Q S F E S R D N S Q Q Q E A I R Q R M I S L E P Q I R S A E Q R L Q L A E R Q A

E L A I S V M E R Y K K L A G T H Y V S D I E F Q Q K Q I D V S A A Q Q N V E D Q

R Q G L L Q L H T A M D T A K D E L N H L I V Q G K S R K A E L D R Q L Q V L K

-continued

Q Q Q D E L A G Q E K F T L R P V S G T I A A V L I K Q G Q S V K A S E P V M T

L I P D N A H L Q I E L Y A T S Q K A G F I R P G Q R V S L K F S A F P Y Q K F G I Q

Y G T I R K I S H T T L A P S D L L P V S P V T W K E N E G H Y R V I V E P E N T F I

F A Y G K K E P L R P G M T L E G D V N L D T R H L W E W L T E P L W S M K G N

L Stop cDNA sequence and protein sequence for mcpB (SEQ ID NOS: 31 and 32)

ATGGAATCAATAAACTGGAAAGTAAGGAAACAACTACCCGTTATCCGTCAAACC

GAATCAGCTGAATGCGGTCTGGCGTGTCTGGCTATGATTGCCTGCTGGCATGGAC

TGAAAACAGATTTATCGACATTACGGGAACGTTTCAATATAGGTATTCAGGGAAT

GACGCTACAAAGGTTGATCGAATGTGCAGCGTCCATCCATTTATCATCACGTGCA

GTTCGTCTGGAACCCGAAGATCTGAGTGTCTTAATCTTCCATCTATTCTGCACTG

GGATATGAACCATTTCGTCGTTCTCCATAAAGTTCGGGGAAACCGGTTATACATC

CATGATCCGGACAGAGGAAAAATTACAATAAGTCTGTTGGACGCAGGTAAGCAT

TTTACAGGAGTGGCACTGGAATTAACTCCAGCCAGTGATTTCACCCCCCGGAACG

AGAGAAAAAAATCCACCTGCGTCAACTGACAGGGAAAACCCCGGGGCTTTTAGC

ATCAATGACaAAAATTATTATTTTTGCTCTGGCCCTGAGATTCTGGCTTTAGGTG

GTCCACTTCTTAATCAACTGGTAATTGATGAAGTTCTGGTCGCAGCAGACAGAAG

TCTATTGTATGTCATTATAGTGGCACTACTGTTGTTATCACTCATACAATTATTAC

TCTCCCTAGCACGACAATGGGCAACGATCAGTTTATCCGTCAATTTTAACATGCA

ATGGACTGCCAGAGTTTTCCATCATCTTGTAAGACTCCCTCTTGCATGGTTCGATG

CCCGAAGTAAAGGAAGTATTAAGCCCGTTTTGAAGCAGTAGATATAATCCAGC

AGGCGCTGACAACGCAGGTTCTTGAAGGCATTCTGGATATGCTACTTATTGTGAC

TGCTCTTTGCATGATGCTGTTGTATAGCCCAGGAATGACATTAATCGCAGTAATT

GCAGCTATTATATATGGCGCACTGAGAGCATTGTGGTATCCGGCTTTACGGCAAT

CTGTTGAAGATGTCTGGGATGCAGGAACTAAGGAGTCGGGGCATTTTCTCGAAA

CCCTTAACGGCATTCAGAGTCTGAGAATCAACGGTGTAACTATTCACAGAGAAG

CGGCCTGGCTGAACCTCAACGTTACCCGCAGAAACACACAGCTACGCCAGAATC

GTTTACAAATGAGCTATGAACTGACGCATACACTGACGGAAAGTGTAGTTTCAGC

CATTATTTTGTGGCAGGGAGCAGTAGAAGTGCTGGATGGGACATTTACCGTGGGT

ATGTTGGTTGCTTACTTATCCTATCAGATGCGTTTTTCATCCAGTATAAGCAATCT

GACTGATAACTTTTTTTCCTGGCGCATGCTTGATGTTTATAACGAGAGACTTGCCG

ATATTGTGCTAACACCACAGGAAGGTCACCAGAATCAGCACCATTGGGCAAACC

ATAATGAAACAATATCTGCAAGCCAGTACAGAGAACATAAATATGATAATACCC

ATCCACCATTACTTATCGaAAAAATAACATTTAGCCATAAGGGCGCAGATAAACC

CATATTGGATAACGCGTCACTAATGCTCTTTCCTGGAGAAATATTAGCAATAACA

GGTAAATCAGGATGTGGCAAATCAACATTGGTAAAGCTTATTCTTGGAATTCATA

CACCAAGTGAAGGAAGAATTAATGCATTTGGCATACCACATACACATTCTGATTA

TTTTCAGGTTCGTCAACGAATTGGCACTGTATTGCAAGATGACTATCTTTTCAAA

GGTTCTATAGCTGATAATATAATGTTTTTTAGCGAAATTAGAGATCATGAACACA

TGCGTAAATGCGCAAGTCTGGCACTTATAGACAGTGATATTATGGCAATGCCAAT

GGGCTATCAAACATTACTTGGAGAAACCGGAGGGGGACTTTCAGGTGGTCAGAAG

-continued

CAACGTATTCTACTGGCAAGAGCACTGTATAAAAAACCCGGTCTATTATTACTGG

ACGAAGCAACCAGTCATCTTGATGTGGAAAGTGAAATAGAAATAAGCCAGACAT

TACGCCAACTCGGATTCCTGTTCTGTTAATAGCTCATCGACCAGAAACAATAGCA

TCCGCAGACAGAGTTCTATCTGAGAGATGGTCACTTTTCGGAAATAACATATCGA

CCTGCCAGAACTCATAATATAAATAATCACCCCAACAGGAGGTGA

M E S I N W K V R K Q L P V I R Q T E S A E C G L A C L A M I A C W H G L K T D L

S T L R E R F N I G I Q G M T L Q R L I E C A A S I H L S S R A V R L E P E D L R C L

N L P S I L H W D M N H F V V L H K V R G N R L Y I H D P D R G K I T I S L L D A

G K H F T G V A L E L T P A S D F F T P R N E R K K I H L R Q L T G K T P G L L A S

M T K I I I F A L A L E I L A L G G P L L N Q L V I D E V L V A A D R S L L Y V I I V

A L L L L S L I Q L L L S L A R Q W A T I S L S V N F N M Q W T A R V F H H L V R

L P L A W F D A R S K G S I N A R F E A V D I I Q Q A L T T Q V L E G I L D M L L I

V T A L C M M L L Y S P G M T L I A V I A A I I Y G A L R A L W Y P A l R Q S V E

D V W D A G T D E S G H F L E T L N G I Q S L R I N G V T I H R E A A W L N L N V

T R R N T Q L R Q N R L Q M S Y E L T H T L T E S V V S A I I L W Q G A V E V L D

G T F T V G M L V A Y L S Y Q M R F S S S I S N L T D N F F S W R M L D V Y N E R

L A D I V L T P Q E G H Q N Q H H W A N H N E T I S A S Q Y R E H K Y D N T H P P

L L I E K I T F S H K G A D K P I L D N A S L M L F P G E I L A I T G K S G C G K S T

L V K L I L G I H T P S E G R I N A F G I P H T H S K Y F Q V R Q R I G T V L Q D D Y

L F K G S I A D N I M F F S E I R D H E H M R K C A S L A L I D S D I M A M P M G

Y Q T L L G E T G G G L S G G Q K Q R I L L A R A L Y K K P G L L L L D E A T S H

L D V E S E I E I S Q T L R Q L G I P V L L I A H R P E T I A S A D R V L Y L R D G H

F S E I T Y R P A R T H N I N N H P N R R

Example 10

Sequence for Plasmid Containing the Unique 4.8-kb Operon Region that is Present in PDI$^+$ Strains but not PDI$^-$ Strains (GenBank Accession: JQ901381)

This sequence for the plasmid containing the unique 4.8-kb operon region that is present in PDI$^+$ strains but not PDI$^-$ strains was determined (GenBank accession JQ901381) and is presented as SEQ ID NO: 33. The region covering mcpM, mcpI, mcpA, mcpD, and mcpB is presented as SEQ ID NO: 34. Within SEQ ID NO: 34, the nucleotide positions of individual operon components are as follows: mcpM (41253-43442); mcpI (43443-44695); mcpA (44798-45433); mcpD (45438-45654); and mcpB (45663-46026).

REFERENCES FOR BACKGROUND AND EXAMPLES 1-10

1. Aoki, S. K., R. Pamma, A. D. Hernday, J. E. Bickham, B. A. Braaten, and D. A. Low. 2005. Science 309:1245-8.
2. Asensio, C., and J. C. Perez-Diaz, 1976. Biochem Biophys Res Commun 69:7-14.
3. Bullock, J. O., F. S. Cohen, J. R. Dankert, and W. A. Cramer. 1983. J Biol Chem 258:9908-12.
4. Dassanayake, R. P., D. R. Call, A. A. Sawant, N. C. Casavant, (G. C. Weiser, D. P. Knowles, and S. Srikumaran. 2010. Appl Environ Microbiol 76:1008-13.
5. Datsenko, K. A., and B. L. Wanner. 2000. Proc Natl Acad Sci USA 97:6640-5.
6. Duquesne, S., D. Destoumieux-Garzon, J. Peduzzi, and S. Rebuffat. 2007. Nat Prod Rep 24:708-34.
7. Gaggero, C., F. Moreno, and M. Lavina. 1993. J Bacteriol 175:5420-7.
8. Garrido, M. C., M. Herrero, R. Kolter and F. Moreno. 1988. EMBO J 7:1853-62.
9. Gentschev, I., G. Dietrich, and W. Goebel. 2002. Trends Microbiol 10:39-45.
10. Gilson, L., H. K. Mahanty, and R. Kolter. 1990. EMBO J 9:3875-84.
11. Gratia, A. 1925. C. R. Soc. Biol. (Paris) 93:1040-1041.
12. Hanahan, D. 1983. J Mol Biol 166:557-80.
13. Hardy, K. G., G. G. Meynell, J. E. Dowman, and B. G. Spratt. 1973. Mol Gen Genet 125:217-30.
14. Kado, C. I., and S. T. Liu. 1981. J Bacteriol 145:1365-73.
15. Kawamura, T. 1997. Rinsho Byori 45:865-8.
16. Khachatryan, A. R., T. E. Besser, and D. R. Call. 2008. Appl Environ Microbiol 74:391-5.
17. Khachatryan, A. R., D. D. Hancock, T. E. Besser, and D. R. Call. 2006. Appl Environ Microbiol 72:443-8.
18. Lagos, R., M. Baeza, G Corsini, C. Hetz, E. Strahsburger, J. A. Castillo, C. Vergara, and O. Monasterio. 2001. Mol Microbiol 42:229-43.
19. Lederberg. J., and E. L. Tatum. 1946. Nature 158:558.
20. Lemonnier, M., B. R. Levin, T. Romeo, K. Garner, M. R. Baquero, J. Mercante, E. Lemichez, F. Baquero, and J. Blazquez. 2008. Proc Biol Sci 275:3-10.

21. Linton, K. J., and C. F. Higgins. 1998. Mol Microbiol 28:5-13.

22. Lwoff, A., F. Jacob, E. Ritz, and M. Gage. 1952. C R Hebd Seances Acad Sci 234:2308-10.

23. Martinez, M. C., C. Lazdunski, and F. Pattus. 1983. EMBO J 2:1501-7.

24. Nomura, M., and M. Nakamura. 1962. 7:306-9.

25. Ohno-Iwashita, Y., and K. Imahori. 1982. J Biol Chem 257:6446-51.

26. Pons, A. M., F. Delalande, M. Duarte, S. Benoit, I. Lanneluc, S. Sable, A. Van Dorsselaer, and G. Cottenceau. 2004. Chemother 48:505-13.

27. Pugsley, A. P., and S. T. Cole. 1986. J Gen Microbiol 132:2297-307.

28. Reeves, P. 1965. The Bacteriocins. Bacteriol Rev 29:24-45.

29. Riley, M. A., and D. M. Gordon. 1992. J Gen Microbiol 138:1345-52.

30. Riley, M. A., Y. Tan, and J. Wang. 1994. Proc Natl Acad Sci USA 91:11276-80.

31. Riley, M. A., and J. E. Wertz. 2002. Annu Rev Microbiol 56:117-37.

32. Sawant., A. A., N. C. Casavant, D. R. Call, and T. E. Besser. 2011. Appl Environ Microbiol 77:2345-51.

33. Shringi, S., A. Garcia, K. K. Lahmers, K. A. Potter, S. Muthupalani, A. G. Swennes, C. J. Hovde, D. R. Call, J. G Fox, and T. E. Besser. 2012. Infect Immun 80:369-80.

34. Smarda, J. 1962. Experientia 18:271-3.

35. Trueblood, C. E., V. L. Boyartchuk, E. A. Picologlou, D. Rozema, C. D. Poulter, and J. Rine. 2000. Mol Cell Biol 20:4381-92.

36. Wilkens, M., J. E. Villanueva, J. Cofre, J. Chnaiderman, and R. Lagos, 1997. J Bacteriol 179:4789-94.

Example 11

Microcin MccPDI Reduces the Prevalence of Susceptible *Escherichia coli* in Neonatal Calves MccPDI microcin producing *E. coli*-25 or the equivalent knockout strains were co-inoculated into calves with susceptible *E. coli*-186 to investigate the function of MccPDI in vivo. MccPDI-producing *E. coli*-25 out-competed *E. coli*-186 (P=0.003), consistent with MccPDI being responsible for antibiotic resistant *B. coli*-25 competitive advantage in calves. The increasing prevalence of antibiotic resistant bacteria presents a major challenge for both human and animal health. High levels of antimicrobial usage in livestock potentially plays an important role in amplifying and retaining antibiotic resistance genes in bacterial populations (6, 7, 13). Nevertheless, even in the absence of antibiotic use resistant bacteria can persist (2, 5, 8). A previous study showed that *E. coli* strains with resistance to streptomycin, sulfadiazine, and tetracycline (SSuT) were the dominant *E. coli* found in calves at the Washington State University (WSU) dairy (10). Mixtures of these SSuT *E. coli* isolates, including strain *E. coli*-25, demonstrated a fitness advantage in dairy calves and in broth culture over antibiotic susceptible strains (10). The mechanism allowing these strains to dominate in calves was unknown, but was not associated with antimicrobial resistance traits (9). Recently we showed *E. coli*-25 produces the novel microcin, MccPDI, that is responsible for killing susceptible *E. coli* in vitro. MccPDI-production allows *E. coli*-25 to inhibit a diversity of *E. coli*, including olates enterohemorrhagic (EHEC) and enterotoxigenic (ETEC) strains (4, 11). The spectrum of MccPDI activity makes *E. coli*-25 attractive as a probiotic against pathogenic bacteria with potential for prophylactic, therapeutic, and food safety applications. Consequently, we tested the hypothesis that an MccPDI-producing *E. coli*-25ΔtraM strain will limit colonization of dairy calves by the MccPDI-susceptible *E. coli*-186, while MccPDI-knockout strain, *E. coli*-25ΔmcpMΔmcpI would exhibit no selective advantage in vivo (4).

This study was conducted in the large animal isolation facilities at WSU under a WSU Institutional Animal Care and Use Committee approved protocol. Calves inoculated with the same strains were housed in groups when possible. Bulk milk was fed two to three times daily with one feeding containing 1 tbsp. of milk non-antibiotic containing supplement (10). Calves were pre-screened for nalidixic acid-, kanamycin-, and chloramphenicol-resistant *E. coli* using methods described below. If resistant bacteria were detected the calf was not used in the study. Kanamycin- and chloramphenicol-resistant *E. coli*-25 mutants were generated (Table 1) to allow the use of calves that carried either kanamycin or chloramphenicol resistant flora, but did not carry both. Each calf (<3 days old) was orally inoculated with $10^9$ CFU of each competing *E. coli* strain. Inoculum was prepared by pelleting overnight cultures of each strain, resuspending the cells in fresh LB, and mixing the cultures immediately before inoculation. If the inoculated strains were not detected at one day post-inoculation, a second dose was administered on day two. Day one refers to the day following the final inoculation. The trial included two groups of calves with group one (n=4) receiving MccPDI knockout *E. coli*-25ΔmcpMΔmcpI and *E. coli*-186 and group two (n=7) receiving MccPDI-producing *E. coli*-25ΔtraM and *E. coli*-186; chance enrollment of calves with incompatible antibiotic resistant flora led to rejection of more calves from group one.

Figure 5:
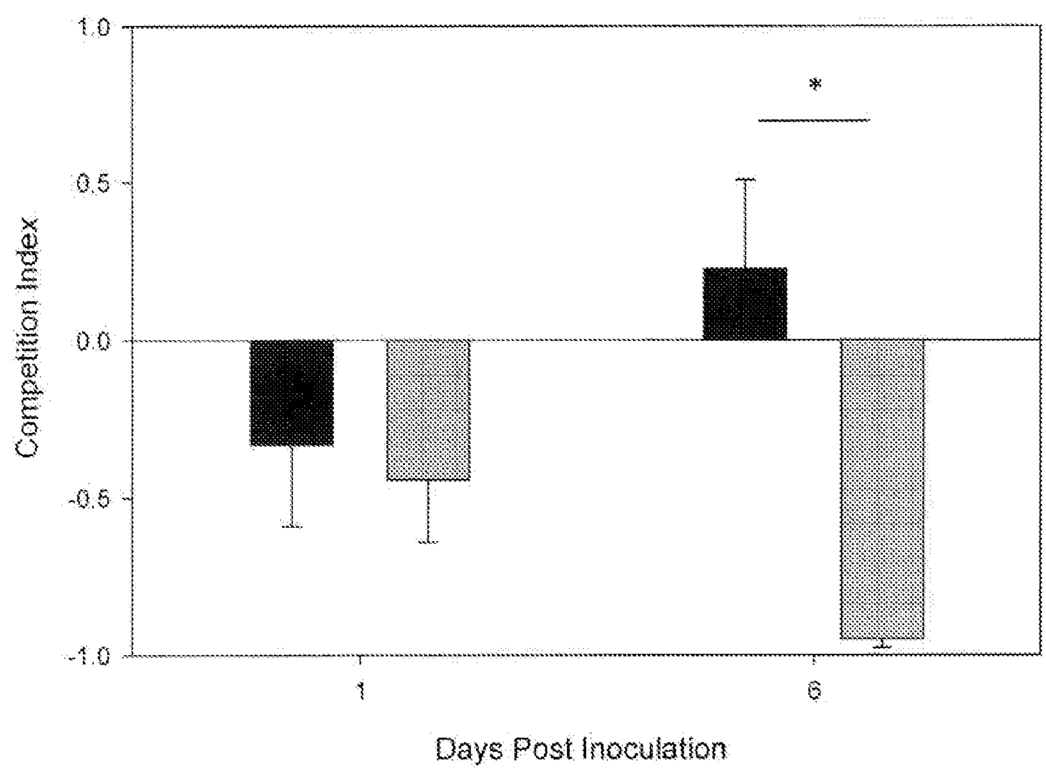
FIG. 5. MccPDI-producing *E. coli*-25 inhibits the growth of susceptible *E. coli*-186 in neonatal calves. A competition index (CI) was calculated as (X−Y)/(X+Y), where X is the CFU of *E. coli*-25ΔmcpMΔmcpI or *E. coli*-25ΔtraM colonies and Y is the CFU of *E. coli*-186 colonies. A CI approaching+1 indicates the *E. coli*-25 mutant is the dominant strain and a CI approaching −1 indicates *E. coli*-186 is dominant. The mean CI for the positive (black bars; *E. coli*-25ΔtraM and *E. coli*-186; n=7)) and negative control (white bars; *E. coli*-25ΔmcpMΔmcpI and *E. coli*-186; n=4) calves on day one and day six. Error bars correspond to the standard error of the mean and the asterisk shows significant difference between MccPDI-producing and non-producing groups (P=0.003).

Fecal samples were collected directly from the rectum of each calf immediately following inoculation (day 0) and each day for six days (10). Within 4 h of collection ten-fold serial dilutions of each sample were prepared in sterile PBS and plated on MacConkey agar to determine total colony forming units (CFUs) of lactose fermenting enteric bacteria with colony morphology consistent with *E. coli*. MacConkey agar supplemented with kanamycin (50 μg/mil) and tetracycline (50 μg/ml), chloramphenicol (34 μg/ml) and tetracycline (50 μg/ml), or nalidixic acid (30 μg/ml) was used to enumerate the test strains present in the fecal samples. A competition index (CI) was calculated to compare the fitness of competing strains (FIG. 5). PCR was used to confirm the identity of the *E. coli*-25 mutants by pairing primers within the resistance cassette (3) with locus-specific primers (Table 3; n=: 368). The putative *E. coli*-186 isolates (n=172) recovered from the fecal samples were confirmed by pulsed-field gel electrophoresis analysis (1).

TABLE 3

| E. coli strains and PCR primer sequences used in this work. | | | |
|---|---|---|---|
| *E. coli* Strain | Genotype/phenotype | Strain-specific primer | Ref. |
| 25ΔmcpMΔmcpI | SSuT$^r$ Chlor$^r$ ΔmcpMΔmcpI PDI$^-$ | mcpM_mcpI fwd:CAAACAACCGATAGGGGAAA (SEQ IN NO: 36) c2: GATCTTCCGTCACAGGTAGG (SEQ IN NO: 37) | This Work |
| 25ΔmcpMΔmcpI | SSuT$^r$ Kan$^r$ ΔmcpMΔmcpI PDI$^-$ | mcpM_mcpI fwd: CAAACAACCGATAGGGGAAA (SEQ IN NO: 38) k2: CGGTGCCCTGAATGAATGAACTGC (SEQ IN NO: 39) | (4) |
| 25ΔtraM | SSuT$^r$ Chlor$^r$ ΔtraM PDI$^+$ | traM fwd: GTTCTGCCATCCTGCGTTAT (SEQ IN NO: 40) c1: TTATACGCAAGGCGACAAGG (SEQ IN NO: 41) | This work |
| 25ΔtraM | SSuT$^r$ Kan$^r$ ΔtraM PDI$^+$ | traM fwd: GTTCTGCCATCCTGCGTTAT (SEQ IN NO: 42) k1: CAGTCATAGCCGAATAGCCT (SEQ IN NO: 43) | (4) |
| 186 | Wild-type; Nal$^r$ PDI$^-$ | | (11) |
| O157:H7 6-E12057 | Wild-type; Nal$^r$ Cip$^r$ | rfb fwd: AAGATTGCGCTGAAGCCTTT (SEQ IN NO: 36) rfb rvs: CATTGGCATCGRGTGGACAG (SEQ IN NO: 36) | (12) |

At six days post-inoculation calves were euthanized and five to ten centimeter lengths of the cecum, spiral colon, descending colon, and rectal-anal junction (RAJ) were collected. All fecal matter was removed by rinsing the tissue in sterile PBS. A 6 mm sterile biopsy punch was used to collect a sample and make a 1:10 dilution (sa/vol) in PBS. The tissue was homogenized, serially diluted, and plated onto MacConkey agar supplemented with antibiotics.

A previous study with *E. coli*-25 indicated the microcin-producing strain *E. coli*-25ΔtraM should have a distinct advantage over the susceptible strain *E. coli*-186 (10). As expected, by day six, *E. coli*-25ΔtraM dominated *E. coli*-186 (CI=0.22, P=0.003; FIG. 1). In contrast, the microcin-knockout strain *E. coli*-25ΔmcpMΔmcpI was significantly less fit than *E. coli*-186 (CI=−0.95; FIG. 5). Notably, different treatment outcomes were asymmetric with the CI for *E. coli*-25ΔtraM (0.22) being a smaller magnitude than the competition index for *E. coli*-25ΔmcpMΔmcpI (~0.95). This could possibly be explained by the presence of native MccPDI-expressing strains that would also compete with *E. coli*-25ΔtraM while enhancing inhibition of the susceptible *E. coli*-25ΔmcpMΔmcpI.

Figure 6:
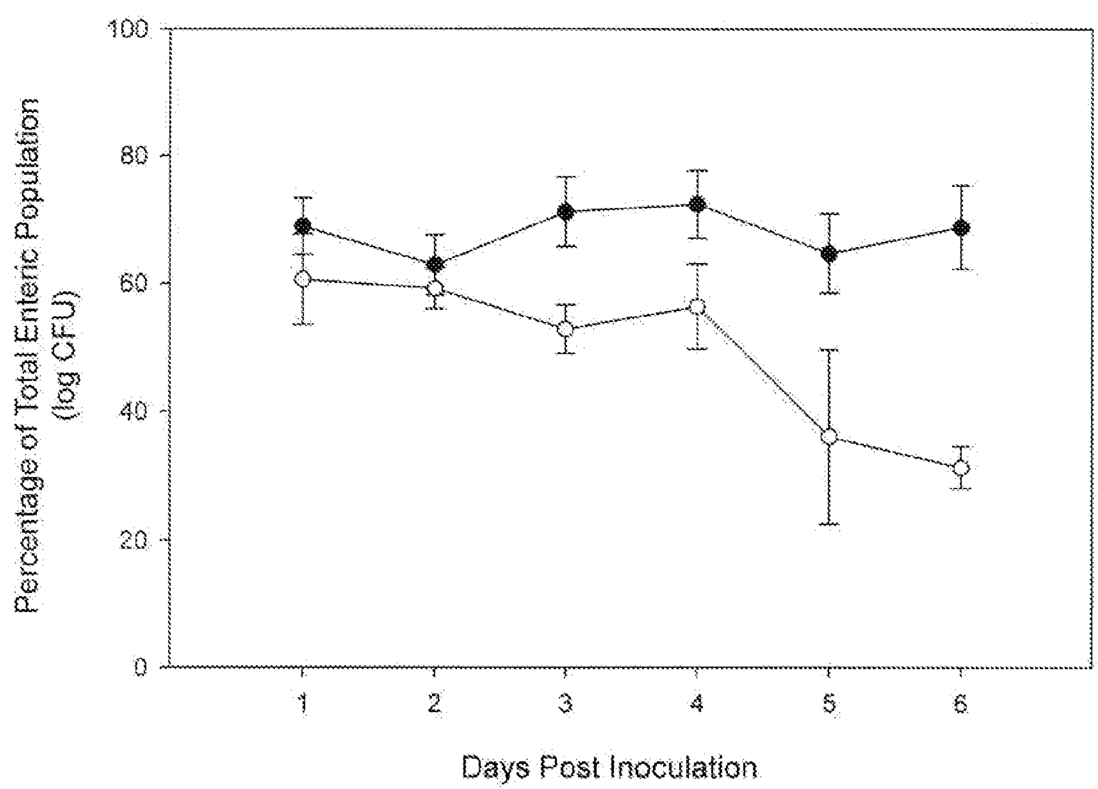
FIG. 6. The production of MccPDI contributes to the fitness of *E. coli*-25 within a calf. Each data point represents the percentage of the *E. coli*-25 mutant relative to the total lactose fermenting enteric CFU at the corresponding day post inoculation. Closed circles represent *E. coli*-25ΔtraM (n=7 calves) and open circles correspond to *E. coli*-25ΔmcpMΔmcpI (n=4 calves). Error bars represent the standard error of the mean.

If most native *E. coli* strains are susceptible to MccPDI, and if the MccPDI producing strain has a fitness advantage relative to non-producing strains of *E. coli*, then the MccPDI-producing strain should be found in greater numbers relative to the total *E. coli* population. We enumerated the CFU for the *E. coli*-25 mutants relative to the CFU lactose-fermenting enteric bacteria in the fecal samples. *E. coli*-25ΔmcpMΔmcpI accounted for <0.2% of the total lactose-fermenting enteric bacteria by day six, whereas *E. coli*-25ΔtraM consistently comprised >2% of this population throughout the trial (repeated measures ANOVA, P=0.01; FIG. 6). There was no difference between the total number of lactose-fermenting bacteria between the two groups (P=0.96). These results confirm the MccPDI-producing strain has a selective advantage over the non-producing strain in this model.

Figure 7:
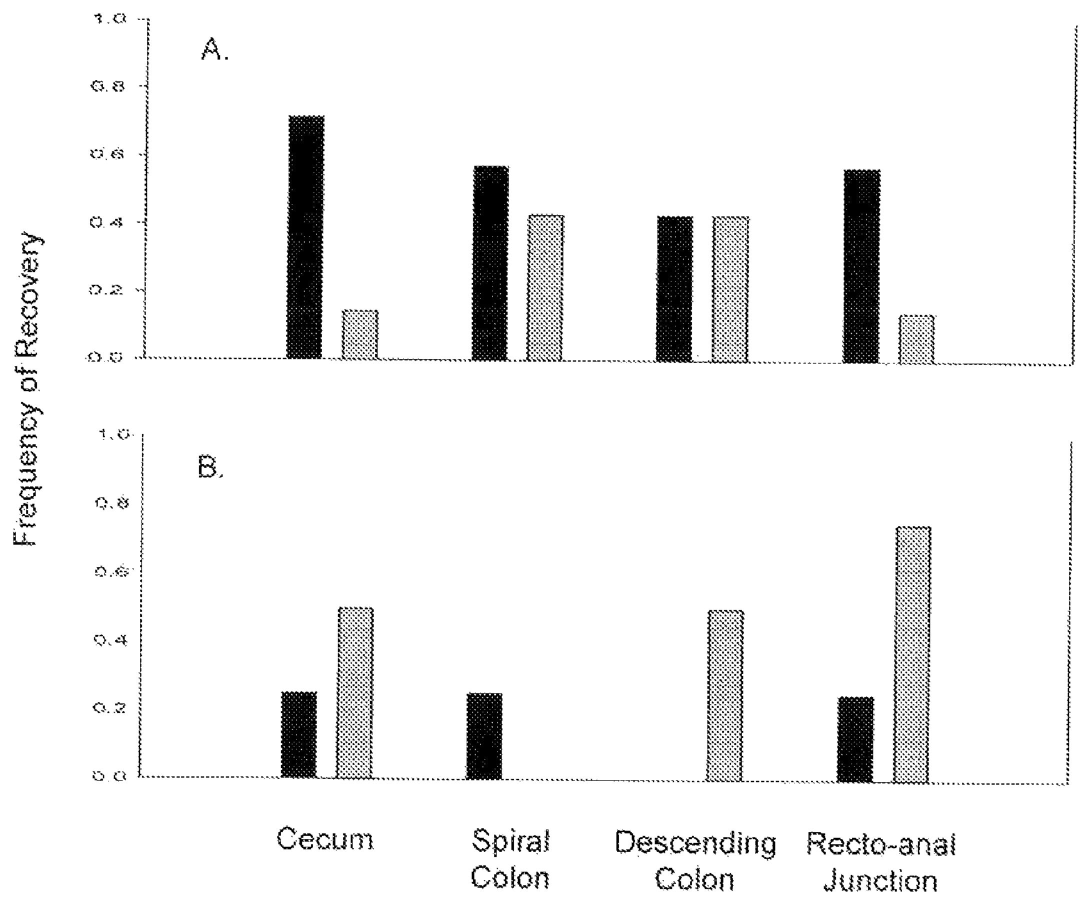
FIGS. 7A and B. MccPDI-producing *E. coli*-25 is recovered more frequently from GI tissues. Bars represent the frequency of recovery for competing strains in each trial at four segments of the GI tract: A. MccPDI-producing *E. coli*-25ΔtraM (black) and *E. coli*-186 (grey), B. MccPDI-knockout *E. coli*-25ΔmcpMΔmcpI (black) and *E. coli*-186 (grey).
Figure 8A:
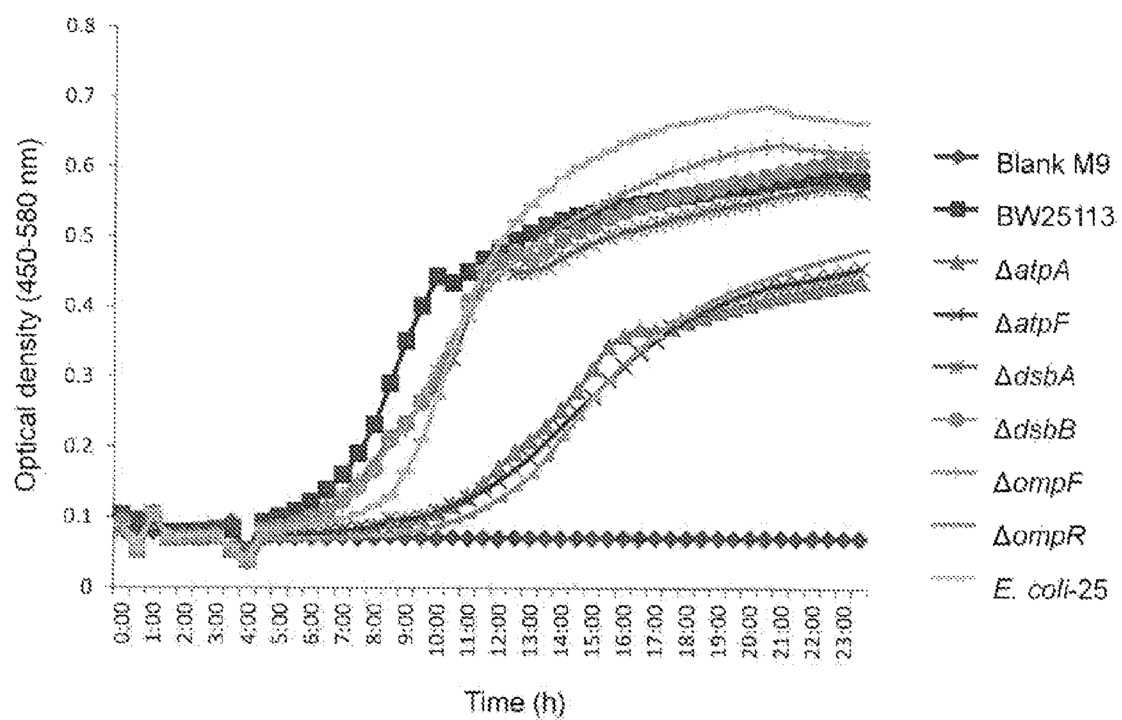
FIGS. 8A and B. Growth curves of *E. coli*-25, *E. coli* BW25113, and the MccPDI-resistant mutants ΔarpA, ΔatpF, ΔdsbA, ΔdsbB, ΔompF, and ΔompR when cultured in M9 minimal media (A) or LB media (B).
Figure 8B:
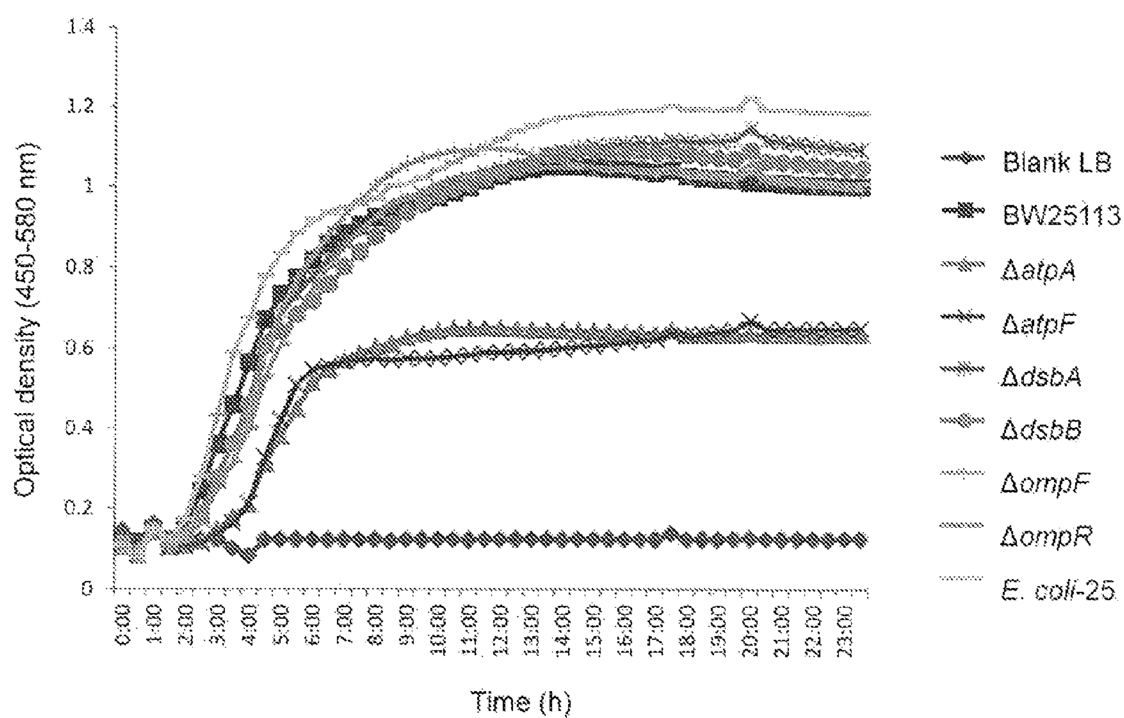

*E. coli* was consistently recovered from tissues of the lower gastrointestinal tract (GI). The inoculated strains, however, were typically only detected at counts just above the detection level. *E. coli*-25ΔtraM strain was recovered more frequently compared to *E. coli*-186, whereas *E. coli*-25ΔmcpMΔmcpI was recovered at a frequency similar to the *E. coli*-186 strain (P=0.01 and P=0.052, respectively; paired t-test; FIGS. 7A and B). There were no apparent differences in the frequency of detection between tissues (ANOVA, P=0.41). These results are consistent with *E. coli*-25ΔtraM having an in vivo fitness advantage allowing better colonization within calves.

Sixteen arbitrarily selected *E. coli* from each calf were tested for strain identity. Of calves inoculated with *E. coli*-25ΔtraM and *E. coli*-186, we detected the expected strains in 5 and 6 calves, respectively. We only recovered the expected strains from 1 of 4 calves for the non-microcin treatment group.

Bacteriocin-producing bacteria present an attractive means to control pathogens in food animal production. *E. coli*-25ΔtraM reduces the shedding of *E. coli*-186 confirming that MccPDI is functional in vivo. Changing the timing and doses of *E. coli*-25ΔtraM may potentially improve the treatment effect because it is unknown when or at what concentration MccPDI functions in vivo. Future research should investigate the use of multiple bacteriocinogenic strains, increased doses, or pre-inoculation of *E. coli*-25ΔtraM to limit pathogenic *E. coli* populations in cattle.

REFERENCES FOR EXAMPLE 11

1. Broschat, S. L., D. R. Call, M. A. Davis, D. Meng, S. Lockwood, R. Ahmed, and T. E. Besser. 2010. J Clin Microbiol 48:4072-82.
2. Chaslus-Dancla, E., G. Gerbaud, M. Lagorce, J. P. Lafont, and P. Courvalin. 1987. Antimicrob Agents Chemother 31:784-8.
3. Datsanko, K. A., and B. L. Wanner. 2000. Proc Natl Acad Sci USA 97:6640-5.
4. Eberhart, L. J., J. R. Deringer, K. A. Brayton, A. A. Sawant. T. E. Besser, and D. R. Call. 2012. Appl Environ Microbiol 78:6592-9.
5. Enne, V. I., D. M. Livermore, P. Stephens, and L. M. Hall. 2001. Lancet 357:1325-8.
6. Hinton. M., D. J. Hampson, E. Hampson, and A. H. Linton. 1985. J Hyg (Lond) 95:77-85.
7. Jackson, C. R., P. J. Fedorka-Cray, J. B. Barrett, and S. R. Ladely. 2004. Appl Environ Microbiol 70:4205-10.
8. Khachatryan, A. R., T. E. Besser, D. D. Hancock, and D. R. Call. 2006 Appl Environ Microbiol 72:4583-8.
9. Khachatryan, A. R., D. D. Hancock, T. E. Besser, and D. R. Call. 2006. Appl Environ Microbiol 72:443-8.
10. Khachatryan, A. R., D. D. Hancock. T. E. Besser, and D. R. Call. 2004. Appl Environ Microbiol 70:752-7.
11. Sawant, A. A., N. C. Casavant, D. R. Call, and T. E. Besser. 2011. Appl Environ Microbiol 77:2345-51.
12. Shringi, S., A. Garcia, K. K. Lahmers, K. A. Potter. S. Muthupalani, A. G Swennes, C. J. Hovde, D. R. Call, J. G Fox, and T. E. Besser. 2012. Infect Immun 80:369-80.
13. Singer, R. S., R. Finch, H. C. Wegener, R. Bywater, J. Walters, and M. Lipsitch. 2003. Lancet Infect Dis 3:47-51.

Example 12

Identification of a Receptor and Associated Proteins Required for MccPDI to Recognize and Inhibit Susceptible *E. coli*

The *E. coli* Keio Collection, a single-gene deletion library, was screened for mutants able to grow in the presence of the MccPDI producing strain *E. coli*-25. The Keio Collection includes individual gene knockouts for all non-essential genes that are expressed by *E. coli* strain BW25113, which is also sensitive to PDI. Screening of the full library followed by verification experiments demonstrated that mutants of atpA, atpF, dsbA, dsbB, ompF, or ompR were no longer sensitive to PDI, indicating these genes are required for MccPDI function.

Materials and Methods

Strains and Culture Conditions.

*E. coli*-25 [streptomycinR, sulfadiazineR, tetracyclineR, (SSuTR)](26), *E. coli* S17, *E. coli* BW25113 and the *E. coli* BW25113 gene-deletion library (Keio Collection, kanamycinR, Thermo Scientific) were used in this study. *E. coli* BW25113 was purchased from the *Coli* Genetic Stock Center (CGSC, Yale) and it is susceptible to antibiotics employed in the current study. To isolate this strain in a mixed culture, *E. coli* BW25113 was made nalidixic acid resistant by passaging 5 times with increasing concentrations until it was capable of growing in 30 μg/ml nalidixic acid. Unless stated otherwise, all strains were cultured in either Luria Broth (LB) or M9 Minimal Media at 37° C. shaking 250 rpm. Antibiotics were used at the following concentrations: tetracycline (50 μg/ml), chloramphenicol (34 μg/ml), kanamycin (50 μg/ml), nalidixic acid (30 μg/ml) and ampicillin (100 μg/ml).

Screening the Keio Collection for Loss of PDI.

The Keio collection of *E. coli* knockouts (Thermo Scientific) was employed to identify genes associated with susceptibility to MccPDI. Each mutant was grown overnight at 37° C. without shaking in a 96-well plate containing 150 μl fresh LB (50 μg/ml kanamycin) per well. A 10 ml culture of *E. coli*-25 was also started at this time in LB (50 μg/ml tetracycline) and incubated at 37 C with shaking (250 rpm). The following day each mutant was individually placed into co-culture with *E. coli*-25 in a sterile, U-bottom 96-well plate with 200 μl M9 minimal media per well. A 96-pin replicator (Boekel Scientific) was used to transfer overnight cultures (~1 μl) of each strain for competition experiments. The replicator was sterilized 3λ between each use by submerging pins into 70% ethanol and flaming. The *E. coli*-25 culture was poured into a sterile plastic trough and transferred in the same manner. Competition cultures were incubated overnight at 37° C., shaking at 100 rpm. Approximately 24 h later co-cultures (~1 μl) were transferred onto LB agar containing kanamycin or tetracycline to select for the Keio strains or *E. coli*-25, respectively. The plates were incubated at 37° C. for at least 6 h. Growth on tetracycline verified the presence of *E. coli*-25 in the culture. No growth on kanamycin indicated that the Keio knockout strain being tested was still susceptible to PDI. Growth of a Keio mutant strain on the kanamycin plate indicated putative identification of gene knockouts that were no longer susceptible to PDI.

Competition Assays and Enumeration of Resistant *E. coli* Mutants.

To confirm detection of PDI-resistant strains from the Keio collection, prospective strains were grown overnight in LB with antibiotic selection. Each mutant strain culture was then added (10 μl) with *E. coli*-25 culture (10 μl) to 2 ml M9 media. These co-cultures were incubated at 37° C. for 8 to 24 h. To determine the CFUs of each strain following competition, serial dilutions of the co-cultures were prepared in a 96-well plate containing sterile PBS and then spotted (5 μl) onto LB agar supplemented with kanamycin or tetracycline. Agar plates (3 per enumerated dilution) were incubated overnight at 37° C. and colonies were tallied for total colony forming units (cfu).

PCR Verification of the Knockout Mutants.

Primers corresponding to sequence up- and downstream the deleted gene (Table 3) were designed to verify the location of the kanamycin cassette insertion. Reactions were carried out with an initial denaturing step at 95° C. for 4 min, followed by 30 cycles of 95° C. for 20 s, 55° C. for 20 s, 72° C. for 1 min 20 s, and a final extension at 72° C. for 5 min. The PCR products were evaluated using electrophoresis alongside an O'gene Ruler 1 Kb plus ladder (Thermo Scientific) to determine the amplicon sizes. The wild-type (non-mutant) *E. coli* BW25113 was included as a control in addition to a no-template negative control.

Regenerating Resistant Mutants in *E. coli* S17.

To validate the findings from the Keio library screen, we generated independent mutants in a PDI sensitive strain, *E. coli* S17. The methods used to create these mutants were previously described by Datsenko and Wanner (2000; Proc Natl Acad Sci USA 97:6640-5) and were the same used to create the Keio Collection (Baba et al. Mol Sys Biol 2:2006 0008). The new gene-deletion mutants were generated with the insertion of chloramphenicol resistance (cat) instead of a kanamycin cassette as was used for the Keio Collection.

PCR primers were designed to amplify the chloramphenicol cassette from plasmid pKD3 and contained extensions identical to the sequence flanking the gene of interest (Table 3). *E. coli* S17 was transformed with the pKD46 plasmid, which facilitates homologous recombination between the gene of interest and the PCR amplicon. *E. coli* S17 pKD46 was grown in super optimal broth (2% bacto-trypton, 0.5% yeast extract, 8.56 mM NaCl, 2.5 mM KCL, 10 mM $MgCl_2$) with ampicillin and 0.1 mM arabinose to induce the proteins necessary for homologous recombination. These induced cells were then made competent and electroporated with the chloramphenicol amplicon containing the requisite flanking sequences. Transformed cells were recovered at 30° C. and were plated onto LB agar with chloramphenicol to select for successful deletion mutants. PCR was used to verify the insertion site of the chloramphenicol cassette (Table 3) using PCR conditions as describe above.

Growth Curves.

All strains, including the gene knockout mutants, were assessed for their ability to grow in M9 and LB media. Growth curves were run on a BioScreen C (Oy Growth Curves Ab Ltd). Each strain was grown individually overnight in LB media with antibiotic selection. These cultures were used to inoculate (1:1,000 dilution) M9 minimal media or LB broth without antibiotics. Cultures incubated for 24 h at 37° C. with continuous shaking and optical density (450-580 nm) measured every 30 min.

Fluorescent Labeling and Micro Copy.

*E. coli*-25ΔmcpMΔmcpI, *E. coli*-25ΔtraM, and *E. coli*-186 were each transformed with a vector expressing cherry red fluorescent protein (pFPV-mCherry) or GFP (pFPV25). Competition assays (described above) were conducted with the fluorescently labeled cells; one with MccPDI-producing *E. coli*-25ΔtraM+pFPV-mCherry and PDI-susceptible *E. coli*-186+pFPV25, and another with MccPDI-nonproducing *E. coli*-25ΔmcpMΔmcpI+pFPV-mCherry and PDI-susceptible *E. coli*-186+pFPV25. Additionally, these competitions were repeated where each strain carried the opposite plasmid to ensure the results were not caused by either strain differentially expressing either fluorescent protein. Individual cultures were run as controls. Each culture was visualized at 24 h using a fluorescent scope at 60× magnification.

Results

Six *E. coli* mutants in the Keio Collection were resistant to PDI). The single gene deletion *E. coli* mutant library, called the Keio Collection, was used to identify genes putatively associated with susceptibility to MccPDI. Approximately 3,985 mutants were screened using a high-throughput 96-well plate method. Following two rounds of screening using these methods, six mutants were identified as potentially being resistant to inhibition by *E. coli*-25. These mutants were then placed into a 2 ml competition experiment (M9 media) with *E. coli*-25 and CFUs were subsequently enumerated after 24 h co-culture. Mutants that were able to grow to a population density >$10^5$ CFU were considered resistant to PDI and these included the mutants with a deletion in atpA, atpF, dsbA, dsbB, ompF, or ompR (Table 4).

TABLE 4

Gene-knockout mutants that are no longer susceptible to killing by *E. coli*-25. PCR primer sequences amplify the gene of interest and were used to verify the specific knockouts. The CFUs represent the average of triplicate competition assays.

| Gene Disrupted | Primers: Gene-specific primers and flanking sequences (H1[a] and H2[b]) | Gene Function | Co-culture with *E. coli*-25 (CFU) |
|---|---|---|---|
| atpA | atpA fwd: TGCTGCGATGGAAAAACGTC (SEQ ID NO: 36) atpA rvs: TTCTGGACGCTTGCGATCTT (SEQ ID NO: 37) H1: CTTGCAGACGTCTTGCAGTCTTAAGGGGACTGGAGC (SEQ ID NO: 38) H2: GCCTTGCGGCCTGCCCTAAGGCAAGCCGCCAGACGT (SEQ ID NO: 39) | ATP synthase F1 complex, a subunit; also called papA | $4.10 \times 10^5$ |
| atpF | atpF fwd: ATCGCTGTAGGTCTGGGTCT (SEQ ID NO: 40) atpF rvs: ATGTCCTGCCAGCGTTCTAC (SEQ ID NO: 41) H1: AATATCAGAACGTTAACTAAATAGAGGCATTGTGCT (SEQ ID NO: 42) H2: CTACCGTAATAAATTCAGACATCAGCCCCTCCCTCC (SEQ ID NO: 43) | ATP synthase, F0 complex, b subunit; also called papF | $6.51 \times 10^6$ |
| dsbA | dsbA fwd: AGCGGCAGGATGCATTATCA (SEQ ID NO: 44) dsbA rvs: GGGAAGATTACTGGCTGCGA (SEQ ID NO: 45) H1: GTGAATATTCACGGGCTTTATGTAATTTACATTGAA (SEQ ID NO: 46) H2: AATTAACACCTATGTATTAATCGGAGAGAGTAGATC (SEQ ID NO: 47) | Periplasmic protein disulfide isomerase (disulfide bond formation) | $2.37 \times 10^7$ |
| dsbB | dsbB fwd: CAATGGCAGATGAAGCGAGC (SEQ ID NO: 48) dsbB rvs: TGCAAATGGGCTGGATAGCA (SEQ ID NO: 49) H1: AACTGCGCACTCTATGCATATTGCAGGGAAATGATT (SEQ ID NO: 50) | Disulfide oxidoreductase (disulfide bond formation) memberane protein; oxidizes | $3.97 \times 10^7$ |

TABLE 4-continued

Gene-knockout mutants that are no longer susceptible to killing by *E. coli*-25. PCR primer sequences amplify the gene of interest and were used to verify the specific knockouts. The CFUs represent the average of triplicate competition assays.

| Gene Disrupted | Primers: Gene-specific primers and flanking sequences (H1[a] and H2[b]) | Gene Function | Co-culture with *E. coli*-25 (CFU) |
|---|---|---|---|
| | H2: CAGGAAAAAAGCGCTCCCGCAGGAGCGCTGAAGGGA (SEQ ID NO: 51) | periplasmic DsbA | |
| ompF | ompF fwd: CGCTATCAGGGTAACGGGAG (SEQ ID NO: 52) ompF rvs: AGCACTTTCACGGTAGCGAA (SEQ ID NO: 53) H1: GTTGTCAGAATCGATCTGGTTGATGATGTAGTCAAC (SEQ ID NO: 54) H2: GTGATCGTCCCTGCTCTGTTAGTAGCAGGTACTGCA (SEQ ID NO: 55) | Outer memberane protein, porin | $9.50 \times 10^6$ |
| ompR | ompR fwd: TGTTGCGAACCTTTGGGAGT (SEQ ID NO: 56) ompR rvs: AGCAAGGTGACGATGAGCAA (SEQ ID NO: 57) H1: GGGCAAATGAACTTCGTGGCGAGAAGCGCAATCGCC (SEQ ID NO: 58) H2: CTTACAAATTGTTGCGAACCTTTGGGAGTACAAACA (SEQ ID NO: 59) | Transcriptional regulatory protein OmpR; Response regulator for osmoregulation | $2.12 \times 10^6$ |

[a] *E. coli* S17 gene-specific sequences are shown. For gene deletion mutants, flanking sequences also included the chloramphenicol primer site: TGTGTAGGCTGGAGCTGCTTCG, (SEQ ID NO: 60) 3' to the *E. coli* S17 specific sequence.

[b] *E. coli*-25 gene-specific sequences are shown. For gene deletion mutants, flanking sequences also included the chloramphenicol primer site: CATATGAATATCCTCCTTA, (SEQ ID NO: 61) 3' to the *E. coli* S17 specific sequence.

We claim:

1. A method of killing or decreasing adverse effects of pathogenic *Escherichia coli* (*E. coli*) and/or *Shigella* bacteria, comprising identifying a surface or subject known to or suspected of contamination with said pathogenic *E. coli* and/or *Shigella* bacteria; and contacting said pathogenic *E. coli* and/or *Shigella* bacteria with microcin MccPDI having SEQ ID NO: 24 or a functional variant thereof, or an organism that produces MccPDI SEQ ID NO: 24 or a functional variant thereof, wherein said functional variant has a sequence at least 95% identical to SEQ ID NO: 24.

2. The method of claim 1, wherein said pathogenic *Escherichia coli* bacteria are Shiga-toxin *E. coli* (STEC) bacteria.

3. The method of claim 1, wherein said STEC bacteria are selected from the group consisting of: enterohaemorrhagic *E. coli* (EHEC), enteropathogenic *E. coli* (EPEC), enterotoxigenic *E. coli* (ETEC), enteroinvasive *E. coli* (EIEC), enteroggregative *E. coli* (EAEC), diffusively adherent *E. coli* (DAEC), uropathogenic *E. coli* (UPEC) and neonatal meningitis *E. coli* (NMEC).

4. The method of claim 2, wherein said STEC bacteria are of a serotype selected from the group consisting of O111, O145, O103, O26, O45, O121 and O157.

5. The method of claim 1, wherein said pathogenic *Shigella* bacteria are *Shigella flexneri, Shigella sonnei* or *Shigella dysenteriae.*

6. The method of claim 1, wherein said organism that produces microcin MccPDI is a naturally occurring bacteria.

7. The method of claim 6, wherein said naturally occurring bacteria are E-25 or E-264.

8. The method of claim 1 wherein said organism that produces microcin MccPDI is a genetically modified organism harboring a heterologous nucleic acid which is expressed to produce said microcin MccPDI having SEQ ID NO. 24 or said functional variants thereof.

* * * * *

SEQUENCE LISTING

<160> NUMBER OF SEQ ID NOS: 61

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
tagttgcagg ggcataagaa 20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
aggaaacgca aacagcaact 20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3
caggttcaat gctccgttgc 20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 4
gcgacctttc gctttgatgg 20

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 5
ccgtaatgac cgttccagt 19

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 6
ccatttccac taccatgatc t 21

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 7
ataacccgta tctttacgtt gccttacgtt ca 32

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 8
ctagaatccg caataatttt acagtttgat 30

<210> SEQ ID NO 9
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 9
aataacgtga ttgcatatta cttatctcag gagttc 36

<210> SEQ ID NO 10
<211> LENGTH: 36
<212> TYPE: DNA
<213> ORGANISM: Artificial Sequence
<220> FEATURE:

<223> OTHER INFORMATION: Synthetic oligonucleotide primer

<400> SEQUENCE: 10
atccctggaa ggactacaac ctatgaccga aaatac 36

<210> SEQ ID NO 11
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 11
gtaatttaat aaacatagta gcgccctcca ttatatctat 40

<210> SEQ ID NO 12
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 12
aacgcacaaa ataacaaaca accgataggg gaaatatgat 40

<210> SEQ ID NO 13
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 13
attatcttta ctatatttat atatgttatc attcataatg 40

<210> SEQ ID NO 14
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 14
aacgcacaaa ataacaaaca accgataggg gaaatatgat 40

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 15
tggtgatgaa ttcctgtcaa a 21

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 16
taccagtttc acccgtcaca 20

```
<210> SEQ ID NO 17
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 17

tcagccattc ccataaatga cgagtatcaa ggttgacg                              38


<210> SEQ ID NO 18
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 18

ttgacggaaa ggttacttat tgtattaaaa ataatg                                36


<210> SEQ ID NO 19
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 19

gatatacatc tgacctgtgt gatgttaaag ttttatacta                            40


<210> SEQ ID NO 20
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 20

atagaaaaaa taagaacaat ctccgcgaaa tagcattatg                            40


<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide primer site

<400> SEQUENCE: 21

tgtgtaggct ggagctgctt cg                                               22


<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide primer site

<400> SEQUENCE: 22

catatgaata tcctcctta                                                   19


<210> SEQ ID NO 23
<211> LENGTH: 356
<212> TYPE: DNA
<213> ORGANISM: Escherichia coli
```

<400> SEQUENCE: 23

```
atggcaaata taagagaatt aactttagat gagataacgc ttgtcagcgg aggaacagca     60

actttgaagg tggcccccgt aatgaccgtt ccagtggggc tcgtaactca ctgggtcgaa    120

acgcaccaac tcatatttat agtgatccaa gcactgtaaa atgcgctaac gctgtattta    180

gtggaatgat tggtggtgcg atcaaaggag gtcccatagg aatggcaaga ggtaccattg    240

gtggagccgt tgttggtcaa tgtctctcag atcatggtag tggaaatgga agtggtaaca    300

gaggaagttc cagtagttgt tcaggtaata atgttggcgg aacatgtaac cgataa        356
```

<210> SEQ ID NO 24
<211> LENGTH: 120
<212> TYPE: PRT
<213> ORGANISM: Escherichia coli

<400> SEQUENCE: 24

```
Met Ala Asn Ile Arg Glu Leu Thr Leu Asp Glu Ile Thr Leu Val Ser
1               5                   10                  15

Gly Gly Asn Ala Asn Ser Asn Phe Glu Gly Gly Pro Arg Asn Asp Arg
            20                  25                  30

Ser Ser Gly Ala Arg Asn Ser Leu Gly Arg Asn Ala Pro Thr His Ile
        35                  40                  45

Tyr Ser Asp Pro Ser Thr Val Lys Cys Ala Asn Ala Val Phe Ser Gly
    50                  55                  60

Met Ile Gly Gly Ala Ile Lys Gly Gly Pro Ile Gly Met Ala Arg Gly
65                  70                  75                  80

Thr Ile Gly Gly Ala Val Val Gly Gln Cys Leu Ser Asp His Gly Ser
                85                  90                  95

Gly Asn Gly Ser Gly Asn Arg Gly Ser Ser Ser Ser Cys Ser Gly Asn
            100                 105                 110

Asn Val Gly Gly Thr Cys Asn Arg
        115                 120
```

<210> SEQ ID NO 25
<211> LENGTH: 216
<212> TYPE: DNA
<213> ORGANISM: Escherichia coli

<400> SEQUENCE: 25

```
atggagggcg ctactatgtt tattaaatta ctttccttta tatgtggttt gttactggga     60

tttgcactat tgagtggctc ctctgttatt gatttatact ggttttcact accttccgag    120

ttttcaaaga ttgtagtcat gctgatcact ctttttttcca cggcaagatt catggactat    180

atcatagaaa aaataagaac aatctccgcg aaatag                              216
```

<210> SEQ ID NO 26
<211> LENGTH: 71
<212> TYPE: PRT
<213> ORGANISM: Escherichia coli

<400> SEQUENCE: 26

```
Met Glu Gly Ala Thr Met Phe Ile Lys Leu Leu Ser Phe Ile Cys Gly
1               5                   10                  15

Leu Leu Leu Gly Phe Ala Leu Leu Ser Gly Ser Ser Val Ile Asp Leu
            20                  25                  30

Tyr Trp Phe Ser Leu Pro Ser Glu Phe Ser Lys Ile Val Val Met Leu
        35                  40                  45
```

```
Ile Thr Leu Phe Ser Thr Ala Arg Phe Met Asp Tyr Ile Ile Glu Lys
    50                  55                  60

Ile Arg Thr Ile Ser Ala Lys
65                  70
```

<210> SEQ ID NO 27
<211> LENGTH: 636
<212> TYPE: DNA
<213> ORGANISM: Escherichia coli

<400> SEQUENCE: 27

```
atgaatgata acatatataa atatagtaaa gataatgcga tagcgtttct tctacttgtt     60

gttatatcaa cagttgtgat attcacaccg gcattcacca tacaatatat tggtttggat    120

ctggcatttt cctttgtctt tattactgaa attttaatgt caacttcatt ttatattttt    180

tacttaagaa gaataccagg ttgtaaaatc accataaaga caaatgcgaa aacattaaag    240

ctattagtaa tatcatttgc tgtgattgct ctcatgcaac tgcttatttt tgcttataga    300

gacaatttga acaatagtga atcaacttca cttaattgga ttgaaatatt tatactggtc    360

ctgacagttc cgtattatga agaaattgtt taccgaacat gtctattcgg tcttctatgt    420

acgacttata aaaaagaatt atttaccccc tgcgtgtgta catctttatt tttctgcctg    480

atgcatccgc agtattataa tgtggctgat caaattattc tgtttattat gtcaatgtta    540

ttgttgaata taaggatttg cagtaagggg attttctatc caatgctgtt acatgcggga    600

ataaacggct ttgttatatt gttaaatata ttatag                              636
```

<210> SEQ ID NO 28
<211> LENGTH: 211
<212> TYPE: PRT
<213> ORGANISM: Escherichia coli

<400> SEQUENCE: 28

```
Met Asn Asp Asn Ile Tyr Lys Tyr Ser Lys Asp Asn Ala Ile Ala Phe
1               5                   10                  15

Leu Leu Leu Val Val Ile Ser Thr Val Val Ile Phe Thr Pro Ala Phe
            20                  25                  30

Thr Ile Gln Tyr Ile Gly Leu Asp Leu Ala Phe Ser Phe Val Phe Ile
        35                  40                  45

Thr Glu Ile Leu Met Ser Thr Ser Phe Tyr Ile Phe Tyr Leu Arg Arg
    50                  55                  60

Ile Pro Gly Cys Lys Ile Thr Ile Lys Thr Asn Ala Lys Thr Leu Lys
65                  70                  75                  80

Leu Leu Val Ile Ser Phe Ala Val Ile Ala Leu Met Gln Leu Leu Ile
                85                  90                  95

Phe Ala Tyr Arg Asp Asn Leu Asn Asn Ser Glu Ser Thr Ser Leu Asn
            100                 105                 110

Trp Ile Glu Ile Phe Ile Leu Val Leu Thr Val Pro Tyr Tyr Glu Glu
        115                 120                 125

Ile Val Tyr Arg Thr Cys Leu Phe Gly Leu Leu Cys Thr Thr Tyr Lys
    130                 135                 140

Lys Glu Leu Phe Thr Pro Cys Val Cys Thr Ser Leu Phe Phe Cys Leu
145                 150                 155                 160

Met His Pro Gln Tyr Tyr Asn Val Ala Asp Gln Ile Ile Leu Phe Ile
                165                 170                 175
```

```
Met Ser Met Leu Leu Leu Asn Ile Arg Ile Cys Ser Lys Gly Ile Phe
            180                 185                 190

Tyr Pro Met Leu Leu His Ala Gly Ile Asn Gly Phe Val Ile Leu Leu
        195                 200                 205

Asn Ile Leu
    210


<210> SEQ ID NO 29
<211> LENGTH: 1254
<212> TYPE: DNA
<213> ORGANISM: Escherichia coli

<400> SEQUENCE: 29

atgaatatat tcagaagtga agcaatagaa catcataatg acactgaata tggtgacatt      60

attttaccaa catcatttag cctatccgta tgtgcaacag ttacattatt cattatgtta     120

agtctgactg tattcatata ttacggtagc tatacaagga aagcgcatct tacaggtatc     180

gtcatgccct catcaggact ggtaaaaata attcctcaat atgcaggata tgtaacacaa     240

ctgactgtat ccgaaggaga acacgtaact gcagggacac aactctatca tataagtgga     300

gaacattata acggtaacgg aactggcaca ttagcaacga tgagtatttc cctgaagact     360

cagtatatta tgttggcctc ccagcaatcc tttgagtcgc gagataatag tcaacaacag     420

gaagccatac ggcaaaggat gatatcactt gagccgcaaa taagaagtgc agaacaaaga     480

cttcagcttg ctgaacgtca ggcagaactg gctatatccg tcatggaacg ctataaaaaa     540

ttggctggta cgcattatgt gtcagatatc gaattccaac agaaacaaat tgatgtttct     600

gccgctcaac aaaacgttga agatcagcgt caggggcttc tccagttaca tactgcaatg     660

gacacagcca aagatgaact aaatcatctt attgttcagg ggaaaagccg taaagcagaa     720

ctcgacagac aattgcaggt gctaaaacaa caacaggatg aactcgccgg acaagaaaaa     780

tttacactga gggctccagt atccgggact attgctgctg tactgatcaa acaggggcag     840

tctgtgaaag catctgaacc ggtcatgact ctcattcccg ataatgctca tttacaaatt     900

gagctttatg ctaccagcca gaaagccggt tttatccgac caggtcaacg ggtatctctg     960

aagttttcgg ccttccctta tcagaaattt ggtatccagt acggcacaat tcgtaaaatc    1020

agtcatacga ctctggctcc ttccgactta ttaccagttt cacccgtcac atggaaagaa    1080

aacgaagggc attatcgcgt tattgttgaa cctgaaaata catttatatt tgcatacgga    1140

aaaaaagaac cgctaagacc aggcatgact ctggaaggag acgtcaacct tgatactcgt    1200

catttatggg aatggctgac agagccccta tggagcatga aaggaaatct gtaa          1254


<210> SEQ ID NO 30
<211> LENGTH: 417
<212> TYPE: PRT
<213> ORGANISM: Escherichia coli

<400> SEQUENCE: 30

Met Asn Ile Phe Arg Ser Glu Ala Ile Glu His His Asn Asp Thr Glu
1               5                   10                  15

Tyr Gly Asp Ile Ile Leu Pro Thr Ser Phe Ser Leu Ser Val Cys Ala
            20                  25                  30

Thr Val Thr Leu Phe Ile Met Leu Ser Leu Thr Val Phe Ile Tyr Tyr
        35                  40                  45

Gly Ser Tyr Thr Arg Lys Ala His Leu Thr Gly Ile Val Met Pro Ser
    50                  55                  60
```

```
Ser Gly Leu Val Lys Ile Ile Pro Gln Tyr Ala Gly Tyr Val Thr Gln
65                  70                  75                  80

Leu Thr Val Ser Glu Gly Glu His Val Thr Ala Gly Thr Gln Leu Tyr
                85                  90                  95

His Ile Ser Gly Glu His Tyr Asn Gly Asn Gly Thr Gly Thr Leu Ala
            100                 105                 110

Thr Met Ser Ile Ser Leu Lys Thr Gln Tyr Ile Met Leu Ala Ser Gln
        115                 120                 125

Gln Ser Phe Glu Ser Arg Asp Asn Ser Gln Gln Gln Glu Ala Ile Arg
    130                 135                 140

Gln Arg Met Ile Ser Leu Glu Pro Gln Ile Arg Ser Ala Glu Gln Arg
145                 150                 155                 160

Leu Gln Leu Ala Glu Arg Gln Ala Glu Leu Ala Ile Ser Val Met Glu
                165                 170                 175

Arg Tyr Lys Lys Leu Ala Gly Thr His Tyr Val Ser Asp Ile Glu Phe
            180                 185                 190

Gln Gln Lys Gln Ile Asp Val Ser Ala Ala Gln Gln Asn Val Glu Asp
        195                 200                 205

Gln Arg Gln Gly Leu Leu Gln Leu His Thr Ala Met Asp Thr Ala Lys
    210                 215                 220

Asp Glu Leu Asn His Leu Ile Val Gln Gly Lys Ser Arg Lys Ala Glu
225                 230                 235                 240

Leu Asp Arg Gln Leu Gln Val Leu Lys Gln Gln Gln Asp Glu Leu Ala
                245                 250                 255

Gly Gln Glu Lys Phe Thr Leu Arg Ala Pro Val Ser Gly Thr Ile Ala
            260                 265                 270

Ala Val Leu Ile Lys Gln Gly Gln Ser Val Lys Ala Ser Glu Pro Val
        275                 280                 285

Met Thr Leu Ile Pro Asp Asn Ala His Leu Gln Ile Glu Leu Tyr Ala
    290                 295                 300

Thr Ser Gln Lys Ala Gly Phe Ile Arg Pro Gly Gln Arg Val Ser Leu
305                 310                 315                 320

Lys Phe Ser Ala Phe Pro Tyr Gln Lys Phe Gly Ile Gln Tyr Gly Thr
                325                 330                 335

Ile Arg Lys Ile Ser His Thr Thr Leu Ala Pro Ser Asp Leu Leu Pro
            340                 345                 350

Val Ser Pro Val Thr Trp Lys Glu Asn Glu Gly His Tyr Arg Val Ile
        355                 360                 365

Val Glu Pro Glu Asn Thr Phe Ile Phe Ala Tyr Gly Lys Lys Glu Pro
    370                 375                 380

Leu Arg Pro Gly Met Thr Leu Glu Gly Asp Val Asn Leu Asp Thr Arg
385                 390                 395                 400

His Leu Trp Glu Trp Leu Thr Glu Pro Leu Trp Ser Met Lys Gly Asn
                405                 410                 415

Leu


<210> SEQ ID NO 31
<211> LENGTH: 2185
<212> TYPE: DNA
<213> ORGANISM: Escherichia coli

<400> SEQUENCE: 31

atggaatcaa taaactggaa agtaaggaaa caactacccg ttatccgtca aaccgaatca     60
```

```
gctgaatgcg gtctggcgtg tctggctatg attgcctgct ggcatggact gaaaacagat    120

ttatcgacat tacgggaacg tttcaatata ggtattcagg gaatgacgct acaaaggttg    180

atcgaatgtg cagcgtccat ccatttatca tcacgtgcag ttcgtctgga acccgaagat    240

ctgaggtgtc ttaatcttcc atctattctg cactgggata tgaaccattt cgtcgttctc    300

cataaagttc ggggaaaccg gttatacatc catgatccgg acagaggaaa aattacaata    360

agtctgttgg acgcaggtaa gcattttaca ggagtggcac tggaattaac tccagccagt    420

gatttcaccc cccggaacga gagaaaaaaa tccacctgcg tcaactgaca gggaaaaccc    480

cggggctttt agcatcaatg acaaaaaatta ttatttttgc tctggccctt gagattctgg    540

ctttaggtgg tccacttctt aatcaactgg taattgatga agttctggtc gcagcagaca    600

gaagtctatt gtatgtcatt atagtggcac tactgttgtt atcactcata caattattac    660

tctccctagc acgacaatgg gcaacgatca gtttatccgt caattttaac atgcaatgga    720

ctgccagagt tttccatcat cttgtaagac tccctcttgc atggttcgat gcccgaagta    780

aaggaagtat taatgcccgt tttgaagcag tagatataat ccagcaggcg ctgacaacgc    840

aggttcttga aggcattctg gatatgctac ttattgtgac tgctctttgc atgatgctgt    900

tgtatagccc aggaatgaca ttaatcgcag taattgcagc tattatatat ggcgcactga    960

gagcattgtg gtatccggct ttacggcaat ctgttgaaga tgtctgggat gcaggaacta   1020

aggagtcggg gcattttctc gaaaccctta acggcattca gagtctgaga atcaacggtg   1080

taactattca cagagaagcg gcctggctga acctcaacgt tacccgcaga aacacacagc   1140

tacgccagaa tcgtttacaa atgagctatg aactgacgca tacactgacg gaaagtgtag   1200

tttcagccat tattttgtgg cagggagcag tagaagtgct ggatgggaca tttaccgtgg   1260

gtatgttggt tgcttactta tcctatcaga tgcgtttttc atccagtata agcaatctga   1320

ctgataactt tttttcctgg cgcatgcttg atgtttataa cgagagactt gccgatattg   1380

tgctaacacc acaggaaggt caccagaatc agcaccattg ggcaaaccat aatgaaacaa   1440

tatctgcaag ccagtacaga gaacataaat atgataatac ccatccacca ttacttatcg   1500

aaaaaataac atttagccat aagggcgcag ataaacccat attggataac gcgtcactaa   1560

tgctctttcc tggagaaata ttagcaataa caggtaaatc aggatgtggc aaatcaacat   1620

tggtaaagct tattcttgga attcatacac caagtgaagg aagaattaat gcatttggca   1680

taccacatac acattctgat tattttcagg ttcgtcaacg aattggcact gtattgcaag   1740

atgactatct tttcaaaggt tctatagctg ataatataat gttttttagc gaaattagag   1800

atcatgaaca catgcgtaaa tgcgcaagtc tggcacttat agacagtgat attatggcaa   1860

tgccaatggg ctatcaacat tacttggaga aaccggaggg ggactttcag gtggtcagaa   1920

gcaacgtatt ctactggcaa gagcactgta taaaaaaccc ggtctattat tactggacga   1980

agcaaccagt catcttgatg tggaaagtga aatagaaata agccagacat tacgccaact   2040

cggattcctg ttctgttaat agctcatcga ccagaaacaa tagcatccgc agacagagtt   2100

ctatctgaga gatggtcact tttcggaaat aacatatcga cctgccagaa ctcataatat   2160

aaataatcac cccaacagga ggtga                                         2185
```

<210> SEQ ID NO 32
<211> LENGTH: 729
<212> TYPE: PRT
<213> ORGANISM: Escherichia coli

<400> SEQUENCE: 32

```
Met Glu Ser Ile Asn Trp Lys Val Arg Lys Gln Leu Pro Val Ile Arg
1               5                   10                  15

Gln Thr Glu Ser Ala Glu Cys Gly Leu Ala Cys Leu Ala Met Ile Ala
            20                  25                  30

Cys Trp His Gly Leu Lys Thr Asp Leu Ser Thr Leu Arg Glu Arg Phe
        35                  40                  45

Asn Ile Gly Ile Gln Gly Met Thr Leu Gln Arg Leu Ile Glu Cys Ala
    50                  55                  60

Ala Ser Ile His Leu Ser Ser Arg Ala Val Arg Leu Glu Pro Glu Asp
65                  70                  75                  80

Leu Arg Cys Leu Asn Leu Pro Ser Ile Leu His Trp Asp Met Asn His
                85                  90                  95

Phe Val Val Leu His Lys Val Arg Gly Asn Arg Leu Tyr Ile His Asp
            100                 105                 110

Pro Asp Arg Gly Lys Ile Thr Ile Ser Leu Leu Asp Ala Gly Lys His
        115                 120                 125

Phe Thr Gly Val Ala Leu Glu Leu Thr Pro Ala Ser Asp Phe Thr Pro
    130                 135                 140

Arg Asn Glu Arg Lys Lys Ile His Leu Arg Gln Leu Thr Gly Lys Thr
145                 150                 155                 160

Pro Gly Leu Leu Ala Ser Met Thr Lys Ile Ile Ile Phe Ala Leu Ala
                165                 170                 175

Leu Glu Ile Leu Ala Leu Gly Gly Pro Leu Leu Asn Gln Leu Val Ile
            180                 185                 190

Asp Glu Val Leu Val Ala Ala Asp Arg Ser Leu Leu Tyr Val Ile Ile
        195                 200                 205

Val Ala Leu Leu Leu Leu Ser Leu Ile Gln Leu Leu Leu Ser Leu Ala
    210                 215                 220

Arg Gln Trp Ala Thr Ile Ser Leu Ser Val Asn Phe Asn Met Gln Trp
225                 230                 235                 240

Thr Ala Arg Val Phe His His Leu Val Arg Leu Pro Leu Ala Trp Phe
                245                 250                 255

Asp Ala Arg Ser Lys Gly Ser Ile Asn Ala Arg Phe Glu Ala Val Asp
            260                 265                 270

Ile Ile Gln Gln Ala Leu Thr Thr Gln Val Leu Glu Gly Ile Leu Asp
        275                 280                 285

Met Leu Leu Ile Val Thr Ala Leu Cys Met Met Leu Leu Tyr Ser Pro
    290                 295                 300

Gly Met Thr Leu Ile Ala Val Ile Ala Ala Ile Ile Tyr Gly Ala Leu
305                 310                 315                 320

Arg Ala Leu Trp Tyr Pro Ala Leu Arg Gln Ser Val Glu Asp Val Trp
                325                 330                 335

Asp Ala Gly Thr Lys Glu Ser Gly His Phe Leu Glu Thr Leu Asn Gly
            340                 345                 350

Ile Gln Ser Leu Arg Ile Asn Gly Val Thr Ile His Arg Glu Ala Ala
        355                 360                 365

Trp Leu Asn Leu Asn Val Thr Arg Arg Asn Thr Gln Leu Arg Gln Asn
    370                 375                 380

Arg Leu Gln Met Ser Tyr Glu Leu Thr His Thr Leu Thr Glu Ser Val
385                 390                 395                 400

Val Ser Ala Ile Ile Leu Trp Gln Gly Ala Val Glu Val Leu Asp Gly
                405                 410                 415
```

```
Thr Phe Thr Val Gly Met Leu Val Ala Tyr Leu Ser Tyr Gln Met Arg
            420                 425                 430

Phe Ser Ser Ser Ile Ser Asn Leu Thr Asp Asn Phe Phe Ser Trp Arg
        435                 440                 445

Met Leu Asp Val Tyr Asn Glu Arg Leu Ala Asp Ile Val Leu Thr Pro
    450                 455                 460

Gln Glu Gly His Gln Asn Gln His His Trp Ala Asn His Asn Glu Thr
465                 470                 475                 480

Ile Ser Ala Ser Gln Tyr Arg Glu His Lys Tyr Asp Asn Thr His Pro
                485                 490                 495

Pro Leu Leu Ile Glu Lys Ile Thr Phe Ser His Lys Gly Ala Asp Lys
            500                 505                 510

Pro Ile Leu Asp Asn Ala Ser Leu Met Leu Phe Pro Gly Glu Ile Leu
        515                 520                 525

Ala Ile Thr Gly Lys Ser Gly Cys Gly Lys Ser Thr Leu Val Lys Leu
    530                 535                 540

Ile Leu Gly Ile His Thr Pro Ser Glu Gly Arg Ile Asn Ala Phe Gly
545                 550                 555                 560

Ile Pro His Thr His Ser Asp Tyr Phe Gln Val Arg Gln Arg Ile Gly
                565                 570                 575

Thr Val Leu Gln Asp Asp Tyr Leu Phe Lys Gly Ser Ile Ala Asp Asn
            580                 585                 590

Ile Met Phe Phe Ser Glu Ile Arg Asp His Glu His Met Arg Lys Cys
        595                 600                 605

Ala Ser Leu Ala Leu Ile Asp Ser Asp Ile Met Ala Met Pro Met Gly
    610                 615                 620

Tyr Gln Thr Leu Leu Gly Glu Thr Gly Gly Gly Leu Ser Gly Gly Gln
625                 630                 635                 640

Lys Gln Arg Ile Leu Leu Ala Arg Ala Leu Tyr Lys Lys Pro Gly Leu
                645                 650                 655

Leu Leu Leu Asp Glu Ala Thr Ser His Leu Asp Val Glu Ser Glu Ile
            660                 665                 670

Glu Ile Ser Gln Thr Leu Arg Gln Leu Gly Ile Pro Val Leu Leu Ile
        675                 680                 685

Ala His Arg Pro Glu Thr Ile Ala Ser Ala Asp Arg Val Leu Tyr Leu
    690                 695                 700

Arg Asp Gly His Phe Ser Glu Ile Thr Tyr Arg Pro Ala Arg Thr His
705                 710                 715                 720

Asn Ile Asn Asn His Pro Asn Arg Arg
                725
```

<210> SEQ ID NO 33
<211> LENGTH: 98809
<212> TYPE: DNA
<213> ORGANISM: Escherichia coli

<400> SEQUENCE: 33

```
gatctaaagc agaaaaatct gcttttaaaa atagatttta ttttttgac gcaggtcaag      60

attaacttat tagaggtatc agtgaggagg cactggaaga gaagagatcg ttgtaatgct     120

tttcaaatta acgtaaagcg ggtatatttc ggctgttatt agctgtgcag agggtggcac     180

tctgtggagc aaagcggcga aagccggacg gcagaatgcg ccataaggca ttcaggagag     240

atggcatgta cgggcagtaa gtcagaagac tgaagatgtt ccggaagcca taaaaggaaa     300

acccccacta tctttcttac gaacttggcg gaacgacgaa agatagtggg ggcctcacag     360
```

```
aatacgggta aagtataatg aaaccgtacc agagattcaa ccctgtgcag tgtataaata    420
cacggcacaa tcgctccgcc ataagcgaca gcttgtggca ggtctgaaga atactccata    480
taacgcagta cactggagtc agttagcacc cgaagagcag atccgtttct gggaagacta    540
tgaagcggga agggcgacca ctttcctggt tgaaccggaa aggaagcgca cgaagcgtcg    600
tcgtggtgag cactccacca aacccaaatg cgaaaatccg tcctggtatc gtcctgagcg    660
ctataaggcg ctgagcgggc agctcgggca cgcctacaac cgtctggtga aaaaggaccc    720
ggtgaccggc gagcagagcc tgcgcatgca catgtctctg catccttttt acgtgcagaa    780
acgaacgtat gccggtcgca aatatgcttt ccgtccggaa aaacaacgcc tcctcgatgc    840
cgtctggccg gttctggtca gcttcagtga tgcgggcaca cataccgtag gcatgagtgt    900
ttcccgtctg gccagagaaa tcagcccgaa agacagcaag ggaaggttaa ttccggaact    960
ggaagtgacg gtctcccgcc tttcccgttt gctggccgaa caggtacgtt ttggtgtgct   1020
gggtgtttca gaggaaaccc tgtgggaccg tgaaacccgc cagcgtctgc cacgttacgt   1080
ctggataaca ccggcaggct ggcagatgct gggcgtcgac atggtaaaac ttcacgaaca   1140
gcagcagaaa cgactgcgtg aaagtgaaat ccgccagcag ctcattcggg aaggtgttct   1200
gcgtgaggat gaagatatct ccgtacatgc ggccagaaaa cgctggtatc tgcagcgcag   1260
tcaggatgcg ctgaaacacc gtcgtgcgaa agcagcagcc agtaagcgcg ccagacgcct   1320
gaagaaactg cctgccgacc agcagattca tgagatggca gagtatctca ggaagcgtct   1380
gcctccggat gaagcctatt tttgttccga tgaccatctg aagcgaatgg ccatcaggga   1440
gttgcgtcag cttgaactga cgctggctgc cccgccaccg cactagacag caccattccc   1500
tcagcactga atcatcacca gcccctccgg ggctttcggc gctggttccg ctcagcccaa   1560
aatccgcagt aatcacctta aatcccctca gaggggcata tctgcccata aaaccacgca   1620
tcagtcatca gaacatggcc acgttgtttc agttatccac ataaatccgc aaataaagaa   1680
ctttaagaag ctgcaaacct gaaacagcaa acctgcaata tagtcttaac cccattattt   1740
aatcccctgc gttgcttcgc cgcagggaaa gtctttatct ctgaaaccac tgtgaacaaa   1800
tacaaagagg ccttcgcttg cagcggccag ggccacgccg ctcagaatct aaaagcacct   1860
cccacgctaa cgcgcgggcc ccgaccctca ccattcagaa accacagcaa aaaaacatca   1920
ggaataaaaa cgccacacaa acgcagcacc gtgcctaccc ctcataactg aaaagcgagg   1980
ccgcccccgc ccgaagggcg ggaacaacat cgcttttaat tatgaatgtt gtaactaagc   2040
attcccatcg ctgtcagtct tctggctgga agtatcgagt acacgctcgt aagcggccct   2100
cacggcccgc taacgcggag atacgccccg acttcgggta aaccctcgtc gggaccactc   2160
cgaccgcgca cagaagctct ctcatggctg aaagcgggta tggcttagca gggtgggaat   2220
gggataggcg aaatctatca atcagtaccg gcttacgccg ggcttcggcg gttttactcc   2280
ggtatcatat gaaacaatgg agtaccgcct tccatgccgc tggcgcggca tctgttaaca   2340
atcaatactt ttatcattat tatcaggaaa aaattgatcg tctgaataaa aatatatgaa   2400
tgataaaaaa gagagataca tatcttccga gctgtcagat aaaactcaac tttctgtttt   2460
gcgcagtata gttggatggg gctatgaaaa aataagacat tctctggggc gaccagggca   2520
acttgaaaga gcgattgcat ccggggagtt aatcccgtgt cctttaaaaa ctcctgtcga   2580
tacactatgg acgcgatcgg tgatttactg gcaggactgg atatccccat catggatacc   2640
atctgattct cgccaatgta cgatagattt ctataagcca ggctactatc gtggtttaga   2700
```

```
acgatgtcat atggttgttc ccgaagttca gaatctgatt agcaaagaag atattcctca   2760
tttttcgtgt gatatcaccg atattcaggg tatctccgca tcgaaatctg agatgtatga   2820
tattggtgac atttatgaat ttcctctact gagatgccct gggctggtta ccccggtaaa   2880
tgaagaacat ctcagagaaa atatgcagta ctgggagtta aggctccatc gaatgcgctt   2940
tgctgaatat ccgtggactg agcgtaagct gtattggctg aatgaaggtg gctcacatca   3000
ttttgcagct gcccgttatc aggcatgccg tctgggaatt tctgttccgc ttacgggcag   3060
attgagtcgc ttccatgtaa acatgcagat ggtttcagct ttatgtcagc aatggcacct   3120
gtttgctatt cctgcagatg aacggttagc ctgctttttc agggcgatga ttgcctttga   3180
atgcccattt ggtaattcag aattacctcg gaatatgcac aatactataa agtcaggagt   3240
caaactcaaa ctcgtttggc ttgaacgtgg tcataccaaa gcagacattg ttgcagatgt   3300
acttgccaca gcaggtttcc ctgattttgg ggatcaattg aagctgctgg ctaccagcag   3360
cctgcaaaaa acacataagc tggcctgaaa ggaatacttc acaatgaata tcattgtgtt   3420
ggtaacctgc tgttatcgtg atgaaattac cgctcaattt tttcggttga cgcggtctgt   3480
tcctgcatgg ttttcatctt tagcttctgt tttttcccta ctgccagcca gcgtctggca   3540
ttctgcgcat cgcattctga tacctgacct gctggtagtc catccagtcc ataacgaggg   3600
atacctgcga cagcagtacg cagcagatat acctgtcggg tggtgatgca ggatattgca   3660
caggaccatt catccagtgt cagttctgtc tcagggtgtt ctgtcaggaa tgcggcaaaa   3720
tcattggtta tgccaatttt cagtggaaga aatcccccgc tttctgcgcg aagatgggga   3780
aacagagact taactttttc cacgcaattg tgagtaaatt catgagtcca atgaggctgg   3840
cgtggaaaac ggcgtctttt tctttttttc ttactggcag aagcttcagg gggatgagta   3900
tcgacggcag gagaactgct tcccacagat actggatctt ccatctttac cgtctctgaa   3960
cgtgcgataa cacctgtttt ttcagataag gaagggggta aaagagtgcg acgtttttttc   4020
accataatga tgggtgtttt cttttcttcc tgatatttcc ccataaaaac ctctacgatg   4080
tgttcttata taataatata tatcatattt tcacaattaa cataatatct tcgttaagaa   4140
aataacagaa caaaatttgt tgttttttta tgacaggcat gaaatgagcc agcataatta   4200
tattaatcat tatcccaaat gagcttttgt atttgctcat tcgggatggt tggatatttt   4260
aagttatatc tactgtatca ttctcaggta atcgttccat taaatcagaa actacgggct   4320
gtaaccagtc agtgacttca cttacatact gatgccattc gggatgcctg gaggccagat   4380
ccatcactcg tgttaacccg gacggacgat caatgcccaa tttagttaaa atgttcgaga   4440
tataattatg agcatcaagt tcaactctga tatcccttgc tgcttctatt atttctaaat   4500
attctccacc caatccgtcc agtgggacat ttgtaataag ataatgaatg tattgttcag   4560
gcttaactcc atttgggaga ttaaattgtt ttattttttcc ttccgctgcc gcttttaact   4620
cataagttcg tgattctgtg ccggtgaaaa ctttatcaag agcagctttc ttttcatttt   4680
ctgtggagta tttatcgcca tcaagaatat aaagtttatc agatagatta tctccacgaa   4740
taagtgtact ggcaagtaga gtgaatgcgt ttgaagctgc gccaaattta aatattttca   4800
catatctgct ggccttaagt gaagaacata ttttatttat tattgcaaca gcaagatcat   4860
cttccacata tatttcaatg ggagttgttg atttacctgt taatctgttt atagcatcag   4920
gttttgtttc ttcaaatgaa taactacggc cttgaatgtt tacgacgtgt cttatattta   4980
tcttgtctga taaagtggtt accatttctc tatgggtagt gaagatgatt tgtttatttt   5040
tatcttcggc atgagttgat atgacgtcta ttaacttttt caatgcttcg tcatgcaaca   5100
```

```
gcaaatctaa ttcatcgatt aatattaagg cgttcttgtc cgcttttaat attgtttcca   5160
gaattaaaaa tatcttttgc tctcctgcgc tcatacttaa tgatgagtag gccagtccct   5220
ctgactcaac tccaatcaat atttttccat tgggttgttg atgttgattg aaacttgtat   5280
atggtttatt aagtatatag gaggcgtaat gaagaatgtt tgttattaaa tcattactga   5340
cactgctggt ttcatactga atattattct ttttttctga ttctattata ggaacacatt   5400
tatcaatgcc aagatagtaa acttctctta aaggacgacg agcataaatc tgaatccatc   5460
gtgagcctcg aacatcagct tttccataat tttttaattc attttcaatc attacaccat   5520
ctttacgata agttaaattt acaatgaagt cactgccgtt ccattcagca tgtggactgc   5580
gtggaaaaaa atgcattaac cgatggtctt caccggggaa acctttttca ggcatgtata   5640
tgcttgctat ggcatggagt attgttgatt ttccgcttcc atttggacct aaaattgcgg   5700
ttaacgcatg aggtttaaaa ataatctcgt ttaatccatt tatacatttt agtttgttaa   5760
ttttaatgga gttcaagact tgaccagtaa tagtttttttc ttttttctg ccatttttaa   5820
atcctagcat tatgttgggg gaattcacca tgtaattcag aaacatataa ctgtgaacag   5880
gggatatatc aaatcctttt aatattctat tttgcacagt attctacatc aggcctcttt   5940
tatgctacag actttttgag atgtctgtaa ttttagactt aatgttatga ctgatcatat   6000
ctcctatcca ctggtggcgc aggaaagtta accggctgcc accatgggat gatgtgtaaa   6060
ccgtgcacag gcgtgttctt acggagcggc actttcattt atctgtacgc gaacctccat   6120
tccggcatca tgacaggcct gcagccactg cgccacttcc agcggatcgc cctcccggcg   6180
taccaccctg ccttctttat tccataactg cagacaggtg ctgccgtcga gacgcaccac   6240
aaaatcccca cggcaggcct gatacgtcat gccgttcagc tccaccgcca gatcagtggc   6300
agaagtgcct tctgcgggca gacctgcggc cgggaccagc ggtagtacga cgacttctgc   6360
cgcacgctgt tctgcccgga ggcggtcctg ttctgcctgc agcagaggct gtgccacggc   6420
ccggccggcg tccgtcagct cgacagccag ctgcagattc ggggcgcgca gggtacgcag   6480
ccagccggca tcctccagac gacggcagga cgcgcgcagg tttggcccgt agatcggggc   6540
ttccccgctt cgctccagca cccgttccag gtcccgcgtc agcacggggc ccggccgttt   6600
ttcatcaagc gcagccagca caatcagcac tctccgctgc agtggcgacg gtcggcggct   6660
ctgggtcatt acctgtcatc ctccggccag atgaggtttc tgaggcgctg aaagtcggcg   6720
tcaatgagct cctgtctctt tatggcattc attgaggcat agccatttat ggccagttca   6780
tgccagaaga tcagcacggc tccggctttg gctgactcgc agagataaat cgcgccctgg   6840
ctgtccagat tgcattcccg gatgcgtcgt tccgcaaacc gggtcagttg ttcatagctg   6900
agtgaaaacg tcatttcctg atccatcctg cacgctccat ctgataatgt tctgacaggt   6960
aaaaatcata tcatgtatga tttatgtact cttgatttct gataatatca gatattgttt   7020
catttttaat gatgaaaatc atatctgata tgattttatg tgtatttctt aattatcata   7080
tcatttgcgt cttttctgcc gcgcagatcc ggtttccggc taacacggag ataataggtt   7140
aggtggttct gttgttaggg tatggagaac atttctcgag ccgagcaagg gaaattactc   7200
acaccatttg ctatgctaac ggccacacta accagccttt tttcggggta atacatgccg   7260
ttagcacaac tgaagcgtga cactctttcc cttgttaagc taaatggcga caggactgat   7320
gggataaaag gaagtgttca aaagaataag attttcatta gccggagcga tattgctatt   7380
gaaaaggggg atctgcttat acgcagtatg ccgcatggcg gtactgaaga atatattgta   7440
```

```
atcgaaccta acttcagaat gggtgtaggc ggtattcctg cgacctatca ggctgaggtg   7500
atactgaagg aaaatacaac taccgaggaa atgacatcat ccccttccac agcagtaccg   7560
gaagcagtta ttgccactgt aaatacattc attgctctgt gtgtcaccat tgtaaatgag   7620
ggcgcatcaa gtcctgataa atatgcttcg cagttttatc gcttgcgtca ggaattactt   7680
gaactcgata atattatcac cattccttca tggatcagat tctccatgtc acccgctgac   7740
attaagaata atgttggttt aaacgtcaca ggtggcgatg gagcttgggg gcgaagacga   7800
cagtatttac agagcgaatc tattaaaata ctttcaagct ataaaaccgc accaattatt   7860
gagcattctg ttagtgagaa taaaataaaa aatactgagc aagtcagcgg gttgacaacg   7920
atggcaagcg atgcagggtt aaacatgaag aagaaagtat tcattgtcca tgggcacgat   7980
gataaactaa aaaacgaggt ttacattttt ctggcaaatg aaggtttcca gcctgtcata   8040
cttcatcatg aagccaatga aggacagacc ataatcgaga agcttgagaa gcatatcgac   8100
actgtatcct atgcagtggt gctttatact gcctgtgatg aagggaaagc caagaatgaa   8160
actgaactaa aaaaaagagc ccggcagaat gttgttttag aacacggctg gctcatgtcc   8220
aagctatcgc gtaaattcgt cgctgcgata gttgaagatg gcgttgaatt tcctggagac   8280
ctgtccggag tggtcagaat atctgcatca gactggaaat atgatctgtc taaagaatta   8340
aaagtgctca ataattaaat tgtattcagt gatgtaagga tactattatg ggatacacca   8400
gaaatcagca catgctctca cagtggtttc tcaggaactt ccgcagtgat gatacggcac   8460
agagtccgaa ggagaagcaa cgggtctggg cccacgttgt ggttcctacg gcagaaggca   8520
aaaatgacat aaaggacatc ccgctaccga tatccagcgt ggccgtctgt aaggactgct   8580
ttcgtcttac cgacggtgac acaggcgagg tttttgatat cgagcatgag ctcagtgatt   8640
atgaacagga tatggctttg cttgtccggg atctggttca gaaccataat ttcgcgcgtc   8700
tggctaactg tgacactgat gattttccgg tagagaagct tgcaagtttt gctatatttc   8760
agatgttact taacctcaat aacccgcaaa gcagatttcc gggtaaaaat gagttatttc   8820
agtcattcat taacctagta aaaaacaacc ttcagcatat catttccgaa acaatttctt   8880
tgtctgacgt tatgccggag ttggcggctt taagtatcta tcagaaactg attcgtatag   8940
ctcgttcttc ttctggggat gacgaaaaag ctaaggccat gtttgtatta ttttcccttc   9000
tcgcacttca gggtaaaata acaatgattg acactatggc ctggctacgc ggagaggttt   9060
tttccggaat acatcgtgtg gatatatttc ataccgggca ccacttttac agtacagaac   9120
cacgtccggt atttacagta tcacctaatg tattttgcaa aatgacagaa gaacgcgtcc   9180
tgtaccttcc ccttgctcat aatttggctc ttaagtttta tcagtacccg gaacacgggt   9240
ttttcacccc actggaaatt aatgtattca gcccggaccc tcagaaacta cttacaaaag   9300
acatgtcacg aatcaaagtt tataaatgct cctatgatta tattgatcag gttatgtcaa   9360
caattgatat gtataacgtc ggattttcaa atattattta ttctagctgg cagctcagtg   9420
atgttgaaaa ttatctgagg ctacagaacg aacatcatga tacttattat cttccggaac   9480
atcccgtttg ctggactgta tccagggaga aagggtgatg gccctgaccc cggaacagat   9540
aagttgccga cagcagctcg tggcaatggg tgacttcaat gcccataccc tgctgcccgg   9600
agaggagtgg accaggccag aaaacgctga tgtccggcac gttctgtcgc tgatccccct   9660
gacggacatc cagctggcta accggctgga tgtggacgaa cgcaccatcc gcaaggggaa   9720
atccggcgag accagtatgg tattcaccac ttggtgctgc ctgtgctggc tggccgggct   9780
gggaatgctg ctggaagaac cggcttagcc ggttctgatg cgtttccaga ttcttttgag   9840
```

```
tatgaagcgt cgctgatatc gccattgtga acggtagata tgggggagtc gatcatagtt   9900
cttccaaaac aaggtccagc ctttataggc atcaacaagt agggcaatga gagagccagt   9960
ttttaagagg ccaaagaaaa cggccatgag aaatacagtc atacgatgtt ccttatgtaa  10020
aactgtattt aggaaatccg aagcggcctt taaggccggt tgatgaaaat gaactgaaaa  10080
aagtttctct ggcctatttg ttgccatttc aggctagctc tttcgtgaat tttgcctctc  10140
aggcaataat ccactcatca caacaattca ccgtttttag tgcttatcct gcaaaaatct  10200
gtttttttcc cttcctgaga tccgaaaact tatttaagag gatcacttgc agccggcaac  10260
aggaaggttt tacattgatt tgaattatgc cgtttctttt cctcctgcct tgaaaaggat  10320
atctgaatgc acttttatgt ggatgaaaca ggccagactg gccgaaacct ttttgacaaa  10380
acccagccaa tcctctccta cggagttctg tcctcagagg ctgacctaga taaggttgct  10440
gaagcggatc ttgccgcatt acgcaaaact ctgggcgtgg agcgcctgca cgctgcggaa  10500
ctgggcgtgc accgcctttc agaagttgtg gatacgctgc tggtcctgca gaaaaatcac  10560
cggatacggt ttgatatctg gcaggtggtt aagcgcgatc acgccattat ttcgttcttc  10620
gaccaggtgt ttgatcaggg actgaatccg gttgtgccct ggagtgccta ctggacccct  10680
ctgcgctatc cctgctgct gaatctgtct aatctgtttg atgatgagct ggctgaaaaa  10740
gcgtggcgtg cccgtcttga ggctcatgat gaacgttctt gctcattatt cagtgaggtt  10800
tgtggagtgc tgcttcagcg cgttcactct ctgggtgatg cccgttcagt tgaactcatt  10860
accgatgccc tatcttgggc gatggtcaac tttgatgagc tggggtacaa ctgcaaaacc  10920
aataaggaaa agttgcagat catgcccaat atgattggtt ttcagtccgt tttgcacggg  10980
atctgctctc gtctgggggc accgaaccgg aaagcagata tcattgttga ccagcagtca  11040
cagttcaaca ccacccagcg ggagttgaac gagttttact accagatccg cgaacagccg  11100
tgggcactgg ggccgggttt gcctgtcatg gatatgaaga acatgccagc aaaaccgctt  11160
gtcttccagt cgggaacgat gagtgccggg ctggaactgg ttgatattta tctctggatc  11220
ttcaaacgat acatggaacg gaaggaactg accaaacccc tctcccgcct cgtctacacc  11280
aatcttaaaa cagcgagaac tgacagtgtt tctctgcagt cagttgcaaa gaggtttaag  11340
gagtttttg aaaaactttc tgaaccaacc gcagaaatga tagaaaaagc aaatgaactc  11400
agggccgtgg aagaaacgcg ccgtcttgcc catcgtgtac aaagtgtgtc gcaatcctga  11460
tcagaaaggt taaccgcata tgaaggcaga aaatgcccgt caggttcagg ggctgataga  11520
actagagaaa tttaaccctg aaacactgtg ctcgggcgag agctggatgg caccttcagc  11580
cagtgaagtc agcgtggtcc gggcgctgat cccgctcaca gatatccagc tggccaaccg  11640
gctagatgtg gacgagcgca ccatccgtaa gtggaaatcc ggcgagacca gaatggtgtt  11700
caccacctgg tgctgtctgt gctggctggc cgggttgggg atgctgctgg aagaaccggc  11760
ttagccggtt ctgatgcgtt tccagattct tttgagaatg aagcgtcgct gatatcgcca  11820
ttgcgaacgg tagatatggg ggagtcgatc atagttcttc cagaacaagg tccagccttt  11880
ataaggctcc gtttcccaaa cggagccctg agtcgctgac gccggaattc tttactacga  11940
attagtattg aggcgagcgg ccaaaacaat atgctgcata tcctggtgcg tcggcttaaa  12000
gcccagacgc tctaggttta tttcagcaac cacttcatct gggccacccc agatagtatc  12060
gccagcctgt tccagtaggt cgagtttgcc acaataagct tcaggcttac cagcggcatt  12120
tagctgatac tccagttttt ccccatgaat tttcatgacg ttaatcagca cgtcattccc  12180
```

```
cagagccata tagagccaga tatatatgcc gccagcggtc tgctgcgtat cgcttacaac  12240
gacaccataa tgtgccatga ttagccggta tacgtgctgg gacagtttta ctgccctata  12300
ttcatcgccg acaaatgcac tgataacctg cggaatacga tcaggaaaac cctctggagc  12360
ttccagagca aactcaagca tatagtttgc ggaaacttca tttgactcga tatgacgcaa  12420
gtaaagacgt gcttgttcgc cgatgtcttc aagaatgacc tcgtgcttaa agcctgcgtc  12480
gtcagtgatg ttttctaatt tttggtagga ctggcccgct tcattgagat cttcaggcca  12540
gattaatttt ttatcgtgtt cgcgtattat cagtggtgac atgccagatt accgtgctca  12600
ttccattgaa aaaattctat cgcgcggcgg ctgaaatcag ccagattcac cgattttgat  12660
agctcggttt ctttctgttc tatgcatttc ttacggccat cttcttcaaa ctgaacaaca  12720
accagcggca caacacggtc gcgacgggtt gcttgctgcc agttttcatg caccacgatc  12780
agcatcggac gcttctcgcg ggtattattt gaacgtactt cgaatttacc ctgaacgcca  12840
ggtatgcaaa aactacccaa aagagcatag ttatcagcaa tagtgaatgg tgaatgagtg  12900
atcattggca cctccgcaaa ttcaaagtat tcagtaagat ggcggaaacc cttgacgcgc  12960
aagtggttga cgcttacgtc agtatacctc atagaaatat tcggacaata atattgttta  13020
cgatttcagc ggcgttcgta taggaaaagc cattcctcag gatggctttt ctcgtttcag  13080
aacgtcagaa aacagaccgt tctgtgggcg gcaggcgcag tgcttgccgt atctggtcga  13140
ccatgtccag aaaatcccct tctttctgca ggaagaacag ttctttatgc actctgatta  13200
gcgtcggtaa atcgcggcga gcagcctcaa tgaagagggc aaacgccagt gacgtgccat  13260
gcgggatatg ggtgatgcca ggtagctgtg cggcgcgcag ttcaagcagg ggaacgccgt  13320
tacgcataat atgctgcaga tcttcttctt tataaatgcc tagtaaacgg caccaggccc  13380
ggttttcagc gagcgtctgg gcgctgtcat accagtaatc ggcgagggct gccttcatca  13440
ttgtggccac gtctttatcc atcagcgcca cgaggccatt tccgcgcata aagttaccga  13500
tcagatcccc gaaggaggct gagaggaatt ctttgacaaa atcacttttt gactttcctg  13560
ccgccctcgc ctgttccgtg atttcgttat ccacatcaaa aggcatgttt cgcacggtca  13620
gcgtgcgtgt ggatcctttt tcggcatttt cattctgttc agtcatttct ttctccgaag  13680
gacgtgacac tctcaacatc caccacttgc attgaaataa gatgtttgtt gttaagatat  13740
ttattttgct tcccgatttc aatatgtgaa ttcataatga taaaagtggt gctaagcaag  13800
ataaaattta accaggcgtg aggagaactc ctcatcttca gcactgagat ccgaaaaccc  13860
caagttacgg atccgcggat ccttcgctgc cgcccgctgg tccgctttca caggatgtgg  13920
tgtcccgctc cgctgacatg acactgtatg ttgtgtttct tcccgtgttc ccgagccagt  13980
catcagcggc agaaaagatc gcttcgctta ttcactgatc ctgattcact tccggaaagt  14040
tgtaaatacg cagtaaatcg gatcatctga aaaccactgt tcgataattt aatggagtgg  14100
ttatatgcct gattattatt tcaatatgtg aaatccattt ttgtgaaagt cactttctca  14160
acagagtagc actcatctgg cgatgattga ggtgtggtaa aattgcacgg ctaactattc  14220
aactgaggaa atgacatgtt tactgcattc aatgagagaa atgatttcag ttatgctttt  14280
gaaaaaattc gcaatgcgat ttccgcgcca ggagaaaata atgtttatgc tgccacagaa  14340
ttaggtcttg gcattctgct ccgtaaatac gagcagtttc gccgggagct ggatgtggcc  14400
ggtgagctgg gaaactggga atacgatctc gatacctaca atcactgtat tgcggtgctg  14460
caacgttact tcactggcaa tccatccgga ctgacagaac gtgacgcccg gatttacagt  14520
cagtacctgc agactgagca caaagggttt gtgaagctgg ctgaagaact ggcggctgac  14580
```

```
cgctgaatac atacagtagg cgggatttcc ggataaggta ccgaaccggg gctgttaaaa  14640
gattctggag ttgaaatgaa aaagggaaaa acgttagaac cggggctgct ggccagcgac  14700
agcgactggc acaataatgc ctgcctgaat tacatgccgg atcatggtac agcttacacc  14760
gaaggttaca ggcgagctgc tgatattctg attaaccaca ttgatgaatc cgggcgggac  14820
caggattttc tggtttatcc ggtgttgttt ctctaccgac atcacttgga gctccttatc  14880
aaacaaatta tcggactggc ccttgcactg gcagaagacc cggataaaca ccagtacaaa  14940
aaagatgacc ataacctgaa taatctatgg ccgctggcac aaaagctgat cctggaagtt  15000
gatgacagct accggccttc cgattttaaa atcgtcaaag aggtggttaa agctcttcac  15060
caagcggatg aacgggcgac agatttccga tatgccagga gaaatgacgg cacccggagc  15120
cttgaaggaa ttcattacgt caacacccgc cgctttgggg aaaaaatggg agaggcttcc  15180
gatttacttg acggggtcga caatagcctc cggtacctgc tggactgtaa agccgaatgg  15240
aatcaaattc tggacagctt ctgacagcca gaaacggcgc gaaaaatcca tcagacttac  15300
ctgaacaact aatgatactg agataccgat catgactggc ctcatacctt cagctacttc  15360
tcagggccca atggccgccc tgccagtgac catcgactat cccgcagcac tggccttgcg  15420
gcagatggcg ctcgttcagg acgaactacc gaaatacctg ctggcgccgg aagtgagcgc  15480
cctgctccac tatgtgcccg atctgcaccg taagatgctg ctggccaccc tctggaatac  15540
gggcgcccgc attaacgagg cgctggcgct tactcgaggg gatttttcgc tggcaccgcc  15600
atatccgttc gtacagctgg ccacgctgaa gcaacgtgcc gagaaggctg ctagaacagc  15660
aggacgtctg cccgccggca gtcaggccca tcgtctggtt ccgctatcag acagccagta  15720
cgtgaaccag ttggaaatga tggtggccac gctgaagatt ccgctcgagc gacgtaataa  15780
gcgtaccggc agaaccgaaa aggcgcgtat ctgggaggtc actgaccgga cggtacggac  15840
ctggctgaat gaagcagtgg agaatgcggc cgctgacggg gtgtcattct ctgtgccggt  15900
taccccacat actttccgcc attcctacgc gatgcatatg ctgtatgctg gtattccgct  15960
gaaggtgctg cagagcctga tggggcacaa gtcgattagt tcgacagagg tgtacacgaa  16020
ggtgtttgcg ctcgatgtgg cagcaaggca cagggtgcag ttttcgatgc ctgagtccga  16080
tgctgtcaca atgctgaaaa acagacacgc ataagtcaca aatcataatt atgaattgtg  16140
atttattcta taaaagaaga gaccactgca atatgtgatc tcttgtatgc aagggtgctt  16200
aaacagtgtg aattcacaag tgtgatttca taagtaataa cttcttgatt attacgttag  16260
tgtttttaag tattgctcaa gggctactct gacgatggca cttacatttt ttggatcttt  16320
accattgcgt ttattcctca atgccagatc ttctattgtg acaagcatgc tttcaccaag  16380
agagattgtc gtccgacatt gtttttctgg ttcgggtttt tccggcgcgc cgtatggttt  16440
atccgcaagg cgctgagcca gagcctctgc ttgttctacc gtaactgcag ctctgtttaa  16500
tgcttgctgg ctgggtttct tcaccatggg ccaaatacct cattcattaa atgttcaatt  16560
tctgctctgg ctgctgtatt gttcgtttct actacaccgg tgccgttgct catgcaatcg  16620
cgatagactt ttctgaaaca aataactgaa tccaggactt gaattgttgg gaattcttca  16680
agatattcaa ggaattcttt tctctcattt cccctcaaaa ccggattggt tgttgccata  16740
ctttgtaaac aataaacctt aagttccggg ttaaggttac gcattgcgtc tatctgttgt  16800
tctagttctg taagagtatc cagatctggt tgagaacact gtagtggcgc aattatttga  16860
tgtgcgacaa ctccactcgt tatgaattcc tttgagtttc ttcctgcgac atccactatt  16920
```

-continued

```
acatcatcga acttttcatt cagagcctgt agtgtttgtg tcaggttatc aaatttctca  16980
acaagggtta ttgctggtaa cagtcctgca gcttctcgtt ccgcatgatg ttttgcggct  17040
gttcgttgta gatctccgtt taacaggcag acttcctttc ctttatttgc gagagcaata  17100
gccaggtttg atgcaatggt agttttccct gaaccacctt tgttcccacc aactacagta  17160
atcattgcaa cctcataaat gtgatgtgtg aagtatgatg atattttgac acggtaacct  17220
gatgtgtcaa catgcattca tatttatgaa gtatgaaata tgaagtatgt catgtgatgt  17280
aataaatatt acttgtgttt tgtgatttca taactatgat agtgctcaaa ttgagtatta  17340
ccttgcaacc agaaacagtg atttactcag attgagtatt taaggggcta tagatgaacg  17400
tatactgcga tgatggttca acaacaatca agttggcatg gaatgacaat gggaaaatct  17460
gtaagtcgtt gtcgcaaaac tcatttcgtc atggatggaa ggttgacggg ttagggattc  17520
gccagacatt taactatgaa ctggatggta aaaaatacac gtatgatgaa gttagcaacc  17580
aatctattct tacgactcat attgagtatc aatatacgga tgttaacctg ttagctgtgc  17640
atcacgcttt actgaatagt ggattagcgc ctcagcctgt atcattgact gtgactttgc  17700
ctatcagtga gttctacacg aaagagtgtc aaaaaaatga actcaacatt cagcgtaaaa  17760
ttgagaattt aatgaggccg attcgtctta ataaaggcga tgttttcacc attgaacacg  17820
ttgatgtgat gcctgaatca ttgccagctg tgttttctcg tctggtcatg gataaagttg  17880
gtcagtttga aaaatcgctg gtagttgata ttggcggcac tacgcttgat gttggtgtta  17940
tcgttggtca atttgactct gtaagtgcca ttcatggtaa ttctggcatt ggtgtgtctt  18000
cagttacgaa agctgcaatg agtgcattgc gcatggcatc cagtgatacc agtttcctcg  18060
ttgcagatga attgattaaa cgtcgtaatg acccggactt tgttcggcag gttataaatg  18120
acgaaacaaa aactgatctg gtccttaata ccattgaggg ggctattgcc agtctggggg  18180
agcaagtagt caatgagctc ggtgattttc atcatgtgaa tcgtgtttat gttgtcggtg  18240
gtggggcccc gttgatctat gattcgataa aaacggcatg gcaccatctt gggcaaaaag  18300
tagtgatgat ggagtcgcca cagacagcac tggttgaagc tatcgcggct ttcaaagagg  18360
agtaatattg tggacgatga acggaaaagg aaaaaattca cactttatct gcatccggaa  18420
aaagctgcag actttcaaac tttggaagcg atagagtccg ttccgcgttc tgagcgtggt  18480
gagctgttcc ggaatgcatt tatttctgga atggcgttac accaacttga tcctcgcctg  18540
cctgtattgc tgactgccat tttgagcgag gagttttcag cagatcaggt tgtaacctta  18600
ctcagtcaga cgacaggatg gaagccttct caggccgata tcagagctgt gttgactgaa  18660
ctcggtgctt tgcaatctgc tgaaaaaatg cctccttctg ctactgattc ggtgcaggag  18720
gcaatgaatg atgtgcgcct taaaatgcaa aaattattct gatatatcag aatgaagcaa  18780
tggggatctc agtccattgt gttgtatacg aaggcgagag catttcccgt ttcatttgcc  18840
attcaggggc ggttcctcgc cccgcaaacc acactttccc ttttccagac tggttcagtt  18900
catcgagtgt tttcattaac ttttcgctgt ttttacgggg ctggatctca tcaaataatc  18960
ccggctgcgc tatacccgat ggtgtgaaat cagccagcat gactcctgcc ttcatatagc  19020
ggtacccttc acgccagaca tggtttaacg ctctgcatgc tgcggcaata atgtcccggc  19080
tgtcctgtgt gggtaatgga agcttttcca cagcggcatt gctgtaacag agttctttta  19140
ctgcaaaggg ggatgtccgt acaaatgtcg tcacctgccg gcaatactga cgctccccac  19200
gtagtttctc tgcggcccgc tctgcatact gaacaacagc ctggtgcatg gcatctttgt  19260
ctgtgattcg ttcaccaaaa ctgcgactac agacaatctg ctgttttgcc ggtggtgctt  19320
```

```
cttccaggga tatgcaggac tcgccgttga gttcgcgtac cgtacgctca agaatgacgc  19380
tgaagttttt ccggatgaat gccgtgttag cctgcgccag ctgcagtgct gtgttaatac  19440
ccagcgcatt cagcttttcc gtcagtctgc gtcctactcc ccagacctca ccaactggct  19500
gcagccccag tagcttcaag atccgattac ggttttctgc cgtcagcgcg accacaccgg  19560
aaaactgtgg ccattgcttt gttgcccact gtgcactttt agccagcgtt tttgtaggcg  19620
caatgcccac ccccatggtg agtcctgtcc agctctttac ctgttccctg agctgatgac  19680
caaaaacctc cggagagatg caatgattta tcccccgcaa atcaatgaac atttcatcaa  19740
ttgagtaggg ctcaactgcg ggagaaagcg actccagaac agccataacc cgttggctca  19800
tgctgtggta cagcgcataa ttgctggaaa atacatgtat tttcttctcc aggcgcatct  19860
gtctcacctg aaaccagggc tgccccattc tgatgccaag ggcttttgcc tccgggctgc  19920
gcgcgatcac acagccatcg ttattgctga gtacgattac cggttcgttg cgaaggtccg  19980
ggcggaaaac tttttcacat gaggcgtaga aactgttgat atcagccagt gcaaacatca  20040
gcgtaactcc cgcgtcctgt gtatcacgtg agtgacaaca ccaaaaatac agatgttttc  20100
cggatacagt gtgcggaact ccgggctgtc tgaaaccggc tccagtgccg ggcgtgggcg  20160
caacagcagt cgtttgacgg tgaactcacc gtcgatctca gcgataacga tgtccccgtg  20220
ttgtggtttt tcggccctgt ccactaccag cagatcacca ttctgcacgc cagcctggtt  20280
catcgattca ccgctggcgc gcagaaagaa ggtggctgca ggtctgctga tgcaatagct  20340
gttcagatcc agttcctgct cagcataatc agtggcaggc gaaggaaaac cggcctggca  20400
acgatcggca aacaacggtc gcacgtaact gtcatcgcct gaagggtcag ccggacggtg  20460
ataaacggta ctcatgctgc aggcagccag ctgtcgtcct gccagatttc ttccagcaga  20520
gacaggatac gttctttatc cttgtcgttg cgggctcctg tgacagatac agacggggcg  20580
ctgccctggt ctatacgcag ccagatttcc gggtagtgtg gtttcagacg ttgttcgatt  20640
tcattctgta gcgcctgaag tgtgcctgat ttgaggtttt ttgtgctctg gcggtcgaaa  20700
agaatttcaa tgcggatcat gttctcatct cccttttctt ttgctgtatg catatacagt  20760
atcctaataa ctgaatccac acacagtcaa atgtcattgc tctgactaaa aaatgctcaa  20820
ttctctgaga gtgtggctgt atgcctgctg tggagtgctg tgtccagctt atccacagca  20880
ttttgtgcac ggttctgtgg acaaaatacc tggttaccca ggccgtgccg gcacgttaac  20940
cgggctgcat ccgatgcaag tgtgtcgctg tcgccggcct cctcacccgg tcacgtttcg  21000
tcgttcctcc tccacgcgct gcggcttcgg ggccgcacct gcattcgtat gcggtcgccc  21060
ggttacaggt gcggcacggc ctgatggagg ccgcatgtga gaggagaatt cccatgccaa  21120
actggtgctc aaatcgtatg catttttctg gtgaaccagc acagattgct gagattaaac  21180
gactggccag cggtgcagtc acaccatttt atcgccgcgc cacaaatgaa ggtattcagc  21240
tgtttctggc cggaagtgcc ggacttctgc agaccactga agatgtgcag tttgaaccgt  21300
gccccggact gacggctgcc ggacgtggtg ttgtatcgcc ggagaatatc gcgttcaccc  21360
gctggctgac acacctgcag aacggtgtgc tactggatgt acaaaaactgc ctgatgctgc  21420
atgaactctg gctgcagagt ggtactggcc agcgtcgctg ggaaggatta ccggatgagg  21480
tcagggatac catcaccgca cttttcaccg caaaaagagg tgactggtgt ggcttctgga  21540
gtaacgagga tgtatcggtg tggtggaacc gtctgtgtga caacgtactg ccggaaaaaa  21600
ccatgccgtt tgacctgctg acggttctgc cgacccgcct ggatgttgaa gtgaatggct  21660
```

```
ttaacggtgg tgttctgaac ggtgttcctt ctgcatatca ctggtatacg gaacggtatg  21720
gcgtgaagtg gcctgtgggg tatgaggtga atatcagtag tcaggaagac aacttcattc  21780
aggttgattt cgacacgccg tggtgtcagc cggaaagcga cgttattgca gaattaagcc  21840
gccgtttcag ctgcacgctg gagcactggt atgccgaaca gggctgtgat ttctgtggct  21900
ggcagttgta tgagcgcgga gagctcgttg atgcgctgtg gggggaactg gaatggtctt  21960
ccccgacaga tgacgatgag ctgccggaag tcaccggacc tgcgtggata gtcgacaatg  22020
tggcgcatta tggcggatga agtatgacgg agacgggcgg gcaaccgccc gtttcttttc  22080
cgacaaagga tgtcgccgtg ctcctctttt tactgcgccg gctgacgcgg cgcggcagga  22140
acgctgcctg tggtcagtgt cccgcgtccg gcgggcacgg gacgggcgct tttaccgctc  22200
ccggctggcg tcggtgacag tgtacgccag cccgtcgccc ttttctgatg aacgcccttc  22260
aagccgcttt cgcggcataa ccttgccgtc agaaagacga cggctgcggt attccacggt  22320
cggcctgacc cgttaccgga cgcggtgaac agcccacagg cagcggggaa cgggcaccac  22380
aggggtgccc tcccggtgcc ctctgtaaga gaaggagttt ggtatgtccc gttttgtcct  22440
cggtaactgc atcgatgtta tggcccgtat ccctgataac gccattgatt tcatcctcac  22500
cgacccgcca tatctcgtcg gtttccgtga ccgttccggg cgcaccatcg ccggcgataa  22560
aaccgatgag tggctgcaac cggcctgtaa tgaaatgttc cgcgtactga aaaaagacgc  22620
gttaatggtg agcttctacg gctggaaccg cgtcgatcgc tttatggccg cctggaaaaa  22680
tgcgggattc agcgttgttg gtcacctggt cttcaccaaa aactacacat cgaaggccgc  22740
atatgtgggc tatcgccacg aatgcgccta catcctggca aaaggccgtc cacgtctgcc  22800
acaaaacccg ctgccggacg tgctgggctg gaaatattcg ggcaatcgcc atcacccgac  22860
ggaaaagccc gttaccagcc tgcaaccgct gattgagaac ttcacacacc cgaacgcaat  22920
tgtgctggac ccgtttgcag gcagcggctc aacctgcgtc gccgccctcc agtccggacg  22980
ccggtatatc ggtatcgagc tgcttgagca gtatcaccgt gccgggcagc aacgccttgc  23040
cgccgtgcaa cgggccatgc agcagggggc cgcgaatgat gactggttta tgccggaggc  23100
tgcgtaaatg aactatgcag gacacgaaaa actgcgcgcc gaagtggcgg aggtggccaa  23160
tgccatgtgc gacctgcgta caaccatgaa tgagatggag cagcggtaca gctttaatgc  23220
cgacaccctg ccggaacgtc tggtgcgtca gacgctgttt cgcgcaaacc gcctcctgat  23280
ggaggcatat accgaaattc tggaactgga agcgtgcttt aaagattgag aaggagacga  23340
gaatgtacgg aacatgcgaa acgctatgcc gggagctggc agtaaagtat ccgggagaca  23400
tgccgctgat gctggttatc tggtccccgg aagagattca ggccctcgct gacggaatgg  23460
atatttccct gtccgatcat gaaatcagaa ccgtcctggc gcgcctggag gacatcccgg  23520
aagaccagcg gactgaatcc ggtatttctt ccggcgtggc gatggagatc atcaataacg  23580
tgagcgaaaa ccgccaggtg accgtccctg ctgaactgct ggcgtccctg attcagaccg  23640
ctgaacaggc attgtggaaa cgtgaatggg ccgcccggga tcatggcctc gccgtcccgg  23700
aatgcgtcac ccgccgtcag gcggtgatta atcaggcccg caccctgctg aaaaacaaca  23760
gacacgaaaa cgactgatgt tatcgccgcc tccgggcggc gattcaggga gaacgattaa  23820
tcatgaacga aaacacaaca ctgaacgcac tgatttgtcg tcacgcccgc aacctgctgc  23880
tggcgcaggg ctggccggaa gagacggatg ttgaccagcg gaacccgaac aatccgggct  23940
ggatcagcat ttatgttctg ctggatgcgc cccggctggc gacgttactt atcaaccgtc  24000
acggcggcgc actgccgccg ctcctggcct ccgccattca caaactgacc ggaaccgggg  24060
```

```
cggaacttgt actgtccggc agtcagtggc agtcgctgcc ggtacttccg gcagacggaa  24120
cgcaggtgtc tttcccgtat gccggtgagt ggctggcaga ggacgaaatc agggcagttc  24180
ttgatgcggt acgcgatgca gtacgctgtg tcagttacca ggtggcagaa gatacgcggc  24240
gtatccgggc ggcgctgacc accaccggtc agacgttact gacccgccag acgcgccgct  24300
ttcgcctggt cgtgaaggag agcgatcacc cctgctggct cgatgaggac gacgaaaacc  24360
tgcccgtggt gctcgacgcc atcctgaacc ggggcgcacg tttttcggcg gtggaaatgt  24420
atctggtcag cgattgtatt gaacatatcc tgtccagttg gctggcctgg gatgtgctgc  24480
gtataccgga tgaaccgccc cgccgctggt ttgaccgtgg tgttctgcgg gaggtggtcc  24540
gggaagcccg gaacgaaatc cgcagcatgg cggatgccct ggcaaaaatc cggaaatgat  24600
gacactggcg gggtaaatcc ccgccttttt cctgccggtc cccggacaga gcacaaagga  24660
cgtcgccgcc ggctccgctt tacccggcca tgcagggcat ggccttgtgg tttttcagtt  24720
atgtggccgc cgtgtcgtgt gcgggctgtg ccgtgcctcc atcttagccg ggctggcagg  24780
gatgcaaggg tacgcttcgc cgctgcggtc acccggtccc tccttcccgt ctgccgtgat  24840
tttccggtcg ttcacccgct cagatttcgc ggtctcaccc tccaactccc gccagccgtg  24900
tgcgtcaggc tgcggcttcc cttgcgccct gtgcatcccc accttatcgc ccggctttta  24960
tggaggcacg gcaccgcccg gtgtcgcgga atatgtgaac aacggaggaa aacatcatgc  25020
aatatgcgaa acctgtcact ctgaacgttg aagagtgcga ccgtctgtct tttctgcctt  25080
acctgtttgg ccaggatttt ctgtatgccg aagcgtctgt atacgcgctg gcgaaacaaa  25140
tgatgccgga atatgaaggc ggattctggc acttcatccg cctgccggac ggtggcggtt  25200
acatgatgcc ggatggcgac cgttttcaca tggtgaacgg tgcaaactgg tttgaccgta  25260
ccgtgagtgc tgatgccgca ggcatcatcc ttacctccct tgtgattaac cgccagttgt  25320
ggctgtacca cgacagcggg gatgcaggac tgacccagct ttaccggatg cgcgatgcgc  25380
agttgtggcg tcacatcgaa tttcaccctg aatgcaacgc gatttacgca gcactggact  25440
gattaacgga cggggcggca atgccgcccc tgtaaaggag acgagaacat gtactgtact  25500
gttaaagaaa ttatccgcga tgtactggat acagacgtgc cggacagtga atgcgttttt  25560
gccgtggtgc tgacccgtgg ggatgtgcgc cacatagccc aggactggag tctgacagac  25620
gatgagctgg aaaccgtcat gcagcggctg gacgatgcct ttgaatatgg tgcggatgtc  25680
agcgttgttc acggcgttgt tcgtgaactg atggaagaaa agcgcgccag ccgtcaggtg  25740
acagtcccgg cggtgatgct ggaaaaagtg ttggcgctgg caggcagtga aatgaagcgc  25800
ctgtatgccg tcgggagtga gaacgggggc gacggtgatg cgttcgtcag ggaagaacgc  25860
gaagcaatgg acgttgtgtt acaggcgctg gacggggagc acatgtcatg aatatcagca  25920
cagaaacccg cgaaattctg cgcaattaca aagccgtgat taatgcgcgg cgtcgtgaaa  25980
tggggcagaa accgctcacc actgcgcaga ttgttgatga aatctgcgat tttgtggcga  26040
atcagcaggc ggttttcctc ggtggtcact atatccttca gggcagcaga aacaggtgat  26100
acagggcagg cggtggaggc cgcctgtcag cccgcgcgaa aacccctggc aggctgacgc  26160
ctgccggaaa tgcggggtgc agcgcctgcg gcgctgccgg cccggctttc cggtcagaag  26220
gtagtgtatg gctgtatgca gggaacaggt gtgatattcc gtgacactgt caccgtttct  26280
ggctgtcttt tattgcgccc acttcggctc ccggctgcct ggcggcatcc ggtcgtcagg  26340
cccgactccg acaggcagct gctggcgcac ccgccagtct ccgccgaacc cgctggcgcg  26400
```

```
gtttcgggct gccgctacgg tccgatgcgt gaaaacccgg cttgcagcga ccgttccggt  26460
cgcgccgccc ctgtcgcgcc gtgacctgcg ctccctgcac acctgacggt gtgtgaggaa  26520
actgcgcctg atggcgcagc agtcttccct cctgccgcca cccctgcggc ctgtttcccg  26580
ctgtggactt tccgggggc agacgtaacc ccctcccgtt ccatctgtcc agggtgagat  26640
gcaccggcca caaaattttt agccatgaac ccggctaaaa attttgcgtc cgcccccgga  26700
cagctgtccc gtgaggcggt aaacgggccc ccatcggaaa ggtccactgc ggggagaaac  26760
ccctgtgaag tggacggcag gaggagcttt cgctcctctg aaggggcaca tgaacgtccc  26820
gtcgccggta tccggtttat ctcacatctt tcagtcagga ggttcttatg agtgcacgtg  26880
gtatcaacaa ggtcatcctc gtcgggcgtc tgggcaatga tccggaagtc cgttacatcc  26940
ccaacggggg cgcagtggca aacctgcagg tggccacatc agaaagctgg cgtgacaaac  27000
agacggggga gatgcgggag cagacggaat ggcaccgcgt ggtgctgttc ggcaagctcg  27060
cggaagtggc aggtgaatat ctgcgcaagg gtgcgcaggt ctacatcgaa ggtcagcttc  27120
gcacccgtag ctgggaagat aacggtatca cccgttacgt cactgaaatt cttgttaaga  27180
ccacgggcac cgtgcagatg ctgggacgtg caccacagca gaacgctcag gcgcaaccga  27240
agcctcagca gaatgggcag ccacagagtg ctgacgcgac gaaaaaaggt ggcgcgaaaa  27300
cgaaaggccg tggacgtaag gccgcgcagc cagagcctca gccgcaaccg ccggaggggg  27360
aggattacgg gttttcagac gacatcccgt tctgatcggg ctgactgtga caaccgcccc  27420
gccctgtgcg gggcatcacc ggagatatga ggatgagcga atatttcaga atacttcagg  27480
gactgccgga cggctccttt acccgcgaac aggcggaagc cgttgccgca cagtaccgga  27540
acgtctttat cgaggatgat cagggaacgc attttcgcct ggttgtccgt caggatggca  27600
cgttgatctg gcgctcctgg aattttgagg acggtgccgg gtactggatg aaccagtaca  27660
tcagggattt cgggattctt aagtaagaga ggtgccggac gcgcgaacgt ccggcaggac  27720
ataagcaatt ataaggggat gattatgcct gtaacgaagt gtgaaccaga aaccacccgc  27780
aaagcaagcc gtaaatctgt aaaaacgcag gaaactgtcc tgtctgccct gctggcgcag  27840
acggaggaag tgagcgtgcc gctggcctcg ctgattaaat caccgctgaa tgtgcgcacg  27900
gtgccgtatt ctgcggagtc cgtcagcgaa ctggcggagt ccattaaggg cgtcggactg  27960
ctgcagaatc tggtcgtgca taccctgcct ggtgaccgtt acggtgtcgc cgcaggtggt  28020
cgccgactgg ctgcactcaa catgctggca gagcgtggca tcattccggc tgactggcct  28080
gtacgcgtga aggttattcc gcaggagctg gcgactgccg catcaatgac tgaaaacggt  28140
catcgtcggg atatgcaccc tgccgaacag attgccggat tccgtgcgat ggcgcaggaa  28200
ggcaaaacgc ctgcacaaat cggtgatttg ctgggctatt cgccccgcca cgttcagcga  28260
atgctgaaac tggcagacct tgcgcctgtc atcctcgatg cgctggcaga agaccgcatc  28320
accacagagc actgtcaggc gctggcgctg gagaacgaca ccgcgcgtca ggtgcaggtg  28380
tttgaagccg cctgccagtc gggatggggc ggaaaaccgg atgtacagac cattcgtcgt  28440
ctggtgaccg aaagtgaagt ggcggtggcg gggaacacta aattccgctt tgtgggggct  28500
gatgccttct cgccagatga actgcgcacc gatttgttca gcgacgacga gggtggctat  28560
gtggactgtg ttgcgctcga tgctgccctg ctggaaaaac tccaggctgt cgctgaacac  28620
cttcgggaag ccgaaggctg ggaatggtgc gccggacgca tggagcctgt cggtgagtgc  28680
cgtgaggatg ccggaacata ccgcagtctg ccggagccgg aagcggtgct gacggaggcg  28740
gaagaagaac gcctgaacga actgatgacg cgttacgacg cgctggaaaa tcagtgtgag  28800
```

```
gaatccgacc tgctggaagc agaaatgaag ctgatgcgct gcatggcgaa ggtcagagcg  28860
tggacgccgg agatgcgttc cggaagcggt gtggtggtgt cctggtgtta tggcaacgta  28920
tgtgtccagc gtggtgtgca gttgcgcagt gaggatgacg tggctgacga cgctgaccgc  28980
acggaacagg tgcaggagaa agcatcagtg gaggaaatca gtctgccgtt gctgacgaaa  29040
atgtcctcag agcgcacgct ggcagtccag gcggcactca tgcagcagcc ggacaaatct  29100
ctggcactgc tggcatggac gctctgcctg aatgtgtttg gcagcggggc gtacagtaaa  29160
ccagcacaaa tcagcctgga atgtgaacat tattcgctga ccagcgatgc gccatcgggg  29220
aaggaaggtg ccgcattcat ggcgctgatg gcagaaaaag cccgtcttgc tgccctgtta  29280
ccggagggat ggtcacggga catgacgaca ttcctgtcac tcagtcagga ggtgctgtta  29340
tccctgctca gtttctgcac cgcatgcagc cttaacggtg tccagacccg tgagtgtggt  29400
cacacgtcac gcagtccgct ggattcgctg gaaagcgcca tcggctttca catgcgcgac  29460
tggtggcagc cgacaaaagc aaacttcttc ggacacctga aaaagccgca gattatcgca  29520
gccctgaatg aggcaggact gtccggtgcc gcacgggacg cggagaagat gaagaaaggt  29580
gatgcggctg aacatgcaga gcaccatatg aaagacaacc gctgggtgcc tggctggatg  29640
tgtgcaccac atccacagac agatgccact gaacgcaccg ataacctggc tgatgccgcc  29700
tgatgaacaa ccacaccgcc ccgccggaga cggggcggca gcaagggaga taccgtgatg  29760
aaaactgaac tgaccctgaa tgccctgcag tccatgaacg cacaggaata tgaagatatc  29820
cgtgctgcgg gaagcgatat gcgccgtaat ctcactcacg aggtgatgcg tgaagtggac  29880
gcaccggcta actggatgat gaatggcgag tatggcagtg agttcggggg ctttttcccc  29940
gtccaggtcc gtttcacgcc agcccacgaa cgtttccacc tggcattatg ttcgccggga  30000
gacgtctctc agctctggat gctggttctg gtgaattgtg gtggacagcc tttcgccgtc  30060
gttcaggtgc aacatatctt cacgcctgtc gctatcagtc acacgctggc gcttgccgcg  30120
acacttgatg cgcaggggta cagtgttaac gatatcatcc atatcctgat ggcagaagga  30180
ggtcaggcat gagcgcacgt tcacgggcac tgatccccct cagcgcagag caacaggccg  30240
ccatgcaggc tgtggctgtc accgaacaac gtcgtcgtca gggacgcaca ctttcagcat  30300
ggccttatgc cagcgctttc tttcgctgcc tgaatggcag tcgccggatt tcgctgaccg  30360
atctccgctt ttttgctcct gcgctgacga aggaggaatt tcatggcaac cgtctcctgt  30420
ggctggctgc cgtggataaa ctgattgaaa gttttggtga agtctgtgtt cttcccctgc  30480
catccgatgc ggggcatcgt ctgttcccgt ccgttccttt tcgtgaaggt gagcggcgtc  30540
gtcagaaaac cacgctgaca gagcagaaat acagccgcca gcgggaacgt gaggcagaac  30600
gacgggaact ggaataccag acatgttttg ctcaggcgca gattgacctt gcgtttcata  30660
ctccctccac ggtcggaagc tggttgtccc gctggtctgg tgttgttgag gagcatgatc  30720
tggaaacgat tttctggggg tggtgcgggc gttttccatc actgtcatca tttgaccggt  30780
ttttctggca ggaggaacca ctctggcggc tgatttttga agctggtgag gccggtcgtg  30840
gtgcaccggt acaggtacgt gcacttgagc agtggatgat cccgaacaag ctggagaacg  30900
caatatgatg aaatcagacg aacaatatca ggttcccgtg tggatgcgac ctctgttgcc  30960
gttgctctgc aataccggtg gtaatgatcc ggaggaactg ctgaatgata cagaaaccac  31020
cgccagtgcg aatattgtcc gttatgtact gatagttgca gtgcggtcgc agattgatct  31080
gctgcagcta ctgtacagga aaggactgtt gcgcacagag ataccaggtg gcttttcacc  31140
```

```
ggaagaagcg caggaactcc tggataatct ggtgcgcagc catatcagca aggcgctgtc  31200
gggtgagcga atggcagccc gtgacagaaa tgccgatctg acctggattc gccagcaact  31260
ggtcgatgcc gcctggtttg tccgtgccac actggaagcg catgggatgg gcgtcggaaa  31320
tgagagtccc tctgctccgc cggagacaat gccggacata cagacacggg aactggttat  31380
gttgatcaag cgactggcat catcgctgaa agcggtgaaa cccgacagta gcgtggtgcg  31440
tgaagcgcag gactggctgt gcgacagaaa acttgtggat atcacagata ttctccggtg  31500
aaccagacat gtatatttta cgcagggaca cgccgatcat gatcgtttca tatcaggggt  31560
ggtctggagg tcatgcggcg tgtcctctgc actcgccgga ataaggaagt cgccggcggc  31620
tccgctttta cccggccatg cggggcatgg ccttgtgggt tttcagctct gtggcctcag  31680
cgtcgtgtgc gggctgtgcc gtgcctccat cttagccggg ctggcaggga tgcaagggta  31740
cgcttcgccg ctgcggtcac ccggtccctc cttcccgtct gccgtgattt tccggtcgtt  31800
cacccgctca gatttcgcgg tctcaccctc caactcccgc cagccgtgtg cgtcaggctg  31860
cggcttccct tgcgccctgt gcatccccgc cttatcgccc ggcttttatg gaggcacggc  31920
accgcccggt gccgcagaac atgtgactat ggaggattcg ggaatgtctg ttgttgcacc  31980
tgctgtatac gttggaacct ggcacaaata caactgtgga agcatcgccg gacgctggtt  32040
tgacctgacc acgtttgatg atgagcgcga ctttttcgcc gcctgccgtg ctcttcacca  32100
ggatgaagcc gatcctgaac tgatgtttca ggattatgag ggattcccgg ggaatatggc  32160
ctctgaatgc catatcaact gggcctgggt tgaaggcttc cgccaggcac gggatgaagg  32220
ctgcgaagag gcttatcgtc tatgggtgga ggataccggt gagacggatt ttgacacctt  32280
ccgcgatgcc tggtggggcg aggctgacag tgaggaggct tttgcggttg agttcgccag  32340
tgataccggc ctgctggctg acgtgccgga gacggtggcg ctctattttg actatgaggc  32400
gtatgcgcgg gatttattcc tggactcctt cacctttatt gacggtcatg tgttccgtcg  32460
gtgatttact cccccgctcc ggcgggggta tggcctgcca ggccgccgga aaaccctggc  32520
aggcttacgc ctgcctgaaa tgcaggaggg ccgcgcctgc ggcgctgccc ttcctgcccg  32580
tcatggtgtg aggcattttt ctgttatgtc gtttctgttg ttctgatttc cggaggcggg  32640
gacaccttcg gctcccggct gcctggcggc atccggtcgt caggcccgac tccgacaggc  32700
agctgctggc gcacccgcca gtctccgccg aacccgctgg cgcggtttcg ggctgccgct  32760
acggtccgat gtctgaaaaa ccaggcttgc agcgaccgtt ccggtcgcgc cgcccctgtc  32820
gcgccggaaa cggcgctccc tgcacacctg acggtgtgta aggccactgc gcctgatggc  32880
gcagtcaacc cttccgccgc cacccctgcg gcctgtttcc cgctgtggac tttccggggg  32940
ctggagtaac cacatcccgt ttcagcagtc caggggaaga tataccgtcc acaaaatttt  33000
tagccataaa cccggcaaaa aattttgcgt ccgcccccgg acagctgccc cgtgacgtgg  33060
tgacggacgc cccatcggaa aggtccactg cggggagaaa ccccgaagaa gtggacggca  33120
gaaggggctt tcgcccctcc ggggagcaac cggtcggccc ggcgacctga ttcagcagaa  33180
ggagacgttt tcatgactgt cagcagcacg atttccgttt tttgccgcga cggggtgttc  33240
cgtaccgttt actgccacct gcacggtgag ccgacctgga acggtcgcat cctgcatacc  33300
cactatgcca ccggtcagca ggccgaagcc ctggttgaac acggtgatat ccgttgcctc  33360
ggtccccgtt gcgacaaacc cgccgggcat acgcttcaga acccggtgga cggtgtgacg  33420
gcttattacg gacgtgacag tggtttccgg atggacagtg aggcgcgtga gtaccgttct  33480
ttcagggagg ctattgccac tgaaagcact gaagaggtgc gcttccatta tgtgttcatc  33540
```

```
gacggctact ggaaggtgat gtaccgcacg ccggaaggct ggaagatgaa agcgctcgcg  33600
ctggcactgc gtcgctgtcc gaaatgaaaa aaaggcaggg cgataaaccc tgcctctctc  33660
cgccggcgct tccccgccag gaagtccggc atctcaatca ctatctatgg agattatgcc  33720
atgagaccat caattatctt cgcaaccgcc gagtatgtaa agcgtctgcg tgaagagtgc  33780
ctgcgggaga ataaacccct gcaccgccat acccgcttca gacgtcagga gctggcacag  33840
gatgagatta acccggacgt cctggcgatg agcggccata tcgccagacg ctgcagtgag  33900
cagaagcggg tgcgtatccc cgctatgaaa gtcagcgaat ggggccacct gctccgcgcg  33960
cttgaaattg agcgggtctg ccactgatta acccttgccg tctgcctgtg caggcggcag  34020
gatacgttca gacatctcac caggaggaac cgtgagtaag aagaaaacca ccacgacgcc  34080
cacgccgcat gatgccgcgt tccggtcgtt cctggcgaat cccgacgtcg ccagagattt  34140
tctggaactg catcttccgg cggagtaccg gcagttgtgc gacctgtcca cgctgaagct  34200
ggaacccgcc acctttgttg agccggacct gcatcagtac gccagcgata tcctctggag  34260
tgtgaaaacc accgggggtg aagatggcta tgtttatacg ctcatcgagc accagagcac  34320
cgaaaatctg tacatgcctt tccgcatgtt acgttacagt gtggcggcga tgcagagaca  34380
tctggagcag cacaaaacgt tgccactggt cattccggtg ctgttctatc acggtgagcg  34440
cagcccgtac ccgtacagca tgaactggct ggactgtttt gagaatccgg cgcttgcggc  34500
taaaatatac acaaagccgt ttccgctggt tgatatcact gtcgttgatg acaatgaaat  34560
catgaaccat cgccggatgg ccgcactgac gctgctgatg aagcatatcc gccatcgtga  34620
catgatggag ctgctggaca aactcccgca ggtcatggtg gaaatttcag acgagcaggt  34680
gcgtgttctg attcattaca tcgttaacgc aggggactct gtatcaccgg aatttatgcg  34740
ggcgctggct gagcgtctgc cgcagcatga ggataaactg atgactatcg cagaacgtct  34800
tgagcaaaaa ggtcgccagg aaggcaggat ggaaggacgc atggaaggac gcatggaagg  34860
agcgcttgaa aaagccctgg ctattgcgtg ccagcttcag aaaatgggga tgacgccgga  34920
gcagattaag caggctaccg gactttccga tgacgaactg aagaaaatct ctcactgagt  34980
aaacatcaca gcccggcaaa atgccgggct tttttgtcag caggagcaga gcaaacagca  35040
tgacgattgc agaacgtctt attcaaaaag gcgcacttga agtggcgcgg gaaatagcct  35100
gccggctgcg ggatatgggc tggacgccgg aacggattca ggaggcaacc ggactttccg  35160
gtgaagaact gaaaaagctg tttcctgatg agcagtagcc tggcattcag ccaggctgtg  35220
aatcacgctc acacatcctc tgccgtttcc cccagttcat tttccagtcg cctgatgata  35280
tctgccttac gcatcccctg catgtgaggc agcaggtcac ggactgaaag tgcctgggtg  35340
gtcctccaga cggtgacgtc cacctgttcc gcattttccc aggcgtgcca tgttctctgc  35400
gtcacgccaa attctctggc cgctttttcg cgtgaccaga gcatgctttt tcgccagatt  35460
cgcagttccc agccggtcat aaaacacctt tgaaaaagtg aaaaaacttc actttatttt  35520
atcatcacaa ttgccaaatc agcgcgataa ataagtgtaa aaaagtgaag aaatttcact  35580
ttttttgctt gtaaatgtcg tgcggttttc tctgttttca cctgtgcggg agtggtgtgc  35640
cagtgaccac cacatgccat tgttgtgccg tcgtttttct tcagtcgcgc cgtatgcggc  35700
gctccctgca caccttacgg tgtgtaaggc cactgcgcct gatggcgcag ctgtctctgc  35760
ctgtctgccg ccgcactgcg gcctgttctc cgcagacgga ctttccgggg gtacatacat  35820
gaccacatcc cgtttcagtc gtccagggga gagatgtacc agccacaaaa ctttttgccg  35880
```

```
caggcgtcaa aaacttttgc gtctgccccc ggacaactgc cccgtgacgt ggtgagcgtc  35940
ccccgtcgga aaggtccact gcggggaaat tcccgaagac ccggacggca gaaggagctt  36000
cgctcctccg ggaaatgacc tggctgaccc ggcagtcgtg acgatgagga gacaatgtga  36060
tgaatcagac tttacccact gctgacctga atactgccgg tacgacagat gttattccgt  36120
ctgtggctat cgaccgcatc atcgcgcagc gtaacgaagg tattgcactg ttcatgcagg  36180
cgatggaatg cctggcgaca gcgcgcaaga ttctgctcga tgcgtcaggt gatatttttc  36240
tttacgggtt tgaagactgc gtgactgatt ccgttcgtcg catagataaa ccggaagaag  36300
cgaaaaggaa tatcacccgt cttgccgacc ggaaaatctg ggaccgcctg atgacagata  36360
cgggcatgta caccttcatg agttcatgcc agcgtgatga gtggaacagc cagctgatga  36420
gcgacacctg tcctgaaatc accctggaca atgtactggc aacattccgc catctgaatg  36480
cctgcaagat gcagacattt gaacagggac tgattgatgt ctaccggaaa ttgtcatggg  36540
attacagaac caataatccc tgccgtctgg gtaagaaaat cattattgaa aacctgctgt  36600
accgctggag taacgggcgt gtgacgctgg actgcagcgg acgggaggca ctggatgacc  36660
tggtacgtcc gttttatctg ctggaggggc gcaacgttcc tgacttcagg aacagtatcg  36720
gggcgcagta tggtgaattt ctcgggaacg gcgacaatgt cggtaagctg ttagaagggg  36780
aatattttac ggtgcgtggc taccagaaag ggaccgtaca cattgtcttt aagcgttctg  36840
accttgttga aaaactgaat gatattattg cacggcatta tccaggtgca ttgccgccac  36900
gagtctgatt aaacagaaaa gccctggtat ttatgccggg gcttttttt ctgtaatcat  36960
cataatctca gaacacgatg tgacattgtc acatcaatta ttgttcatat cgatgccatc  37020
tttcctgcct gaatctgtct ttttaggtgc tgttttagag gaagaacggc gggatggttt  37080
tttcgattct gcttcccgaa taatgtcacg aagtgccttc tctcctactt catacccctgc  37140
atttttgagc gtgtcacgaa catctgccag tgtataaccc tttgtcctta ccaggacaat  37200
aatgtcatca cgaatggcat caagaaaatc acgcaatgtt ttccgttgag cggtgagatc  37260
tggcaattcc gataaagcag cttttgccag ctggatgtca tcatctgagt aaaattttt  37320
agaagccatt ggcactttct ctccgtttca tgttgaagtc tgattttatc atcaaaaact  37380
gactcctggc agggctgcgc cctgcctctg ccgtctgcat aagactatga tgcacaaaaa  37440
taacaggcta taatggcctg aaaaacggga caggatgtgc aattgtaata ccgtcacacg  37500
cgacgctatt acaattgcca tctggtcagg gcttcgcccc gacaccccgt aaggagcctg  37560
aagtgagtga tagtgtggta agaaaaaaaa gtgaggtacg gcaaaagaca gttgtcagga  37620
cactcagatt ctctcctgtt gaggatgaaa ccatcaggaa aaaagctgaa gattccggac  37680
ttactgtatc tgcttacatc cgaaatgcag cactgaataa gcgaattaac tcccggacag  37740
atgatgcttt tctgaaggag ttaatgagac tgggaaggat gcagaagcat ctgtttgttc  37800
agggaaaaag aaccggtgac aaggaatacg cagaagtgct tgttgccata accgaactta  37860
caaatacatt gcgtaaacag ttaatggaag gttgaggatt ctccggtgaa tgcagtcatt  37920
ccgaaaaaga gaagggacgg aaagtcttcg ttcgaagacc tggtatccta cgtctctgtc  37980
cgggatgaca tgaccgatga ggaactggat ttatctcctt cttcgcaggc tgaacaacca  38040
taccgaagcc gcttcagtcg ccttgttgat tatgcgacac gtattcgaaa tgagttattt  38100
gtggcgctgg ttgatgtcat gaaggacggc tgcgaatggg tcaactttta tggtgtcacc  38160
tgctttcaca actgtacttc tcttgaaact gccgctgcag atatggagta cattgcccgg  38220
caggcacact atgcaaaaga tgacactgat cctgtttttc actacatcct ttcctggcag  38280
```

```
tcacatgaaa gcccgcgtcc ggaacagatt tatgacagtg tacgtcatac gctaaaatca  38340
ctcggccttg ccgaccatca gtatgtctct gccgtgcata ccgatacaga taatctgcac  38400
gtccatgtgg ctgttaaccg ggtacatcct gaaacgggtt atctgaatcg gttatcctgg  38460
agtcaggaaa aactcagtcg tgcctgccgt gagcttgaac tgaagcatgg ttttgctccg  38520
gataacggtt gctgggtcca tgcaccgggt aatcgtatcg ttcgcaaaac tgccgttgaa  38580
cgtgatcgcc agaacgcatg gacacgtgga aaaaaacaaa cttttcgcga gtatgttgcg  38640
cagacagcgg tcgctggttt acgcagtgaa cctgtacatg actggttatc cctgcatcgt  38700
cgtcttgcgg aagatggtct gtacctgtct cagatggacg gaaaatttct ggtgatggat  38760
ggctgggatc gcaacaggga aggtgtacag cttgattcgt ttggtccctc ctggtgtgca  38820
gaaaaactca tgaaaaaaat gggtgactac acgccagtac caaaagacat tttcagccag  38880
gtggaagcac caggacgcta taacccggac tttattgcag ctgatgttcg cccgggaaaa  38940
atcgctgaaa cagaaagtct gcagcagtat gcctgtcgtc atcttggaga acgtctgccg  39000
gaaatggcac gggaaggtcg gctggaaaac tgccaggcta ttcaccgcac actggctgaa  39060
gtgggattat ggatgcgtgt tcagcatggt cacctggtta tctgtgatgg ttatgatcat  39120
acccagactc ccgttcgtgc tgacagcgta tggtcactgc tgacgctcga caatgtgaat  39180
caactcgatg gtggctggca gcctgtacca acagatattt tccgccaggt tacgccaaca  39240
gaacgcttca gtggtcgtcg tatggagagc tgtcctgcga ccgataaaga atggcaccgt  39300
atgcgtacag gcacggggcc gcagggggct atcaaacgcg aactgttttc tgacaaagaa  39360
agtctgtggg gatacagcat cagccattgt agccctcaga ttgaagaaat gatcacacag  39420
ggtgagttta cctggcagcg ttgtcatgag ctgtttgcac aacagggact gatgctacag  39480
aaacaacatc acgggcttgt tgtcgttgat gcctttaatc atgagcaaac gccggtgaaa  39540
gccagcagca ttcatcctga tctgacactg aggcgtgcgg agccacaggc cggacctttt  39600
gtgagtgccc cagcagattt gtttgacagg gtgcaacctg aaagtcgcta taacccggag  39660
ctggctgtca gtgacaggta cggggtcagc agtaaacgtg acccaatgct gcgccggcag  39720
cgacgtgaag ccagggctga ggcccgtgct gacctgcgtg cccgctatct agcatggcgt  39780
gaacaatggc gtaaaccaga tctgcgttat ggggaacgtt gtcgggaaat tcatcaggca  39840
tgccgtctgc ggaagtcaca cattcgtgcg cagtacaatg atccggcatt acgtaagctg  39900
cattatcaca ttgcagaagt tcagcgaatg caggcattga tcaggctgaa agaagacatc  39960
agggatgagc gacagaaact tattgctgac gggaagtggt atccaccttc ttaccgtcag  40020
tgggtcgaaa ttcaggctgc tcagggagac agggctgctg tatcgcagtt gagaggctgg  40080
gattatcgcg atcgccgtaa agacaagtca cgcacaacga cgacagaccg ctgtgtcgtg  40140
ctttgtgaac cgggcggaac gccggtatac ggtaataccg gtgatcttga ggctcgtctg  40200
cagaagaacg ggagtgttcg tttccgtgac cgtcggacgg gagagttggt ctgtacggat  40260
tatggtgaca gggttgtttt ccgtaatcac catgaccgca atgcgctggc agataaactg  40320
tatttgattg cacctgtatt gtttgagcgt gatcccagaa tgggctttga accagaagga  40380
aacgatggac agtttaatca ggtctttgct gaaatggtgg catggcacaa tgtgacggga  40440
ttctctgaac atggaaatta cgttattact cgaccggacg tagatcagca cagggaagtg  40500
agtgagcggg gctatcgcaa ttacatggat agtaacactt acagagatgg aactcagcca  40560
gttcaggata gtgagaatcg ctgggaacct ccaacaccgg tgtaaagaat gttataaacg  40620
```

-continued

```
ggagattgtt atggcttatg tcgatgattt taaagaagca atcatcagga ctcggcggtt  40680
acaacttgca caacccgttg atttatgtga gacgcatact cgcataatga acgataaacg  40740
aatccgccat ttgggaggaa ttatacgtcc tgtactggat ctgaattctg ggtatgaaca  40800
actggttgcg cgatgtatgc ctgttcatct tcaagccaga cctttggttg aagaatggct  40860
gggatgtcct gtttatttta cgttgggatg gattgatgat gggaccccaa aaggtatgtt  40920
caggtttgat gaggacttta ttactgatac attgaaaaat ggttatacag gagatactgt  40980
caatcttcat gcatggctaa ctttacccag tatggaaatt atagatatca cattatcaac  41040
aacaatttct atgttgcagg ggcataagaa tcagttaggc ggtgttatta tcaagagagc  41100
tgatgatatt aaaggattct catataagcc aatgcttatt ggtgatgaat tcctgtcaaa  41160
atctggtata ttgcataagt ttacatatct agaattgaac tagtgatttt taaataaact  41220
ggtttttga cgttcttatc tctgttcaga aatcacctcc tgttggggtg attatttata  41280
ttatgagttc tggcaggtcg atatgttatt tccgaaaagt gaccatctct cagatacaga  41340
actctgtctg cggatgctat tgtttctggt cgatgagcta ttaacagaac aggaattccg  41400
agttggcgta atgtctggct tatttctatt tcactttcca catcaagatg actggttgct  41460
tcgtccagta ataatagacc gggtttttta tacagtgctc ttgccagtag aatacgttgc  41520
ttctgaccac ctgaaagtcc ccctccggtt tctccaagta atgtttgata gcccattggc  41580
attgccataa tatcactgtc tataagtgcc agacttgcgc atttacgcat gtgttcatga  41640
tctctaattt cgctaaaaaa cattatatta tcagctatag aacctttgaa aagatagtca  41700
tcttgcaata cagtgccaat tcgttgacga acctgaaaat aatcagaatg tgtatgtggt  41760
atgccaaatg cattaattct tccttcactt ggtgtatgaa ttccaagaat aagctttacc  41820
aatgttgatt tgccacatcc tgatttacct gttattgcta atatttctcc aggaaagagc  41880
attagtgacg cgttatccaa tatgggttta tctgcgccct tatggctaaa tgttattttt  41940
tcgataagta atggtggatg ggtattatca tatttatgtt ctctgtactg gcttgcagat  42000
attgtttcat tatggtttgc ccaatggtgc tgattctggt gaccttcctg tggtgttagc  42060
acaatatcgg caagtctctc gttataaaca tcaagcatgc gccaggaaaa aaagttatca  42120
gtcagattgc ttatactgga tgaaaaacgc atctgatagg ataagtaagc aaccaacata  42180
cccacggtaa atgtcccatc cagcacttct actgctccct gccacaaaat aatggctgaa  42240
actacacttt ccgtcagtgt atgcgtcagt tcatagctca tttgtaaacg attctggcgt  42300
agctgtgtgt ttctgcgggt aacgttgagg ttcagccagg ccgcttctct gtgaatagtt  42360
acaccgttga ttctcagact ctgaatgccg ttaagggttt cgagaaaatg ccccgactcc  42420
ttagttcctg catcccagac atcttcaaca gattgccgta aagccggata ccacaatgct  42480
ctcagtgcgc catatataat agctgcaatt actgcgatta atgtcattcc tgggctatac  42540
aacagcatca tgcaaagagc agtcacaata agtagcatat ccagaatgcc ttcaagaacc  42600
tgcgttgtca gcgcctgctg gattatatct actgcttcaa aacgggcatt aatacttcct  42660
ttacttcggg catcgaacca tgcaagaggg agtcttacaa gatgatggaa aactctggca  42720
gtccattgca tgttaaaatt gacggataaa ctgatcgttg cccattgtcg tgctagggag  42780
agtaataatt gtatgagtga taacaacagt agtgccacta taatgacata caatagactt  42840
ctgtctgctg cgaccagaac ttcatcaatt accagttgat taagaagtgg accacctaaa  42900
gccagaatct caagggccag agcaaaaata ataatttttg tcattgatgc taaaagcccc  42960
ggggttttcc ctgtcagttg acgcaggtgg atttttttc tctcgttccg gggggtgaaa  43020
```

```
tcactggctg gagttaattc cagtgccact cctgtaaaat gcttacctgc gtccaacaga  43080
cttattgtaa tttttcctct gtccggatca tggatgtata accggtttcc ccgaacttta  43140
tggagaacga cgaaatggtt catatcccag tgcagaatag atggaagatt aagacacctc  43200
agatcttcgg gttccagacg aactgcacgt gatgataaat ggatggacgc tgcacattcg  43260
atcaaccttt gtagcgtcat tccctgaata cctatattga aacgttcccg taatgtcgat  43320
aaatctgttt tcagtccatg ccagcaggca atcatagcca gacacgccag accgcattca  43380
gctgattcgg tttgacggat aacgggtagt tgtttcctta ctttccagtt tattgattcc  43440
attacagatt tcctttcatg ctccataggg gctctgtcag ccattcccat aaatgacgag  43500
tatcaaggtt gacgtctcct tccagagtca tgcctggtct tagcggttct ttttttccgt  43560
atgcaaatat aaatgtattt tcaggttcaa caataacgcg ataatgccct tcgttttctt  43620
tccatgtgac gggtgaaact ggtaataagt cggaaggagc cagagtcgta tgactgattt  43680
tacgaattgt gccgtactgg ataccaaatt tctgataagg gaaggccgaa aacttcagag  43740
atacccgttg acctggtcgg ataaaaccgg ctttctggct ggtagcataa agctcaattt  43800
gtaaatgagc attatcggga atgagagtca tgaccggttc agatgctttc acagactgcc  43860
cctgtttgat cagtacagca gcaatagtcc cggatactgg agccctcagt gtaaattttt  43920
cttgtccggc gagttcatcc tgttgttgtt ttagcacctg caattgtctg tcgagttctg  43980
ctttacggct tttcccctga acaataagat gatttagttc atctttggct gtgtccattg  44040
cagtatgtaa ctggagaagc ccctgacgct gatcttcaac gttttgttga gcggcagaaa  44100
catcaatttg tttctgttgg aattcgatat ctgacacata atgcgtacca gccaattttt  44160
tatagcgttc catgacggat atagccagtt ctgcctgacg ttcagcaagc tgaagtcttt  44220
gttctgcact tcttatttgc ggctcaagtg atatcatcct ttgccgtatg gcttcctgtt  44280
gttgactatt atctcgcgac tcaaaggatt gctgggaggc caacataata tactgagtct  44340
tcagggaaat actcatcgtt gctaatgtgc cagttccgtt accgttataa tgttctccac  44400
ttatatgata gagttgtgtc cctgcagtta cgtgttctcc ttcggataca gtcagttgtg  44460
ttacatatcc tgcatattga ggaattattt ttaccagtcc tgatgagggc atgacgatac  44520
ctgtaagatg cgctttcctt gtatagctac cgtaatatat gaatacagtc agacttaaca  44580
taatgaataa tgtaactgtt gcacatacgg ataggctaaa tgatgttggt aaaataatgt  44640
caccatattc agtgtcatta tgatgttcta ttgcttcact tctgaatata ttcattattt  44700
ttaatacaat aagtaacctt tccgtcaaca agagggtttg gttgaataat attgatattt  44760
gatatacatc tgacctgtgt gatgttaaag ttttatacta taatatattt aacaatataa  44820
caaagccgtt tattcccgca tgtaacagca ttggatagaa aatcccctta ctgcaaatcc  44880
ttatattcaa caataacatt gacataataa acagaataat ttgatcagcc acattataat  44940
actgcggatg catcaggcag aaaaataaag atgtacacac gcagggggta aataattctt  45000
ttttataagt cgtacataga agaccgaata gacatgttcg gtaaacaatt tcttcataat  45060
acggaactgt caggaccagt ataaatattt caatccaatt aagtgaagtt gattcactat  45120
tgttcaaatt gtctctataa gcaaaaataa gcagttgcat gagagcaatc acagcaaatg  45180
atattactaa tagctttaat gttttcgcat ttgtctttat ggtgatttta caacctggta  45240
ttcttcttaa gtaaaaaata taaaatgaag ttgacattaa aatttcagta ataaagacaa  45300
aggaaaatgc cagatccaaa ccaatatatt gtatggtgaa tgccggtgtg aatatcacaa  45360
```

```
ctgttgatat aacaacaagt agaagaaacg ctatcgcatt atctttacta tatttatata  45420
tgttatcatt cataatgcta tttcgcggag attgttctta ttttttctat gatatagtcc  45480
atgaatcttg ccgtggaaaa aagagtgatc agcatgacta caatctttga aaactcggaa  45540
ggtagtgaaa accagtataa atcaataaca gaggagccac tcaatagtgc aaatcccagt  45600
aacaaaccac atataaagga aagtaattta ataaacatag tagcgccctc cattatatct  45660
atttatcggt tacatgttcc gccaacatta ttacctgaac aactactgga acttcctctg  45720
ttaccacttc catttccact accatgatct gagagacatt gaccaacaac ggctccacca  45780
atggtacctc ttgccattcc tatgggacct cctttgatcg caccaccaat cattccacta  45840
aatacagcgt tagcgcattt tacagtgctt ggatcactat aaatatgagt tggtgcgttt  45900
cgacccagtg agttacgagc ccactggaa cggtcattac gggggccacc ttcaaagttg  45960
ctgtttgcgt ttcctccgct gacaagcgtt atctcatcta aagttaattc tcttatattt  46020
gccatatcat atttccccta tcggttgttt gttattttgt gcgttcaaga tagccaataa  46080
caaaaatgta atgaaagtga aattgtgtga ttaaatgtaa atatgtgaaa aaatttgtat  46140
gttttcgagg ttgtgtaatt acaaaaatat catcgtgtga agatataaaa ccgttccagg  46200
gctggcacgg cctctgttca gtacatctcg ttccagtccg aacggttgtt tttttctgat  46260
gaaaccagtt tacaggacgc cctgtcgggt ggttattgtc ctgtgggagc gttaacaggt  46320
ttatattggc tttttctgct ctcactgata tctgattttc ctcttttgtt tcaggtggtt  46380
ctggtctgtt cagcgtgata tagcgaattc gtcgctcttc cagtgtggtc gttttaagcg  46440
tattcaccgc tgtttcccac aaggcacttt cacgtgcgtt gatatccgtg tcgtactctt  46500
ccagcattgc catagctgcc tgacgtcctg caatgcgttg ctggaatgta tccacgatcg  46560
tgtgcggctc tgtgcgaatt tttcgtcttt ttctggaggg ttttgcagtc aggacgccaa  46620
tgatggcact gacattttcc ggtgacggga ttcgacgttg agctgtacgg ggaacaagac  46680
ggcggagacg gtccaggcgt ggcgcatcca cgctgatata cctgtttata acaacgggat  46740
cgctgctgca gcttttctca tcgtcaggga tgaagaatga tgctgatggt acggtttctc  46800
cccggaatat agaaaagaac tcgccaggat gaagttcaat caactcctga acatctatct  46860
tactttccat caggatgctg atttgtgggc tgtcaatcca tgattcacca aatatgccgt  46920
cctgacgctg caggttgttc atcctcgccc tggcttcttc accggcggcg cttttcagcg  46980
ttctggccgt actgccctcg ctgacaatcc tgccggcaaa ttttgtcccc gtgttctgca  47040
tcagtgttgc agtattcgtg gctgttgtct gtccttctat acgttcctgg tcctgtgcca  47100
tcaaaatcag agcaaaatcc agtgaacgca cctgagtggc ttccacagca atacggtccg  47160
tatagtatgc ccccacttca tcaaggaaac acagataagg gaaacgcccc ttatattttt  47220
tgacttccag tgcatcggaa tcagttcctt cgaggcggta gcccaaatca cgggcgagaa  47280
tcatactttt ctgggtgata aacattcgtc ccagagcaga cgttgtatgc gctgatgtat  47340
ccagagcggg gatcattacc atcagaatcc tgtcgctgtg aatgctgtca cggatatcga  47400
tatcaccgga atcttcagca aaaatatccc cgaatgcttc cgtgaatgtg ctgaaagttt  47460
cagaaaactg cccggagaga taagcatgtt gttttctggg ttcttccgtc caggctgatg  47520
gtgtcctgac cagcgacagg tcgaaaccgg gaacgtcctg aaggtagtta cgtaatggtg  47580
cgatagcttc ttccggccac tgatcatcga ggccatgaca gtaaagtttg gccattcctt  47640
cgagagtcat atgttcacgg agcatctgca gcgacattgt tttgccttcg cgcacacacc  47700
agaatttagt accaaatacc agtgccttgt tcatggcaat ggcccgggac tgccactcgc  47760
```

-continued

```
ccccctggac gttctggggc agcattgact gcattgtctc cgctgtgaat gcctcagtgc  47820
tgtaacagaa gggattccag gtatttgact gaggacgcgt tttttcacca ctcagaatga  47880
tttcactgcg ggattttcct ccgttcatga agttgatgac ttccacatcg tcttcacgac  47940
caaagcgtct ggccagatac cagatcgttc ttgccgtatc attctgtgcc ttgccatcga  48000
caagggtgaa tcctcttgcc cagcaaagcg ggttaatcgc ccaggcaaag atggtttccg  48060
ttttaccccc accggtggtg gcgaaaaaca ttatatggcg ggtcagatcg tccatactca  48120
gccacaactc ccgacctata tccctgacgc gttgataacc aacataaaat atgccgctgg  48180
ccggtgactc caggatgacc tcatactgaa acagagttgg ccagaagctg aaaaggcttc  48240
ttttaatcat tctgtcctgt gacgggtcag cacattccag cgtcatgggc atacgaagag  48300
ggcagcgcca tcgctgcaga ctaaatacca gcatcgttat cagtgtgaac aacagacatg  48360
ccggtaatgc aagtggccag ataaaactgg ccacaagact tgccaccagg caaaagccat  48420
agatattgag actctggagt gcattccaga caggatttcc ccaggctgta cggtgtaaaa  48480
gctcggggtt aacgcgatgt tcactcatgg ccagactcgc tgtcggttgt tttcaggaat  48540
aaattaagcg tgccagtttc ctgcagaatt ccagtaggca gatgccagcc cgtgtcggac  48600
agtacccatg ggtaccggc aaatccgaac ttacggaagg cgacattgtt aacatcaatc  48660
gcagctctgg ccgctttcag gcatgtttca tctgcaggcg ttgtttcttc tgatggcgtc  48720
atcattccgt tatctgcgga atacagtcgg tgccagccgg cagcacgttt ctgagcatct  48780
ttttcacaca gcagtggtgc cacacggtcg gtggattcct ctccaccaat aactgaaacc  48840
gggtagataa cgacattgaa ggcgctggcc aggcgtttta aggctggctc cagaagtctg  48900
cagttaggac aggcaggatc gagaaatgcg taaagggttc gttcatgacc ggatgacagg  48960
ttgacggtaa acattccccg atcggcgttc cgcttcagaa cagcagccag attatgtcgg  49020
gcagctgcgg cttccggatt tttgcttgtg agtgttttat ccggtacctg gacgtctttt  49080
ttcggggtaa ccgggagttg aatgccttca tttaatggca cggtgtgatt caggtgaggg  49140
gggagcagtc gtggctcacc tgccgtctgt actgcttcag gcgttgtatc atcccagaat  49200
acacgatcaa catagcggaa cagagagacg gcaatcgttg ccattacgaa cagtacaacg  49260
ctggcgatta ttgcacggaa caaaggcgtt ctgctgaagc ggcgttccat caggtattca  49320
aggcgcagac aggaatcaat agctgtaagt atctggtcag cgttatgctc ctgcttgtca  49380
atcaggacgg tttctctgtt acgagtgccc atggcgtcaa aggctatatg aatcagttga  49440
ttgtttcgtg ttaccagccc tgacagggca tcccgtggaa ggacggcaat aatttctgtc  49500
ctgctatccg gccagattgc ctgcacggaa atatgttttg caatgcgtgt tgcaaagtac  49560
tcgattgtca ttttcagttc tccggataat cagaattcgt tgtctgtagc aggtgtgcgg  49620
ggcaggatgt cgtcggtgag ggaccagttg gtcagaatgc ggcgtttccg gtcgcgatct  49680
ggttgtggtt catcccagat aagaccgaga ctgagcatat cccgccgtaa gccttccacc  49740
gcttcatcaa cacaggggtc agggcaggga aggccaaaac gcatggcttc ggcctctgca  49800
cgtgcaacgg ccaccacgcc agcgccttca ataaatcctt tcgtggtatt ggcgcggtgt  49860
aatgcataaa acagcgttct gtccacgcct ttcagccaaa tccagttggg tggcgtaagc  49920
cgcaggtcat gtgcatacag ccagaccagc ccactgcgga cgtagcgatg ttgcttcagc  49980
cattgctgtg ctccatcgct tttaatcact cttttgaatg cagatttggc cagtgaataa  50040
actggggtac agaatttccc actgtcccgt ttgcttttaa ttctgcatga gaggttcagt  50100
```

```
gtatccatga gctttaatgc tgccttacga tcatccagga aatactgaag gccaaatatg  50160
gcaaagagcg ctttttcatg tggtgccatg tctttccagg acgttaaagg tttacccaac  50220
tgggccatga aacatcgtct tgcagctgca acatcgagct gcatattggt gatgagagta  50280
tgctgctcga caaatgcttc cggggtgaga gcaacccgcc gttcaggtcg tttgccacca  50340
tgaaagagtt tttccggatc accatctgcc agtacagggg cgatagcagg ggacaacgaa  50400
gcaaagatgt gtggcagtcg ggtaatatct actggtctgc gggtgaaacg actttgtccc  50460
ggatgttgat accactccca caaacaccag agtgtcacag gtaagaggta catccacaga  50520
atacctatgg tctgctccat gacgttaacc cactggctat agcttatgtt ggcggcgttg  50580
ttaccggtca tggcaagcag gttgtatcgt ggtgctgcat agttatgaaa tggtccccag  50640
tcaaccagtc cccataaggt atgaagaatc aggcagctgg cgtaaaccac ttccggcaag  50700
aataaccata taacgaatag cagcaggata agaaggacac caacagcgcc ccatatctgc  50760
ataggatctt ctgcgacagg ctgtcgattg taagacatga caaagtctcc atttctggaa  50820
tttaaatcaa acggaaaggt taaaaattta tttgcaggcg ataagagcta accagaggaa  50880
ttagccgtgc gataaaagga ttgttgcaga tacgaaagtc gttagaatag ctgcgggcgc  50940
ttgaggctgt atgccgaaag cgttttgtgg acggtataca gcagaaagcc cctggagatt  51000
tttttatcaa tcaaccaagg gctctactgt aatgcttcga caacattata gtagcccgat  51060
aaccgccgta aggcaatgga ggggctatga tgccacagcg aacattttta atgatgttga  51120
tcgtcgtctg tgtgacgatt ctgtgttttg tctggatggt gagggattcg ctttgcggat  51180
tccggctcca gcagggaaac acagtgcttg tggcaacgtt agcctacgaa gttaaacgtt  51240
aacgggcaac acggcggcag gtttctgcc gccgctttgt tgcgaaggct gacctcattg  51300
cgccctttct tcttcaatga agcgtatccg gtattgtttc atttcccctg aagccgatta  51360
gctccagccg aatgcctttg ccatcggggg ccacgttctg catttcgcag ataccacgtc  51420
gggtcatgag tgtgaaggct gtcattgcca gcatggctaa cgcattttcc tcgcttccgc  51480
tgcgtttctc gagagcatcg gcaatttctt ctatgctccc cacctgaaag caagagtcga  51540
attctttact ccacttttct gacatcggat tttctctctg tatttatggg tagttatcga  51600
actgaatgtg ccagtttttt caggagacga caaagttgag atggctgatt caggttcaga  51660
gcatgagttt ccccggtgtg acgggcatgg cggggcggat tttgcagata caaaagacgt  51720
aaaaaaaccg actggtgagg ccggcttttt tactgttacg ctacaaagtt gatgactctg  51780
accagaaaag agctgtctat aactgacgct aaaaatgata atttgttcta cctgattaat  51840
gcaacatgcc ataagtttac gggaaaggct gaccacctga tattgttgca aaatacgaaa  51900
gtcgtcaaaa tcgcggtggg gagcttgagg ctgtaagctg aaagttgaaa gcgtttgtga  51960
aagccccagg agattgttct atcaatcaac caagggctct actgtaatgc ctagacaaca  52020
ttatagtagc ccgctgacgt cctccacgcc agagggagct tgctacgtac agcttgtcgt  52080
tactcagaag taataaatgt aaaaaaaccg actgatgagg tcggttttct tactgttccg  52140
ttacaaagtt ggtggccctg actggaggaa atctcttttc aactaacgtt cttataatag  52200
tgttctgttc atttgataac aaccaccctt ataatccgca ggttaacact gtcgcgcgac  52260
acttctgtcg tgatgaaggt aaccagaaca tgagtcttcc cggtgtaaca ggcatggtgg  52320
ggcggatttg cagaaacaac agatgtaaaa aaaccgactg gtgaggtcgg ctttttttact  52380
gttccgctac agagttggtt gctctggacg ggaaaagaca gtctgtatct aacataatca  52440
attctatgct ttgtcccaca ctatgtcaaa aatcctgcta atcaagtagt atacaaaatg  52500
```

```
ttagctctac tgattgtctg agttcgacaa ctgacggatt tgttaagtcc tggtcgggat  52560
aacaggtggt gctgcttccg gtgctctggt cggagtgagg cagtctgtat ctaacaatag  52620
aggcaaccgt agtgacaggc agcccatgag taagctgcgg tgtttcgctc ccttatcaag  52680
ggaaaacgga tgattaatct gttaatcatc gttctcaggg cagtggttgc cgttgcaaac  52740
gcgctgattg ctgttctgga actgatccgg gaacttgtcg accgataagc ccggaaacgt  52800
aactaagggc agggagttac cgcttcctgc cctttaacaa aaagagatct cacgttaaaa  52860
atttgtaccc ttccttaact tccagtgcct gctcctttga gtcaaacatc agtcttgttt  52920
ttccgggaac accccatgaa atgtattcga catctatcca ccattttcca tattcttcat  52980
atggcccgga tattactttt ttgacaaagg cgtctaccag attcattgtt ttttcctttt  53040
tattttgaaa ataattaatg ccagagcaca gcgaaaataa tgaatgcact ggctgtgata  53100
attgcgattt tctcccatat gatatttttc tcatgggagt ttctgcggag attatttctt  53160
cgcattggaa tatattggat atgtttattc atgaataaga gcaggtgtgg gatttcctgc  53220
tctttttgtt ggcgttattt tacatgcttc cagacagaag ccggtacttt gtcgtacaat  53280
ttgttcattg tcagttccgc aaggcgatga tcaactgcag agttgaatgc ttctatttta  53340
tccgagacca aagtgccttg gtttttagca ataattttct caagtgtctt taagctggaa  53400
cagcgacgta attgatataa ccattcctgt tttgtttttg ccataaatag gtccttgggt  53460
ttatttaata cggcataagc tatgtgttgt tgcaaacaaa agccggctca tctgaaccgg  53520
cagttatgga ggctgcttat cttaaaatac ttcagctaca ggcatacctg caatctgctc  53580
ccactcctta cgcttttcct gaatcaggcg aggaaagtcg acagggtaat cgtatcctct  53640
ttctgccatt gcgtgtaatg tgtttgcaat agaacgagca gagttaacac caatagacaa  53700
ttctaacatt ggcatattga catactttgt gtgtatttcc atacagtttt ctcttactac  53760
tgtccgtgtg aaattatcaa tatcaatgcc aatgacatct aatgttttat tggggtaaag  53820
ccgaatatat aacgcagtac ctttttttgat atcaattccg aaatataatg atgatattga  53880
tttgtgttcg taagatgggt ctggatcgaa tgcatcatga cattcggtct ttatctgttc  53940
taagatatta tttatgattg ctcttttctt tcttccttct ttatatccgg agtatagtag  54000
taatccagtt gggattactg ctagtcccca actggtaggt gtattccaaa tgattagtaa  54060
tgggacggcg aaaataatgt agaaaagtgc gaatgcgatc acgcatattt ctttttttaga  54120
atgggtgccg ccacggtttg catatgctcc aatcattata tatgacctcc ataaacactt  54180
tttgatattt taatctctcc aagtgtatat ggcaagtcat atattaagtt attatccctt  54240
tattccatcc ttattgttgt cgttattcat tcttttaatt tgctcctctc ttatattagg  54300
tgcgtgtctt atgtttctat tgctgccagc aaaaatctct tttattgaac cagccatatt  54360
gccaagcgtg tttacaccat cacgtcctcc taggaaatta attacatggt ctgggaggta  54420
tgcttgtaag gcaaatgctg cggctacaat ggttgtgcaa cttctagcat aaagaagtaa  54480
gaaacctgcg aggctaaata tacctgtaaa tgaacttatt tgtacattgg tcagtgcagc  54540
accgaataaa aagtttaata tagtacctat tgctataatg gctacagagg caaaaaagaa  54600
tccgaaaacc atgataggag gtcttatcat gctgtctatt aaatatatat aaccgtaggc  54660
agcacgactc cctctgtcct gtgaggtgcc tagatgagtt gccccccaca gaggtccagc  54720
tgtacatccg attaatacac taatgaccca gttaccaatc ccagtcatcc agaaaataaa  54780
cggaataaat ggtaaataaa tagataaaga gaatcctgca caaaacagca gtagtaacag  54840
```

```
aaagtatacg gggggcgcta aggcctcaag taaggcattt agtgttgaaa tagcacttgt  54900
cgtcaaatct atgaatttac caaatataga actcccagtt cctgaagtaa taactctagc  54960
agatgtataa gtaatccaaa taccctctgc agcgaccata gttttatcac caatattttt  55020
catttttatc agtggattaa cttgattgct acttgtaccc gaatcagtcc actcggtggc  55080
aatattgttc gtaagccatt gcccaaactt ctctgtgggc ttgattaaag catcttgtgg  55140
cgtgcttgtt tttgaaagta gttgttcgtc tgctgaagtt atagtaccta aaggtggggt  55200
ataagttgaa ttctgcaatt gggtcttgta tgcccccata acagcactaa ataaatcagt  55260
gtcgccaact tccccaagtg atgacattga agttacagct ggagctctgt cagccagctc  55320
tgccagacgc tggttagcag tggcaaaggt ctgataccac gcgccaagcg ttacccatcc  55380
ataggttgtg agataagact tgagagcttc tttcctggat tgttctccgt tatcaatagg  55440
tagcgatttt tgtacagcac gctcatactc gtcggctgct ctctgaatcc gtgtctcgat  55500
atccggcaat gttccgttgc cagaatttct tttttccaga aatgttgtca caaactcact  55560
ggcagcgttg tccatgtcgc taatcatatt atccatggct gcacgttgtg ctgagataac  55620
accgctgtat tcgtttttac tgaagggatt aaagaatttt ccaatcgtcg attgatctgt  55680
tgttccgttt ccttctactg acaggctggc tgaaccacag ataccgctgc cattggatac  55740
cgtgacagtg taattaccac tggcggtttt agctgattct gtcatcagtg aagtcgagga  55800
tttggccgtc tgattaaaat catttagtcc tgcgttaacc gcatacttac acagttccat  55860
ttcaaaaatg ccacgcgctg ctgttcgtgt ggatgcctga actggctgta cagtcattga  55920
ataaccattt gcgatattat cagcggcaag ttgcaccatc acattggcgg acccaacccc  55980
cattatcgat gcgccccata acataatgag ctgagcgata ctccagccat ttccggttgg  56040
aacgatcatc agaaaacctg caacgacact cagtgtgccg acgatatcgc gtccggtgct  56100
gaatacctgt ccctgatgcc ccgaacgcac aacatgacgg ataccaatga acataaacca  56160
gacaacggca agtacggcga tgatactgtt gaacgccccg aacatgcttc cgatcagagt  56220
gggggcgctg gttgacagtg gattggtgac tacatcaccg aatatcgtga ccagcgcctg  56280
gcgggacaga tcgtcaggat tggtggcagc agacacaata tcctgatagg tcactgaagc  56340
cattgccggc agtgaggata tagcaaggcc tgcacagagt gcgcgaagta aaattttcac  56400
agtaactccg gaatagaatt gcgtatgggc aaaggccaca caggatttaa ttaaggggga  56460
tggcgacatg ccagtggtac tggcatctgg acgtgatcag tattgtttac tggttacggc  56520
aattaatgtg gcattgcgcc agccattgcg gtcgttcaga aaatcacgga aagtcccctg  56580
ctcgggttcg ctgacttttc gttcatgcaa ctgccagagg cggtatgtaa caatcagtgc  56640
tctggaagca caaagagcga cgcctgacag tatcaacaca agagtgctga tggcgcgtac  56700
cagagtcgta agaggtaatg aagaggcggc aaagagcata ccactgagaa acaaagcgat  56760
ggccagcaga ctccagcaac agaatcgcca tactgttctg cgccggcgga aacgacgatc  56820
cagatcgtct actgacatat ggctggcctg cagagcttct tcccacgtga ggtggagttg  56880
cgccttttta ttatttacct gacgaaatct gtccagcctg cgtttttgtt gttccagcat  56940
atgctgtaca gaattcgtta tcaggcgagt ctccatcaga ggaacaaaaa tgttaataat  57000
cccccgggtg gctatgcggg ttatggatgg tgattttttg acgtttttcg tctggtctga  57060
attttccggt aacttattca ttttttcagt cctgttctga cgtcagcttt caacgtgcgt  57120
ttgcctgatt gattgttttc tcaaggctac cgagttgttt ttcataatac tggcgggcag  57180
tcagagccag ttgctggcca gagataacat taccctggcg gatctgttct ttcagatcgt  57240
```

```
tcagctgcca gttcatttgc gcagtgattc ttaccagttc acggagcagg ttatccccct  57300
gcatttcctg taaatccacc aggtatgctg tgttggcgta gcgccggcca gcctcaaaag  57360
cttcaaactc acgggtactc atatatcccc gtgcttttgc ttctggtgaa gccacctggt  57420
cgaagtaagc ggccgctgag tctgactgca gtgtttcagc cagtgcttta cgtgtgcttt  57480
cattaggcgt gctgtcagca atcaacgtca gttggggatt cgacgcagaa tcaatgatgc  57540
cgttgtattc gttctggagt ccgacgtagg ttcgcccact ctgggtattc acttctcctt  57600
tacccagagc acgaccggca gaggggcggg aagtgttttt catgtaagca gtcgctgcat  57660
ctatttgctt ctgatcccat gtcagtgccg caggtgtgtc cgctgtacct gcgccgtggt  57720
aaatcgagcg tacctgactg tctccacctg gtatttcgcc cacagaagga caaacggcgg  57780
ttcctccaaa acgtgcatat tctgcttctg tacagtaact ggcgtgtatg gccgcgccat  57840
cataagcttc ccgcacggga gagtttgctg cgctggccag acggtcgcgg atgctacggt  57900
tgctcacacc gccaccttta ctgagttttg aggctgcgga tgctgaggca cttttgcttt  57960
ctgttgcaat ccctgatgcg gattcactgc agatggagtc tggcacggtg aagcttttcc  58020
gtgcctcctc gaggcgctga gtttcattac tgaaaatcat ctgctgacgt gtcgcctgtc  58080
cgttctgggc aatgacactt gccagctttt cagagttctg attgatagcg gtacccgtgg  58140
ctgtctgggt actcagtatg tcactcagca cacctttgat ggcctccatt ctggggacga  58200
cctgctgttc aacgggacgg ctggcgacga cggtgactga ataagcatga gcctggtatg  58260
ccgttccatt caggatagct ataagggctg cgagtaatgt ttttctttgc attttattgt  58320
ctcctgctcg ggtggagca caaggtcagg aaggctgtcg tattttctgt cttcaggtag  58380
tggggccagt gggaaacact gatatcgcct ggtgatataa cctttcctgt tccggttatc  58440
gatgatgctg aaagaacgac gtctgacgcg ccgtaaggtg gaagggtcag tatccataac  58500
aggccagtca ccggcactca gtgccggcgt tccgggaacg gatggccata accaggtatc  58560
atcggacatc agcgaagtca gcggtgaagg gagtatccac tggatgacat gctgaacgtc  58620
gaatggtgct tcatccggga cagaaacctg ccatattgcc gttgttatca gctcatctgt  58680
gctggacggc aacaacagcc gcatgcctgt aacctttccc tgtgttctgg catccgaggc  58740
gtatatcact ctgggattgg gggccggatg taacctgaag acacgtgacg gcagagtgaa  58800
tgagaaactg tcacctttta cctcaagttt tttaagaaat acctgccctc tggcaggtct  58860
ccggcagcgt ggggtgatat gaattgtaca catcagagat tgtatccctg ttttcggatg  58920
agctccgagg ccagttcttc aataacattg tcactgttat gttggcccgc ccggtgctca  58980
attaatgacg ttgcagaacc tctggggaag ttttcggcca gaatcttacg tgcccgaact  59040
gaacctaact tatttgtcag tgttttacgc agggcactgt cttttggcga tgagttcagc  59100
gcccatagct ccagtggacc gacggtaaat ttgagtattc tcgcaagcgt gccacttttt  59160
accctgaata ctcccagaac aggaacacca ctaccatctg gtgccgggcc ttccggcatt  59220
ttcaggaagc gtttcagcat aaattcagga acgttgaagt tatccctcag tacggggata  59280
tcttcgggtt tgtagcgcag taaccagaga gtatttgctg acttaagaac gctttccggg  59340
tagtccctca gatactgcgt actcagaacc gtgcggatag caaacttgcg ttgctcacgc  59400
tcctgggtat ccagattttc ccagatgaag tcaatgcccc gggcgttatg cagttcatca  59460
taaacttttg tcttaacctc ctgatcaagt tggttaatac gtttaagagc gatttcatgg  59520
tattcccgtg gaagctgctt taacacttca tccctgtatt gtggcagggt gaagtcacca  59580
```

```
ccggcgatct gacctgcaag caggtacatg atgccggttt taagcctgcc tgcaggcgtt  59640
ttgtcaccgg caacattatt cagatcgaca gcgatgaccc gggtttccgg gttgatcata  59700
aaccgggtat acccggatat catggggtag tcgttatgtc cctgctcgag cgcgcggcgg  59760
atgtagtcca gcagaagttc gtttgaacca tcacgctgaa cagtaccgaa aacatccctg  59820
agactggtat ggcccagcat cgaggacact tcgggaagct ggggcattgc ctgataatgt  59880
gcccgctgag ccgccatgat atacccggca ttgtggagca tatcccggac ttcgaaccag  59940
gttgatctgg cccaccaggt tgcatcatgt ttttcataca gtcccgagtc ctgcagtgct  60000
gaatccacca gttcttccgt tgaggcgcga taaagtcgcg gattattttc accgtactct  60060
ttaaaagcca gctcgataag ctggttgata atttgtcggg tgtctccggg gttacagggt  60120
tgaccggtac cggtatcgac acagagagca cacagcaccg atgacatgaa attcttttcc  60180
ggcgtaatag gctttttagc gccgtacatc acgtcaaaaa ggttacgggt gtattccgga  60240
tcattgctca gaataatacc gacagcttcg tcttttcttt ccggaggaag actgtcgcga  60300
ataagctgaa ccagtccctg agcactgtat cccttatcga tataggcaat gaagggcagg  60360
tttttctgag cagatgatat ctgtatttcc gacaatgtat taatcagaac tgatttaccc  60420
agtcccggat cgcctggtgc gagttctgta tgtttatttt gttgggatga cgccagacca  60480
acctcaattg cggaaccgtc ttctgtatgt aacataagat tccctttacc tcgccagaca  60540
gagcctgccc tgttaagcgg gaaaagcgag atggcatgtg acaacggggg atacagggga  60600
accgggccgg agcctccgga tgccgcgaga atggtattca cccaggcgcg tcggggatcg  60660
ccaaatgttg tcgtggtgcc acatacgccc cagccttcaa tggctgattt cagaatggcc  60720
tggtttcgtg tgcatatttc acgtgttttt ccccacgtgg aggccatgat ggtcattatg  60780
cagacaggtt ctttttcatc cgttgccgcc agggccataa cggattcata cattggacga  60840
acggcagaaa tgaagctgct gtaagtcaga agcgttttct tcagattaag agccttcatc  60900
ccgccgggca tcagatccat tctgatgcgc caggggactg cgcgggggac ggcacggacc  60960
agttcgttaa acgtctgcag attttgcgga ggtaaagtaa tcgataccat tccgtgccag  61020
agtccgcccg cctgaaccag gttgccctgt gtggtcacct gagtgttgaa taactgcaaa  61080
tgcaatgaag gagcatgtag tacggattca tcgtcagtcc agcgatatcc cgctggctgg  61140
gcatcttcag gcaggtgggg ttgccagtta cgcggtgtgc tgtgccgttc tgtctgacga  61200
cgtatttcac gcccgacctc gtgtatatcc agtagccgga gaatcaggcc atcagatgaa  61260
tgtctcagtg cctgttccac attatcaaga aaagcttcgt ggcggatttt cagtgcagat  61320
aaggtccact gccaggggga ctgggcaaag cgtgctttcg gtacccgttc agccagtctt  61380
ctgacaagct catcatgggc ggtgcgatcg ctgttgctga taaggtcggg tccactccag  61440
atcgccagcc agcaacgctc ccggaccagc catggggaca gtgttgtgac tttctcatcg  61500
accacatcct gtaactggat acctgtatta gccagtgagc gcttttgtgg ggcgaccatg  61560
tcttcgattt cttctttccc catgtcagga tcacgctcaa aaacgaagct gattttatga  61620
ccgctgtttt tatatgccgt attcaggctg tcactcatgc tggtgatcag cgattccagt  61680
gaacctgggc cagtctggtc ggatgcttca tccatttccc tgaaagcacc gctgacttca  61740
aagacagaga gatattctcc acgctttgtg gctgcaatat agggcgaatt cagccatggg  61800
cgacgttcac gatcctgtct gtccagacca attacagtac gtaaatcgca atactcaaca  61860
aaactgcttg cgacagagaa acgggatagc gtgttcagac agtcttcgat agtgaagatt  61920
aaacggttta tgttcatagg tgagggaact ccggacttac aggagggagg tttgtgcagt  61980
```

```
ttgatttttt taatgccacc ccgcgctgga gtggcatgaa gaaaaatcaa tcaacgtatt  62040
ctttttgat gaatgaatct ggtgtcagaa tcagggcaat cccgttcatt ttttcacgca  62100
ggggcgaacg accggaaggt ggatagcgac gaaaaacgtc agcgaaatcg gccgggcgga  62160
aactgcggaa tttatcctca accgccagtc tgttttgcat cagtgcagag agcgcttccc  62220
gtccccgccg gacccggaac ttatcattac tgaaaacttc ctgtaatgaa cgacggttaa  62280
gggccacgac cgtggatgga tgaaggtcgg gtagccacac cataacgccc tgtgctgcgg  62340
cataaccatt cagtgaatgc caggcgtggc agaaagcaca taagctgtaa ggcgggccgt  62400
cttcatgaaa cagttcctgc tctttctctg acaacgactc tgtactggtg atttcagctt  62460
tctgtacatg gcggagtgaa agacgtctgg cagacagacg ggcctgctca agcgcccgtt  62520
cagcggcttt tactgccgtg ttgtactttt ccttttcgcc ggttgcgact ggttcaccac  62580
gctttttaa cttatccaga tgttctgtgg ccttattaag acgaactcgt gtgtcactga  62640
ttgtgtcggt aagctgtctg agtggccatg agtcatccag tctgaaacgg tgcctgacgt  62700
tttgccggca gcagatacat cgaccgggcg ttgttaattc cggttccggt aacagtggct  62760
cctgtgtatg aaccacatca atttctggaa agggatacaa ccacaagtct ttaatgctgt  62820
gttgcatgag caggctccgt actggtgtaa cgtttcacgg cttccagaat gatgtttgcg  62880
atttcatcgg aacagcattc tgcaaaaatg aattcctgat cgtcccgact gtcgtgggca  62940
atcacattgc cgttttctgt tcgtcgtaac gttatgtgct ccgggctcca ggcagacata  63000
tgtgcctcct tgtattgccg aacaggaagg gcaccggata aatgccagtg ccctggacaa  63060
gattagccaa tggaaattgt ggaaatcccc agctgtttct ggctgcgact catcatttca  63120
ggtccggcga caagtagcgc cccaatgacg atagatacaa tgcaaccagc cagtcccatc  63180
ccccttgtt tcccaacttt tttcaggcca atcaggcccc cgagaaacag aattacgccg  63240
atgaactgcg caatagtcag tgatgatgac tgtgctgttt tggcaccttg ttcgacattg  63300
cgaaccatat cggcaagatc tccatcggca agaacggctt tgggcagcaa catcatggga  63360
atgagcagca ggaacttagt cagtttgctc cggcatgaca ttacaaacag ttgtgcgtgg  63420
ataaatgcgg cgtacagacg ggccgctacg acacgaatac gtgacatagt ttctccttaa  63480
atggatatat cagtggttta tatgaaggtg aaaaaaatca gaagacgatt ccaatgcttg  63540
ccagcagggc attgaggaca cgatcgataa agaccagcag gacgccggca ataaatttga  63600
cgtttccctt actgacggat tcactggcac tcagtgcggt atgtccatcg agtccggcct  63660
tgcgccagat ggatatcccg ttcattacaa atccaacacc ggccagcttg gccagcgaca  63720
gaactgcatt tgctgcgcca gcagcagcgc caaacgtctg aggttgtaca tatgcaatcg  63780
ggccaaatga gtcagccctg aatcccattt gtacgcctcc ggcgttaatc attgccggga  63840
gtgatacgag catgcagctg gttaacatcc ccgcaataaa ttttccggga gacattttta  63900
ccggaccggc tgaacgggcg cgggcaaaca gggtaatcat gctgatcacc ccgatgaatt  63960
ctccccaggt aaacaggaaa tccattccgg cactgaaaat actgctggca aagttctcaa  64020
tggcggtcag ggcatccatg ttcatcagcg taacgtccct gcactggtga tgatggtccg  64080
ggtcgtcgga tcaatccgct ggatcaccac attgcccaga gtctgacctt ctctgacagc  64140
ccaggtacta ccctgccagc gaatccaggc catgccagtt tccatcgaca tgattttcat  64200
tccgttaagt acagacgacg tttttttctt tgctggatgc ggtgtggaag aggattcggt  64260
gacgcttttc tgtgtcatca ttccgttcag gtggctccgg atatcatcca gctgacggcg  64320
```

```
cgtttcctgt gcgtattctt catccttttt tatagcttcg cccagcttgt taatgctgtc  64380
gtgaagcata ttcagtgttg cctgaatttt ttcatcgcgg ttatccagct ctgtttttac  64440
atcccgggca agctggctca tatcttctcc tgtccggaca gtcatggtct cagtggactg  64500
aacggaaggt gatgattctt gtgtggtttg ccaggtctgt acgccagcat ccgcatcatt  64560
aaacggaggc atgcctgttt ccgatggtgc tctcaggaac agataccata tggctgcgag  64620
caatacgact gcacatagcc cccatgttgc tacagatatc cccagacgg aacgtttcca  64680
gaaaggggcg ggtttctctt cgggttcacc gaagctgccg gtttcatcta tttctgtttc  64740
aggtttcatt atggtgtctc cggttgttca tcataccgac gttgcatcac agcttttctt  64800
tgctccatgg ctgtctgcat tcgtgcctgc gagcgttgtg ccgtctgtga tgtacgatta  64860
actgaagggg aaatgccact ggaaagggaa gatgacctgg cgtcgtttgt cattaccggg  64920
tcaacaaaca gaattgatac gacttcatgc tgatacactt ctacctgttt atagggctca  64980
ctttctgcct ggcgggttaa tatctgactt cctctttccg ccataccacc ggcaataacg  65040
cccgcaacag cttcaccact gggcattccc acgcgtccgg taaccgtgcc atagttaccc  65100
tgaataacct gcgtgttggc atctttataa agtgtgccaa tactgcccac acctcctaac  65160
actgacggca gaatgatatg tttaaaccag cgtgtattca cattgctggc cacggatgac  65220
atcaggttgt cttcccgttg agcatatgca ttgaccttaa ggtccatgcc gttccagctc  65280
atccggtcga aatggatctc cacgccgtta cccaccagtt tgactcccgg actgaacagc  65340
gttgcccctg cccaggggcc agcgggaatg gttgcgataa ccttggatga cgggttatca  65400
gaatccactg cagtatcaat atatgccggt atacgggtca gagcaggtat cagttgtatc  65460
ccttttctg ctacaggcgt ggacaggctg gcattctgta atgcgaattg ctgcgtacca  65520
ttctgccctg ttgtttctgc cggagattta ttccacatag tcgttgctat ggttggtgta  65580
ctaccggcag gatgctgatc ttttattctt acaatcagct tttgcagccg ctccatacgt  65640
ttttcactgg ctgctcgatc ctcctgtggt gtgccggaag cctggcgatg agcatagttt  65700
tccggttttg ctgcaggctg ttgttgcttt tccggagtgt ccggaatatc aagcccctgt  65760
ggaagactgg caatgaacgt ctgattattg cgggctgcag ctgcggcccc tcgttcatta  65820
tccgctctta acagttcacg atagtgaggc gtttcggtaa cgctgcgcgt tccgccgctt  65880
gctgcactgt taatgttcac ggctgactgc atatcgctgt tactccctga tagtttggaa  65940
aacgcgatat agccgccgcc aaataagatg atgctgccca gtccaagcag ggcagccagt  66000
ttctttccgg atttaccggc atcctgttca gcactcatga ttactccagt tctggtgtca  66060
cgtgaacgga ctggccattc acagagaaag tcagtagtgg ggtgacggga agtttccaga  66120
gatgagttcc gtcggcagag gacaaggtct gttcaaattc atcgcgcaac atcgcccggg  66180
aacgaaccag aaggtcatcg ccgtgttgcc agatcgttgt atccgggaca ttacctgtga  66240
atttcagcct cttaactgaa gggtcccggg gaggaatacc atccagaaat gcctgtaatg  66300
ttgcatcatg cagggcgatc ttatccgtcg ggatggagac aactgggctg gttggtccct  66360
gccgtggtat tcgcagatcc agacgactgt ccatttcctg actggatgac ggcgtatctg  66420
tttcgccact ggttacgttc aggatgaccg gtaccgacag acctttcagg tagacagaaa  66480
tatttccgga tgcccatggc cgcaatggtg tgattgtcac catgttctcg ttgtactgca  66540
catcaaagag ttttggtgcc gcgttataag gaggatcgga ttgtggccat ggtgaaccgt  66600
tgatatcggt aaatgtcacc acgctcaggt tgttcatggc tgtgcgaaca agaggaaggc  66660
tggcaccggg ggacagatta actgtcagag agctgatacg ggtacaaca ctggtgatgg  66720
```

```
gcgcattgat ggcccgctcg ttatccgcca tgagactgcg tagtgagcga atctcatcgg  66780
cggagagctc agaatcaagc cttgccgcat cctgtaccag cgggctggcc tgcccggggg  66840
caggcagctc accttttacc agtgttgccg gaacacctcc ggtgttttgg gaggcgttct  66900
gaacgtgatc gctggcagaa tttgtcgttt gtggtgtgcg tgcgttctgc catcctgcgt  66960
tatctgcaga cgtggcggcg ctgcacacca ggagcagtgt gctcagtaaa taacgtgatt  67020
gcatattact tatctcagga gttcggtccg gcgttacggg agatcatctg ccggatttcc  67080
ataccggatg gtttcagtct ggggtcaaca cgctggatgg tgatttcgaa aacaaaagac  67140
tgttctggct tgctggttgt ctggccgacc agacgcatac ggacaggata ctggaatgtc  67200
cagaaccata cgccgtcgga catttgtccc tgtcgtacca gaacgccagc acctgtcgtg  67260
gcggtcagat tcatcttctc tttcttgatc gtctccagaa tgttagatgc ctgtaatgca  67320
ttcacatatc cgacaaaacc ttcgtcagaa aaacgcggag acagggagga gatctgtgaa  67380
cgatagtgca caaaatccag gttgaatgcg gtcgccagtg cctggctgcc aaaggccatt  67440
gcatcattct gactccatgc tggctgactt gttggtgcca gcctgaccag acgaccattg  67500
tctgtagcga aatattcgcg ctccacattc gttgagtgcc agtactgaat ggcgttacca  67560
gtaatactga taagaagaca tgtgcccgta cataaaagcg cttttatcag cgcagggaca  67620
ttatttgccc gctgttctga ctgcttcata gccctgattg tgctcttcag tatttccggg  67680
tcaggtgccg gatgtgatgg cgaggatggc tcggtatttt cggtcatagg ttgtagtcct  67740
tccagggatc aatattcccc ggcagctttt cattcacctt gtccacgacc gcgtcgcaga  67800
cctggttttc cagctgcgac agaatgtcgt caaggctggg gaactggggg aggtttatgc  67860
tgattttttt gattcgtgac agacaggact gcagggatga ggaaacatcg ttttcacgtt  67920
gtgaccatgc atccgcagct gcacgtgctc gctcatatcc tgtattacta ccggcctgtg  67980
ccgcgctacc cgcacgacag gttgcagcac ttgccgtgga tgaaatcagg ataaggccga  68040
gcacggcaac cagagactta tgcatgttca tatggcttcc ttaccggctc atcggccggg  68100
gctgtgggag agatcctgat gcagagtttt ttcctgcctg tcctccggct tttggctgtt  68160
ggaccactgc tgccatgact gctcgaagcc caggttccgg tacaacgcat caggttgttt  68220
ttccggcgtg tagacagcag caaaaagcgg ttcttcccgg gttttcagat gaaactgcat  68280
aagctccggt gcagggcgat tcgtgctgtc agcatcgtgg tttaccgctt caccataacc  68340
tgcaaagcgt aaacctttgt cggtcagcgc attgataacc agctgactgt tgtcggctga  68400
tggggtggcc agtgccggat acaatgtgcc gttcagccgg accacaccct gcagatgttc  68460
atcggcactc tggacaagta gcaggttgag ttcacgcgta tccttatcca ctgatcccag  68520
aacaggtgtc agcttgtcag ggctgcgct ggttatttct gttacctgat ttgcgttctg  68580
tggcgcggag accggatgtc ggtcttcacc gataaacaga tgtgagccga cgttttctgg  68640
catacgtaac gctttcatct cttcgggcca cccctggctg atttgcgcag ccactttcat  68700
aaaggtttcg accggaatcg cctgaatacg ctgaccttta tccggattat catgtgatac  68760
cgagatcccg ttggtaactg actccatgga ccacttattc cggaaacgtg ctttttgctc  68820
tcctgggagg atgaattgtt cgcggttctg aagtgtcagt gtcaccacgt cacctttctg  68880
atggtttttg accagacttt ccagttgttc cccccagtag agtttgctgc cactgcggtt  68940
tttaagctca acaaagaaac tctctccttt gccgggtgca tattcagcac gaccaaaatt  69000
gtgcagtacg gcagtcacgc tctctcccgg gcgaagtttt cctggtggtt cttcaccttg  69060
```

```
tgccgcatct gccgttttgc caggttcagc cggtgatgat gcagggacgg tgctgacggt  69120
tgatgcttca ggggctactg ggacgccgg ggattgtgtg gcttcttttt cctgaacagg  69180
gtctgggact gctggttgtt caggggtatt ccggttaagt tccggtgttg gcttatgggt  69240
gacaacagta tctttaccga cagccatttc cttgcgtaat ttttcgagcg ccgctcgctg  69300
atccgggaat ttcatgcgca ctttgatgtt gtgctcgatg atcaactgca tcgctttttg  69360
cttaaaggca tcactgcccg tcagctcaat gacaccacca taaaaatcag tggccacagc  69420
aagtgcagcc agaacactgc gatcgtcatt gctggcaccg ttgaccattt ccagccggtt  69480
tacccggtca atgaaggcag gtttgccatc cagtttgtac aggacggttc tgtctgctcg  69540
ttcttcacct tccagcgatt taatgatttc gtccagattg agcgatatcg gtgcatcagg  69600
gcgttccggg gcgtagacaa tactgtcagg tgccggtgtg gtcgtcgtgg tttccggtga  69660
gggtgtggga tcactgttct catgcgcctg tgaatccgtt tttttacgcg taaaaaagcc  69720
acgcgctttg tcgagaaacg atgaagtatt atcagaagat gatgtgctct gaacaggttg  69780
ctgtggagtg gggcatccc ggacagccgg ttctactgta tctgttgtgg cctgaagttc  69840
tgactcatca gcctgaacgt ggcctgtgtc cggttgcgac ggcatatcac tgttttcctg  69900
cagatgctca ggattttcat tgttcatcag ctcctgatat gcgctgtagt tttcgtattc  69960
ttcggggcca tctgactcag gaaggaacgg ctctggctga aggggaatgt cttcagttac  70020
atggttgacc gcctcttccc ggggagtatc cggggatatt ccggtgcttt gtttgtcatc  70080
aggctccgtc atcacggtca tttcctcttt gactgcatca ggggaaggtg atggctcggc  70140
tgattcattc atggtttcag atgagggact gtcttcaggg gatgcggtgg tggcagcagg  70200
ggccggtatt tcaggtgaag tgccggattc ctgttgtgac tcgttttttt ccggttgtga  70260
cagttcggct tcaaattcac gccagtcttt atctgtggcc accgagacaa ctttttccgg  70320
aggttccgcc ggatgagcgg gttcatcagg ggcagacgcc gttgtacttt ccggggacgc  70380
cggtgattct gcaggggagt cctgaactac agagctttcc gtttgcgcct gaacgttatc  70440
agcgtgccgc tcatctttgc cgttattttc agtggcgtga ctggtaaatg actgtgtttc  70500
atcagcaatg ttactgctgg aagcagctgg ttgttcctgc tgcgtggcgg acggcagaga  70560
aggtccctgg tcatggctgt gccctgtatc gggtgatgtt tcaggatatt ctgtcggagt  70620
catggttttt tcctcagtgt ggaccggtgt aaaaacgagg ttgcctatca ccagtgcctc  70680
gcgcatttcc ggggtgttac tgttgggggt ggaaaccccg atgtgttcta actgggcgtt  70740
gatgacatgc tgaaaagcgg cccgtccccg gcttgcgtcc aggtcattga aatcggtcag  70800
cccctgcgct tttcggcat cggtgaacgc aggaaagatg accgatcctc ctgtcagttc  70860
tgcggctttt gttgcactga cgatacctt gttaacccgg attgcatgat cgttgtcggc  70920
acagaagata aaggggcttt gcgtccactt ttgccgggca ttttcggcaa cggcaatcat  70980
gttgcctcca tccaccgtca tcagtaccgg aaggcccgtg gcttcgtgca gggaggccgc  71040
agtggcatag ccctcggcaa acagtaccgg ctgaccgttg cgcggtgtgc ccagcgcaaa  71100
ccagttaccg gttttctccg aatctatcag gatgcgggca tctttccccc cggtgaccgg  71160
aatacgctgg taagagcgta tcgcgccgtt acggttactg aagggaataa ccagttcatt  71220
tttgttgttt acccgcaccc ccggtgcagc ctgaatgcct ttccgggtca ggtattcatg  71280
tgctgtggcc tgcggccatt tgttgatata gcggcgggca tacgcggcct gtcggttgta  71340
ctgtgctttc agttcccgct ccgcgtcctc cctgcgttgc attgaatgcg ctttcaggtg  71400
gagtcttgcg cggggatctg tctgttctcc gccggagaag gtccaggtga tcggcgaatt  71460
```

```
atccgcgctg cgataatccc tgtaccagcc ggcaggtctg ccgtccagga agccgcgata  71520
tgcgccactt ttttgtcctt ttttgtcatc ggcggtcggg acacggtgga ttttcccgtc  71580
catgaccggc agttctttca gaaccagtcc ggcattctcc agaacctggg caaactcggt  71640
gaccggatca ctgccgttca tggagacgtc ctgtggccgg ggcagccagc ggtccagcct  71700
ggacaggtcc gcccccgggc gggcgaacca gagtttgtgc tccttgtccc agatgacggg  71760
cgtgtgcccg ttcatcgggg gatgtgcttt tttgagatct tctatttcat ctgcaggcac  71820
ggcaagccag gtgcggtagc gggatacaga cggcatgagt gcttctcctg aaaaaagacg  71880
gaaaaaaacc accgccggaa gccgagggtg gctgggggga tagaaaatcg gggagagaaat  71940
gtttgtcagg gtctccagtc tgtaccctta ttccagcgat cctgccagtg ttcaagatat  72000
tgtgcggcta catccggcat attcttgagc acaacgacat tctctgaatt cttgcgtgca  72060
gcagcacgag agaagttata ggagccagtt tcaaccgtgt ttccgtcaac aatgatgact  72120
ttgtcgtgat ggatggggaa ggcatctaca gtccggagag gaatgtccag caggttgata  72180
ttgtcaacga cggatgaaaa gtgatccact tatatctcca ccaacggccc aatattgatc  72240
caccgtttta ctcaggatta gcttctgcta taaccccggc ctttcgtttc tgtctgagtc  72300
gatagctttc tcctttgatt tgaacgacat gtgagtggtg taagatacgg tccagcatcg  72360
ctgaggtcag tgctgcatca ccggcgaacg tttgatccca ctgcccgaac ggcagattgg  72420
atgtcaggat cattgcgctc ttttcgtaac gtttagcgat gacctggaag aacagctttg  72480
cttcttcctg actgaacggc agatagccta tttcatcaat gatgagcagg cggggggcca  72540
ttactccacg ctgaagcgtc gttttataac ggccctgacg ttgtgccgta gataactgaa  72600
gtaacagatc tgctgctgtt gtgaagcgaa ctttgatacc tgcacggact gcttcatagc  72660
ccatcgctat tgccagatgg gttttcccca cacctgatgg ccccagtaat acgatatttt  72720
cattacgttc tatgaagctg agtgagcgta acgactggag ttgcttctgc ggtgctccgg  72780
tggcgaatgt gaagtcatac tcttcgaacg ttttcaccgc cgggaaggct gccattcggg  72840
tatacatcgc ctgtttacgt tgatgacgtg ccagtttttc ttcatgaagc agatgctcca  72900
ggaagtccat ataactccat tcctggtcta ctgcctgttg tgacagcgca ggcgctgcgc  72960
ttataaggct ttccagttgc aactgcccgg cgagcaccat cagtcgttga tgttgcagtt  73020
ccatcatcac gccactcctc tgcagaatga gtcgtagatg gagagtggat gatgcagggg  73080
gtgtttgtcg aagttcacca gattttcatc aagatgcacg tcatactctt ttttctccgg  73140
aggcagtgcc agcatggact gctgctcttc gagccagcga tcgcagggac gtgcctggat  73200
tgtttcatgc tttcgttggt tagcgacatc gtgcagccag cgcagaccgt ggcggttggc  73260
tgtttcaaca tcgacagtga tccccatcgg gcgcaggcga gtcattagtg ggatgtaaaa  73320
actgttacgg gtgtactgca ccatccgttc caccttacct ttagtctgtg ccctgaaggg  73380
gcgacacagt cggggagaga agcccatctc cttgccgaac tgccacagcg aaggatggaa  73440
ccggtgctga ccggtctgat atgcgtcacg ttgcagaacc acagttttca tattgtcata  73500
caacacttcg cgcggcacac caccaaagaa gcggaacgca ttacgatggc aggtctccag  73560
cgtgtcataa cgcatattgt cagtgaattc gatgtacagc attcggctgt atccgagaac  73620
agcaacgaac acgtgaagcg gtgagcgacc attacgcata gtgccccagt caacctgcat  73680
ctgtcgtccg ggttcagttt cgaaccgaac ggcaggctcc tgctcctgag gaaccgagag  73740
agaacgaatg aatgccctga gaatggtcat tccgccacga tatccctggt ctctgatctc  73800
```

```
gcgagcgatt accgttgccg ggattttgta aggatgagca tcggcgatgc gttgacgaat  73860
ataatcccgg tattcatcca ggagtgaagc aacagcaggt cgcggcgtat attttggcgg  73920
ctcagatttt gcctgcaaat aacgtttaac ggtattgcgg gagatcccca gttctctggc  73980
aatcgcccgg ctactcattc cctgcttgtg caggatttta atttccataa ctgtctcaaa  74040
agtgaccata agctctcctg aatcaggaga gcagattacc ccctggatct gatttcaggc  74100
gttgggtgtg gatcactatt gcaccgttcg tgacagatat atttcatcgc ttcctgactt  74160
gcccggttcg tattcccctt gtcatcaaca acaatacgga cgtccactcc gcgtttttc  74220
gcttttgcca gcgcatgcat tacatccggg tcggtgaagg aatatgccat catcctgatg  74280
gagctttccg cactgttgat tgtgtcaagc accagagcgg atgcgcttcc ttcaggagaa  74340
aagccgacct tcacggatgg cgtgtcgatc attgcaaacg atggtgtcgt gaacagtaac  74400
gggcatgcca gtagcgatac ccggagcaga gtaacgatag tttttttacc tgacataaag  74460
actccagaat ttaatcgagg ccagtccagt ctcgtggtga ttccgtatgg tggcgatacc  74520
accatggacg accggaggcg atggcccctc tcagaatgct gaaaatgcga gtacagatcg  74580
tcctgacagt ccagcctgaa cggtcgagaa taacgaaaaa taaaatgatg ccggtgcaaa  74640
tccagaaggt tgttttggag ggaaagggcc atataaacag ataaatcatg gtgaacggca  74700
gaggtacgcc ctggatgttg actggcggtg ttgcatatcg ccagaaacct tctcttttca  74760
tgaccgtaac tcccctggcg ggataaaaag aatcgcttct cttcggtcaa cttcattccg  74820
gatatacatt tccagaatct ggtcccggat acggcgcttc tcctgccgga ttatggcatc  74880
aatgtgatgc cccactctg catgtggcat tccggaaaga ttgtcgcgaa gctcatcgtt  74940
aatgacgata tattcccgga cggctttacg accaccgtca tttgttctga ccagaacctg  75000
aaccagaatg aactgcaaca gtgacaggac agcccaggcc atcgaatccc tgatgacagg  75060
gggaaacagc ccaagaagac gtgccagcgt ttcaccagga gatttcgtat gcatggtgct  75120
caggcagtaa tgcccggtgt tgcctgcctg taccgctgcg tcggcggttt cgttatccct  75180
gatctcacca acaccgataa tttcgggatt acgtcgtaca gcagaacgca gtccggcagc  75240
aaaactgacc acatcacgcc cgatttctgc ctgatgcggt gggagcagat cgttttcatt  75300
tcccaggata tattccaccg ggtcttcata tgtcacgatt ttggcgtcgg ggaaattgtc  75360
cataatgtaa cggtacagtg ctgaacacag cgttgatttt cctgacccgg tttcaccaca  75420
tacaaatccc agaccgcttt tgcagaccat tgcttcaagc agatctggtt caatgttcat  75480
ggagagaatg tccggtattt ctgtcgggat gacacgcatg gttattgaga ctgctttctc  75540
ctccgcacca gatgtgccct gaatgaggtg agagcgtaac cggatgcgtt ctccgcgttt  75600
aagaccatag cgaccggatg catccccgtt aatctgtatc gtcctgtcaa ccggattgcc  75660
tgccagaacg cggggaatga cttcccgacc gaacagttca tcaatcaggg aggacatgag  75720
tgtggttggt aacgttgcac tggaacaacg cacccgtcgg ccaaagcgac tgacagatac  75780
aggtgaccca ccggtcagat ccacatcact gactttatgt gcggcacacc agacaaagaa  75840
atgccgtagt tcatctgcag tgaaacgctg aaacggaaaa agaccaaact catcaggaat  75900
attcatcggg agcctccttc agtgcctata agcggacgcc agtgagattt ctgaagattg  75960
aattccgcat gatttttaag gcgacgaaca cgatctccag tgaccagttt tttcccgtca  76020
cctgtaacgg tttgcatttg atcagaaaca tccggacggg tgatcatgcc ctgacgccag  76080
agaagtgagt acagcatcat gccccggtaa tcacgggtga gggttttctg gttggcttca  76140
agcgtcaggt cggcgttttg tcttccttcc tgccatccct gccgtaatgc ggtttcccac  76200
```

```
acttttcgtt gcacgctgtc ttctggaacg acgctgcctt ctgtacccgg agtggctgtc  76260
gttgaaagcc cccggagaag ccagtcacgc cagcccggtg gattgctgac aaagcgttca  76320
gggcgaatga tggtccagac ccgggaagag gtccggattt gatctggcgt gatatgagct  76380
acgtcctgtg cttcatcaat aaccggtggt agccagcctt ccgggctaat cagtggccgg  76440
aaatcgtata aggcattaag tgtgctttcc cgggcgttga gtgcctgaat cagctcccat  76500
gaacgctgag ccttgccacc acgaaatcca agcgttttac ctgcgtcggt cagcattttc  76560
cagcgtgttt ctgacagact atccggcttt tcacttcgtg gtttaagcca tgcattaatg  76620
tcaggtggtg gcgtattgac cccacctggc gagatggtag gggaagaaga acaaccagta  76680
agcagtatta ctggcaaaat gagagaggtg agtgctttca ttttttccgg ttctccggct  76740
gcatgaagct gacctgtaac aagcccggat attgatggat tgttgctctc caggctgtct  76800
gggcttcaat aagtctcaac gtattggaaa acgtcatatc ccggacgtga aggttgactg  76860
gtaacggcag gcggacacca ttgtagttaa actgcatccc cctgactctg gccagttcgt  76920
tcagtaattc aattgcatca ccttcccagt caaaggaaag gcgatcgctg ttagctgtca  76980
gaagatgaga ccccgttgaa accggaagtt ggccggaaaa cacacctttg tcccataatg  77040
tgtactgagt gtgccgggta accgccacat cagaggcagc accgtagtta cgcggaacag  77100
gagtatgctg agaagggaag ttgcagccag ccagaaaaag ggcggcaaga caccccgcag  77160
gtataatacg gttcataata attcctgagt agttaaatca gaatgggata taccggtgct  77220
ccggtacaga caggatgatg tttgtttccg gctatacttg cgttaccgga aataaatgcc  77280
agtgtggcca ggtaaatagc ctcatagttt actgaaggtg attattcctg atactggctg  77340
gttgatgtgt cgtcagacat aaaacgaata tgagcgtaat ctttaacgct ccgcgccgaa  77400
tcgatccatg atggatgact cgacgattta tgaatcgaac gtaccggcgc ttgtccctga  77460
aacagttccc ggccctcgtc cggataacct gcaattcaga caggcacatg tgcccgtaca  77520
ctcttgtatc ttactgagta tatcagaatt tatgtaaatt caaatatcct ctatgactct  77580
ttgttgtatt ttccgtcaag tatgagccgg gtaccatcgt aatgcatgat cagggcatca  77640
aggtacgccg gtttgaattt cttgccgagc ctatctctgg ccagaaatga taaacaatga  77700
ttatgtgtca ttattactat gttcctttta tgagattctc ttgcgattga ttcaagcgtc  77760
ttataaagat cattattgca gtctgataaa ctgtccataa cgacgggttc tttaccggag  77820
aagaattttg cagtttgtat ggttcttacc gcattgctgg agtaaatatc atattcactg  77880
aagattgttg cgaacttaat accttcctgc tgtgctttct ctgtaccggt aatagtgatt  77940
ccgcttttat ccgaatagca tggcatatct gaacggtcgc aacgttctcc atggcggaaa  78000
aggaaaataa cggtgttatc agcattaatt tcttttgcct gttccagggt gatatcggga  78060
agcgagcttt ttgcttttgt cactgccgct accaggaaaa cagaaaataa aagaatgaat  78120
gctgtttttg aataagaaga acgtggtttc atcatgttat ttaaactgaa tataaaaata  78180
cccccgggtt tagtgccggg ggcggggact gtaatcagaa agtgaactga agttgtgcca  78240
ttgcaccgta atcgtggtca gttcctacca ggccggaaac atcgatatgt acgacgtcaa  78300
atggagagat accaacgcca gcggtgaagg cgcttccgga gtttgatgcc atgttctgac  78360
gataaccggc acgcaattgc gcccatttcc atgcgttaaa ttcagcacca acacttgcaa  78420
actgacgttt gctgtcagaa gtgaagccac tggcaggagt cagatcaacg tcaagagcag  78480
tggtaaacag gtcattatgc caggatacac cggcggttgc ctgtggacga actttgaagg  78540
```

```
tttctttaaa gccattgacg actttagtat caatactgcg tggaatgatg ttctgggcaa  78600
caagaccgac agtccagttg tcattcaggt ctgtataagc accaatatcg gcgttgaatc  78660
cgtttttcgt gttgtggtac ttgtcaccgt caaaatcgtc tttgtcgtaa tcacgaaccg  78720
ttacgttgta gttaaacagg tccacacgct gatattttgg tgtgacgcca agagaccatt  78780
tttgtccggc cgtttccagt tctttggcaa atgaaattcc gacgtcggta attacagctg  78840
cacgcccgaa tgcgcgtgag gtcagggcat tcttatcgac gtcggtaatt gttccattgg  78900
caactttgtc cagataatcc aggtctgcat cgtttacttt tccgtttacg ctgacagttc  78960
cgtaagactt gaccataagg gcaaacggca gagtgtcatt tgccatggct gctacagctg  79020
atacacctac ctgagcatct gcattgatat tgcggaattc ctgcagacga tgtttaagat  79080
ttgccgctgc ctgttgtacg ccatgctggt tatctacagc actgtcaaac aaatcccagt  79140
catctttaac atcatcagct ttatttgata catcatcagg atcagcaact tgtgccccaa  79200
cagacggcag aagaaggctg aaatcatcat tgctgttgtg ctttgtcagt aaagctgggt  79260
ttgccagagg tgccacacca taatgggaag atgctacccc ggtgccaccc attgcatcgt  79320
tacgcgcttc aaaatatgac gtcgctgctg cagcgttaaa ggaaaataat acagcagatg  79380
caatgatggt gcgggtaata tgatttttct tcatcattta atttcctgtt tatcagaatt  79440
tagacaaaac aacgctatga cacggatgtg ccgtaatttt tactttggta ctatctggta  79500
tttaccaggg taataaagac gtattaaata agctaacagg tagtatttgc cctgtaataa  79560
ggttcccggc aaggccaggt ctcaacgtga cgcgtcgcaa agacattgtt gtattctgcc  79620
tggttgtata ttcagttaac cattttcttt tttcatcgtt cagaagtgtt ggtgataatg  79680
atagtgccgg atatattaca gagccattta tttctttttt ctgtctcaat attaccccgt  79740
aatattctct tttcgtgttt cctgcgaagg ggaaactatg ccagaaaata acttcagtgt  79800
tgctgctatc attaataagc attctgaaat tatcagcagt atctggccat tcaccggaca  79860
acgctatcgg atagttttca tggccattca gccagtccgg attgagatta aaacattcag  79920
caagatgttc gagagcgtca gctgaaagat agtctgcaag tctggccggg tcctgtataa  79980
ccgtggagcg gatattccat ggcgacagca atgttgccag taatggcgca tttatatcat  80040
gcgacagcat gatgtattca attctgctta ttatgtttcc tgtggtgtta tccgcaggca  80100
taaacatatt atgaagagca tcctcaagca ggattcgggt taaatcagcg gtggatatgg  80160
ctaattgttc gctcattatc cccagaactt ctcttacccc ttgtgggtaa cggacctgca  80220
gtggtgtcgg gtttatctga cgaccgttga tgagtttttc gccgattgct tttttgtcca  80280
gcgagagcat cattcgggcc gcaataccgg tcgtattcag tctcattgtt cctccgactg  80340
aaaaagtctt ttcagctcat gtggttattg tatcttcggt gttttttctg gtgaaacgaa  80400
taatttcgat catgcagatc gaatgtgttt ggcgagttgt tgcaactcgc ctttctgtat  80460
gtgttttgaa tgatgtttac agcggggtgc tgcccgggtt cagagggcaa atcataatgt  80520
agtcagggtc gttaacaggt aacgctccgg gagatgggac acgttcgcct ttctgtgctg  80580
caatggccag tgtacgcaac aaaacctcac tggcgcggtg aactgcttcc tctttcgttg  80640
tggcagtgac gtgaaggtta tcaaaatcac cgatctcaat acgatgcgct ttctgcccat  80700
tttcttcatc gatggtcgtg atatgggcag gatacggcac aaaccatgct gccacttttt  80760
gtgtctgccg ccggcgggca tcaagtttac tgaccagttg ccatgcacga agatgagtat  80820
accgtttcag catattcatg gaacgatgtc ctgatattgc agcaatctcc attacattca  80880
ggctacccag ttcgaagaag cggcttattg cttcatgccg tagatcgtga aaatgcaggt  80940
```

```
cctcgatgcg aagtcgttgt gtggctattc tccaggcatt tttaaagccg gatgcggtgt  81000
aatcaaaaac attgccgtgg agattaacgg gcatcatctg aagaaagtta cgggcacgtc  81060
tggacagagg aacatcccgt gagtgaccgt ttttggtttc aggtaaatga gccacaccgt  81120
ggcgcaaatc aatgtgctcc caacgtaagg ccagtatttc gccctgccgc atggctgtct  81180
caagggcaag atggaaaatg acatacaaca tcagattttt ttcgcggaaa tagcgagaaa  81240
ggcgacgttc ttctgaagac gttagccggc gatctcgtcc ggaggatact ttcggcttgc  81300
gaaccagttc aaccgggtta gtacgacagg ttccccattc aacacgagca atattgaaca  81360
gagatgacag aagggcgagt tcaagacgta cagtattacc tgtaatgggt ttacccgttc  81420
gggggttgat ttctgctaaa cgaacgtctc tgtatgtagc aatatcaacg gttgttattt  81480
cgtccatatt ccgaagggca atgggatatc gcttgataac attgctccgg taaaactcct  81540
gttgatgccc tttcttgtgt acagaaactg ttttcaggta cttatccagt gcgcgtgaca  81600
gggacatttt acggatgcgt ggagacggca tgctaacctc aaaagaggca aaaaataatg  81660
ccaacaatca ttctctgcaa gcgtgccaat ccggtacctg gcgtaaaagc aattctggta  81720
gtacggtgat aactggtcgt atagcaaatg gtcagcaaat accgctgcca acaggatttt  81780
ctgccagtca gtgctcatgg agtgtgagca atgcagaaaa ccctcaaggt tggaagccga  81840
attactttgc gggatcagtt gcaacttatg atgcaaatcg aattgttaaa tgtggttttt  81900
atgatgaata caatttccat aaagggacat ttagagctga tttaaccgga aaatgtagtt  81960
atgtcgtcgc gtgtcagaac tgagattaaa ttgctggcgc tgctggccta cgtgccaatc  82020
cggtacctgg ggcgctccta aaattcaatt cacaacgcag acctacaaca tagctaaaaa  82080
cactcgtaat ttaaggctcg gggtccatgc atattgctca tggacttacc tgaatggctc  82140
accctttggt ggttttcaac aggtatattc cgaccaaaac aacgtttggt atgagagtaa  82200
ttatgcttgg ggaaattatg agtctggtgg gaccatatca gtcacatgcc tcaatcttcc  82260
tggtgctgga gtttaattaa aggggcaaca gtaggcatcg acatgttcct catcaacacc  82320
atcaccaata ccgtacatgc gtgttccagt cataatgtat ccagtcggac attgaatcgg  82380
cttgtaatag atcgaaccac cactcttacc gccgataaag tgattcattg ctacggatga  82440
tttgtaccaa ttacatgctg agtaattaat tttattaccc cctgaccacc gaccggattg  82500
gcacgtaggc cagtgccaat cccggtacgt gggggacaat aggtggaaaa ctcaaagtta  82560
ctcagctttc caccacaggt tatctggggc aattcgactt ctgtgccatt gccagaatgg  82620
gcaacgcaga ggatgcccac tactgccagg tagttgagag cccagcaggt tcacgtaaat  82680
ggtacaaata cgagcataag acaggttgta ttgcgtcgtg tgtaacgctc aattaagttt  82740
gatatccaaa tactgaaaat accccggcac cacatgatgt attttctgtt ggataggatg  82800
ttatctgata ggaagtacct gcaggtacag caaagctgat aaaggctgtt tttccatatg  82860
cagggttatt gctggcattc acgctaatta gcgtcccacc aacatatccc tgcagtcggg  82920
atgtatttgc acatgcacct ccggcagatc ctccattacc tccagatgca taaataaaca  82980
atgtactgcc ccctgaattc cgccctgaga atgaacctct atgtgaacct aagtttgtgt  83040
aagaaccatt gagcgaacca gaagtcttcc aggtaccgga ttggcacgaa agtattgccc  83100
ctgtattatc gcggcctaca aggccgttag gcgaacatga tgcgccagca acggcagttc  83160
tttccagttg taagtattca ccagtataaa ggcgaccatc agcccgaaca gaaccgcctt  83220
tcacctgacc gccggtatag atgcccttgt tgtttacact tcgaacccat gatccatcgg  83280
```

```
acatataaaa tccgccaccg tgagtttcat tgagccagcc tttgctgtta cgagtaatta  83340
accaaccatt attacttctg atatcaccgc cagcggtgac atttacgtca aagtttccgc  83400
tattgccttt tacctgaccg ctgaaagtgc catttacacc attcacattg ccgctgaaat  83460
taccagtctg ggcatttact gccccaacgt tattcaggtt atttgatccc atatcaatgg  83520
ctgtgtgcat tttgtttaag tcagggcgac cattgacctg gaatctgtaa agacgatcag  83580
tgtcctcagc tgcaccacta agttcatctg tcgataacaa tacggcaata tgcccgttac  83640
cgcttttggc accataatta cttaaagcta ctgaccagga acgtaatgca cctgtggctg  83700
ttttgccgtc ctggatatat ccaccaagac cagtggtaat atccttagcc atctggataa  83760
gtgctttcac tggataaggc gtgccaccac tggatacaac cattgcctgt agtaattccg  83820
ggttttgggc gtttcgaacc acatatgcct gtaaccgctg cccctcgctg tttgtctcag  83880
taaacccgct ggacaaaaag ccggtatttt tcagcatggt tgtcgtgatg acggcaggag  83940
ttgttgtggt actactgccc tggagagtcg tatagttttt ccctatgtaa gagcgggccg  84000
cactggtcca gttgctgaca agacgtgctt cagtttgcca ccctttttgtt tgaatatagt  84060
cctgccatat gcccgctccc caggcaatca ggagcataac aatcaataaa gccgcgccag  84120
tttccagcga tgcccagcct cggtcatatt ttttcatcag attacccata gtggttgata  84180
aagattatcc agcagcaaaa ggacatggcc aaaacatagc catggaccca gagggccttc  84240
tttatgccct tttatgcacc atgttgaatg ccataagaca aatcctcctg tgcccagcaa  84300
cacacaccat atggcgttat ataaccctga ccatgcggta atacccgcaa taagccacag  84360
gtctccagtg ccaatattaa gacgatggcg gttaactaat ttatgaagac agaataagac  84420
aattgcagca gtggcaaatt ctgttgtacg gaaccaccat atatcagtcg tgatttgcga  84480
tagcattcct gcaattaaaa aacgctgtgt gaatgttcct ggtaataaac ctgtcagtgc  84540
atccgttacc gccatttgca gtatgaacga aagaataagg acagcatgaa tacggtagag  84600
cagtggtgat gatgataaaa taattaacgc cacagctata ctgtatagcc atattcctga  84660
cagaacagca gggtgtgtct tataccagag atgtcccgta tcagataaaa aatgacgaac  84720
tctgaatagc agagttcgtc caataatgga aaatgtgaac atcaatggca gtatataaac  84780
aggggataga cttatgccta cgattgtctg cattgcctgc ctccctgtcc gggaagacat  84840
atccctttca tgtcacgata aattctccat attttattgg catattgctc tcttgtttca  84900
tgtctgtcct tacggaatcc ggcattgtat gacccaaggc aattccagct gacgccacat  84960
atctgaaaat gtcttgccag tatccagctt cctatatgga tattaaggca tggtttggta  85020
attaaatcct cagacttttt tattacgccc atatttacca gctttggaat atgggttgag  85080
tttatttgca tcaacccata atccgtgcta ctggctttac ctgttttttt gtccttattt  85140
atattaattg cgcccggcct caacgaagat tccccggcag aaatagcctt caataataat  85200
ggttcaattt gatagcgcgc gccggcagcg gcaaagcaat tgtcccactt gttggtccag  85260
atctgtttgg gagctacgta tgaagctcgg gcgggtggaa taagagaaaa aagcaggatt  85320
aatgaaataa gtctgagggg tactgtaccc cctgacatta aaactcctta accattgatg  85380
gtgaagataa gtttgtttgt accagtgctg ccattatctg ccttgcattg cgtactggct  85440
tcttcagtag tgacttttcc atcactgtga gcagtactgt tcagggtaat gccgttagtt  85500
aaaccagttt tactgattcg tgtggcaatc tggatacagg catcctgtgg gactttatca  85560
taggtaacgg taaaaccgtt gttgaaccct gatgttgaag ccggggcaac agttacagca  85620
ccgccccatg cgttatagag cgttgctgta ccagatgttt tgtcgccctg tacggtcatc  85680
```

```
ccagagggaa tgacacccat ctgaatgagg gcacctgtca ttttggcact gctggtaaat  85740
gtatatccat cgctaccttt tagcaggctc tgggcacttg tgataattgt ttgtatattt  85800
gcggtttcag ttgccacatt ggctcttgta cgcaacgcat acaaactacc cagaacaacg  85860
actataacaa aaagaacaac gagcgctatt gttccctgct ccaaaattgc ccatccttta  85920
tcatgaggct cattcttctt attatttcca gttaaagtgg tattaatatt ttctactaac  85980
ataaatatcc tcgttttgtt taaaagttac ccatgctgtt gtcactaata gactgaatat  86040
ccataatggc aaaaaccagt aacatgagag acatgacaag aaatatcagc ataattaaac  86100
gaatcacgtt tgcccgtttc tttacacgtt gaagtgtttg actaagccat cgttgaccat  86160
aattgctgat tagctctgtt gcgccatctc cctgtaataa agacaggaag ttggctgctt  86220
ccctggatgg gaactgataa ccgcactgac gcaaagccag tccaagatga tccccctggc  86280
ggacgcggta aataatgctg tcaagacgtg tgcttaacca tggtgatgca aactcctgaa  86340
gaatgtttag cgagttgagc gtcgtcattt tggctttcag aagtgcagcc atattcagga  86400
gaaatgttgc tccctgtata tcctgataaa tactccatgg cattatcttg tcggcaaaag  86460
tacgaacact gtcagggctt ttccagtttg gcagagacca tgatattaaa cctgtgatca  86520
ctgcaaaaag aacggcacat atagcgccgt aattatcgac aaaaacagat aatccataaa  86580
gaaaaccaag agcaccactc catgaatcgg gggagcttat tttgctcagt tcaggtatta  86640
gctctgtatt cagaacatat aatgtccccg tcatcatgat taacaatccc accggataaa  86700
tagccatttg ccatatagcc tgatggattt gttcttttgc atctgtaaga gtggtggcga  86760
attgcagtgc atccacaatt gaaccacttc ttatcccggc gctgattact gcggcctctt  86820
cctgaggaac ccataaacta agagtatatt ccagagagtt ttcgccactg ttttcacgaa  86880
gagactcaat gcagtctgtg gccagttcag caaagggatg ccattttcgt ccaaagtctg  86940
tccaggcatc ccgcatctgt tccagtgcgg tctttaatgg ctgtttattt tccagcagaa  87000
aacgcagggc ttcgtaaaac tgcaccctgt agggggcgct gaacgttttt ctgacaatga  87060
aacgcctcag ccgttgactg aaattcattt cacgcatgtt gttctcctgt tagacatcat  87120
cgatgctgag gcgctcgtct tcgtccagag ggatgattct gtcggcttca agagggtcta  87180
ccagaccttc attgatacgg cgaagaagat gctctacacg actgatgcct ttcatgtttt  87240
ccagccagta tttacgtgct gcaactttgc cgcgtgtttt cagaatctga aataagcggt  87300
tatcaggttc tatcacctca gcaattacag tcctgccggt gaggccttta cctatttcac  87360
cgcgctttct gccgttaatg attacgtcgt gattacattc agagcatccg tgatgatttc  87420
ggaaccagat attatctgta ctgcagagtg aatctttatt gcagtgccgc tcaaggtaat  87480
cacgctcgtc gtcgctaagt tcaggtgctc gcttttccca tggaatacgg caggagggac  87540
acagagttgg tacaaggcgc tggctgatca tcccaatcag taattgcgca tcgcaaataa  87600
gatcggcatt catacccatc gtaatcattc gctccggtat acccagagct gagtttgtat  87660
gtaatgtcgt cagaactatg tgcccggtct gtgccgcgta ggtggttgac atcatcgaga  87720
taagatcgcg catttcccct tccatgatgg catcagggtc aagtcgcatt gccgatgaaa  87780
tagcccgact ccatgccagt ttgacggcat cttcgtcgga tttgtcgcag ataatcggag  87840
tctgtgttgc tcccagtatc tgtccttcca gcggatcttc gattgttagc aggtgtcgcc  87900
cctgattatc gtcaagatat acacggcagg cgctgcgtaa cgttgtcgat ttaccggaac  87960
cggttggacc tgacaggact atttttcctt ccgggcggcg cagcattatg ttcagcaacc  88020
```

```
ggatttgttc cgggataaag cccagttgtt taaacgtggg aactttatct ccgtcatcgg  88080
gtatcaggcg cataactgca atcagaccgt ctcccgtagg tctgtgactg tagcgtgcac  88140
caaatattcc tatttttcgc attaattgtg ggacaggcg cgcatcctgc tccctttgag  88200
ggaagaaact ggtttcagtg acatcagcca ttgacagaat ggctgttgcg caaagtgaat  88260
agcccagtgc tggttgatct tcatctacag tctgcagttc accgaatatt ctcatgcgaa  88320
ctttgaaaat agactctgaa attaagaaat gaatatctga agcaccaagt tttctggcag  88380
tttcaaaata agatagaact ttcttctcac tttcactgac atcagcaagg tctttcagat  88440
gaataattcg ttctttcggg cctctgtttt tctcatcctg acctgcctcc tgtaactccg  88500
acaacgagac tacttttggg ttgatatccg gatataattt tagcagctcc tggagattac  88560
tttgtacgtc aggccttgtc cgctggtttg tttctataag aatttcatgg gtgtctcccc  88620
tggatataaa aaggagagca tccttcagat tatatttatc catatcacgt tactcagaaa  88680
gtaagggtgg tgccatcact taacgtgacg ccagacaatg agatcgactt cactgtgacg  88740
gatgtgcctg gaagctggct gccagtggtg acgcttgtct gacgtccatc agccatgcga  88800
agaacggcat taagacgttt atctttgccg tttatttcca taatgatggg caattccttt  88860
ctgtttttag atgtcggctg ctctgaaact gatggcaaag aggcagtcac accagagaaa  88920
cctgaaacag tttcagatga tgaagtaaca tctgattctt cgagttgttt ctgtagctgt  88980
gcgccctgaa cttttgcctg taaaagaata ttccggtttt gttgtgcttc aagttctcct  89040
attgtgacaa gaggttgtgt tgttgcaaat gaaaaaccgg agaagaaaaa tatggatgga  89100
ataatgagta atttacctgg acgcataaat atgaccttct gaggaataac tgaaagtacc  89160
gccgtttaat tcaaaatgga tattgctcag acgaacgccg gtatcctgaa ataaagggaa  89220
caactcatca ggatttacag gcgttgataa actgaactga tattctttcc atttctgaac  89280
aggggctggt tcaccatcgt tacctggtaa tggttccggt atggctattt cattaatggc  89340
cggcgttaac tgttttttct gaaaccacgt gaacacccgc atcagttgtt ctgagggggt  89400
agggactgcc tcatccctgc ggggcaggga aggcagtggc cgggttacag aagccaggcg  89460
tgcaccatct ttaaggttaa agtcaggaat aacattaaag atttctttgc ttcttgccag  89520
aaagccttca atagttcctc ctggctgtcg ttcgtaaatc agtgtgaatg tctcgggagt  89580
acatgttcca ccggtaagtt tccagccttc tagcgcgacc ggtgatggtt ttcgaaggtc  89640
cgcgcaggct ttcagaaaat cactgattac aggttgtgat gcccatggat gcgggagttc  89700
tggcggtgga tcgggctttt taaactgcaa tcttgcccgt gcagctatct cctcgggcgt  89760
cggtacgaca tccggctctg gctgagtcat ccagaataca gtgcctgcgc cggctgctac  89820
taaaaacagt acggcaggca gtgtgaattt gctgcgattg ccgacagtaa gtttgcaacg  89880
gcggagatct gctgatgata accgggtaat aatactttcc cagttatcag gatgttccag  89940
aggagatacg acctgccatt tttcgggggg ctcttcgttc atcgtcagaa aaagactgac  90000
cttttgagca acatcagcat catttcctga cagatcagcc ataacggcag gctggccatt  90060
aatggaggca aggaataaaa gctccttatc gctgtaccgg aagacgccgt atccatttct  90120
cacccatgag cagaaagcca gagcaaggga aaaataatga ttgcgctccg gcctggccag  90180
tattcctgtg ccggtaatgc ggctgatctt cccacgggaa cttctgctgc ctacagtcac  90240
tttcagagag gtaagccgtc tggattttac atggggcttg tgtttctgat gagaagggac  90300
tcgctgtttt tttacgacag gactccattt aagacaggct gcccacacgc gatgatttac  90360
tttaggatct gcgagaagca caaccgggtt gatatcttca tcagccattg ttgcctcctg  90420
```

```
acgggaaagt cggggtaatg atgattacaa gcgtgctgcg ttcatttttc ccggtttgtg  90480
aaccaccaaa taatggattt gctggcgtaa acgtaccggc tttacttgtc gtcgtattgt  90540
tctgatcgaa accagtaacg acaagtgatt gcccttcttt cagattgacc ttctggctca  90600
gtgaacgcag tttggtatac ggcatttcga tgtaactgtt tccgtctttt gacgtaaagc  90660
tacggattgt tgggggatct gacagattaa aattcatctg caactggaga ttgcccgttt  90720
tctgaattaa aggcagcagg gtcatattga atccggtggt gatcatgccc ggcgttaatg  90780
ttgttgttgc tcctacatcc gtagtcgttg ttgttgctga ctgggcgacg taaaccgtct  90840
gatctgccat ctggataggt accggcgtca ggtttgtgac agtgctttct tgtgaagtca  90900
caacactgac atcgccctgt tcactcagcg ctttaatcag aagactggaa ccgctgaatt  90960
tggcggcatt ccctgttgcc gtatccagaa ttgatacgcc tgcagatgta gcgcctgtaa  91020
aatctccgct tgcattgttc aacgttgctc cggcggaatg tagcgattta taaacaaggt  91080
tccagtccag accgaactgt tcgtttctgg tattgctgac gctcagaacc tgtacgttca  91140
gggctacctg gcggttcata atactgtttt gttcgtccac atatcgtgcg acggcttcct  91200
ggacagctgg agtatcagtg acagtcagcg ttgagctcga tgcagataac cagtaacggc  91260
ctttttctgg tgtcagcatt gcttcaatag ttttccggat gtcttcatac agatcgtatt  91320
cctgaccaac ggttgtgctc tgagaggacg ttgcatcacc ggatgctgag ttatcctggc  91380
ctcctgttgc ccccattgtg cttgttgagc cagagctgac actggaactg ctgctggttt  91440
tggtgttcag catatgaagt ggatacgttc tggtttcagt cagatagaat acaatccgac  91500
cattatccat gcgccagtac agaccactcc ggctggccat cagatccaaa agaccattga  91560
tatctccctg ccacatgagg ttattcagcg ttaatggctg agtggaggta gtcattgttg  91620
tgctgcccag gctgcttaac ggtagacgcc cattttcatc tggtgctggt agtgttcctg  91680
tcatctggcg ggtagcgcct ccttcaagag ttgaattggc tgcgtcaggc gtgatgatca  91740
cagggatgcc gcatacggca gtaatacgtt gccccagttc ctgcagagtg atctctcctt  91800
ttcttgcctg cgtgatgtag caggccggag ctgtttgttt tttctctctt gatacctgag  91860
cgaccggaac agggtttatc cattgattat cgagccaggt aagagcctgc gatttacggg  91920
ccgaaagggc tgataccttt tcccgtgcat gtgctgagtc ttcctgtgct tttttctgca  91980
ttttgttgat ttcgctgaaa gtacatccgg agatggaaag agcgacggcg atcatgcagg  92040
ggagcaccgc cagcttcatt gaacgctggt gtgatttttt catgaatata tccagattag  92100
ttaacgtaga cgacagaacc agcagtaatg cctgccgggg gtgtcagacc ggttgcagtt  92160
cctgatagcc aggtgagttg cccgttttgg aagatcccta ttagtgcaga accacgactt  92220
tttgaacgca aagtttcaac aagacctggt tgttcaggca tccataccca cagacgcccc  92280
tgttgtaact gatgtttaat tcgggagtcc ggagtgacag ggagagccag tttatctgag  92340
gaaattactc cgtcctgctg gcctgatacg tatctgatat cattgattct gttagcaatc  92400
attagtatct gacttgccca tacagacgca cttgcatatt gctgggcgtt tgtggtttca  92460
gacatcttct gattctggta gctaccagtg ataatcagaa tggtcaggcc gacggccatg  92520
accagccatc ccattagcga ccatctcttg tatcagaaac tgtaatgatg cactgcatgc  92580
gagaagcctg tgcgtataaa ggtttttgcg cagtccgata taactcaaat acctgctcca  92640
tggttgattc aaatgatccc cggaacatta aaggcgcatc cagacggtaa tcggttacag  92700
aaagtggcca tatgaccatc cagtgcgttg atgccatgct ttcgcatttt gtttcttctg  92760
```

```
cccacttgat aatgttctct cttaatgtgg tgcctgccgg cgcacgccac tctttaccct  92820
gagataccgg tttaacaggc gttccggtca tgagcgggat cgacttgact gtggagccgg  92880
ttggagtcgg ggtggcggcg ggcgttgacg aagatacgct gtttcccctg aatggatttc  92940
gtggtttgtt ttggctattt gctgtcgttg gagattcagg gtaagtggat gtggttacca  93000
tggctgctgg cgagatagtg gttgccgtgt cctgtgccgg tgcagcagct gatgttgtga  93060
cggtcaacgt tttattattc cagtccagat ggccccagag gtgttgttct tccagcaacc  93120
ggttcagaga acgggtccac tgatcattgg cagaccatga aaccagtttg gtattcagct  93180
tgggcgtggc tgcattctct tgtctgaatt tccatccttc cggtagtaat gtttttatcc  93240
actgactgac ggtccggtta cgggccgtcg gcgatagtgt tacaggggcg ctaccaggct  93300
tgcctgtaat gattaaccgg gagaaattct gacttattgt tggtgaaggt aacggtcggg  93360
attcgctaac aggctgtgct gtttttactg tctctggcac gctgactctc gggggggggag  93420
ttattttagg tggagaaaga cgttgttgcg taagtgccag aacgccagca ctttcactga  93480
tttgtccgtc aacaaaaacc agagcaggcg tatctgatgg tgccacgtta ttgctgccgg  93540
aaattccggc acagccggac aataatgacg gcagtataag tgtcagacag tttttttttca  93600
taacggagac tccgtgttcg tatatacgtg tttgttaatt ggtgtgaggc ggctggagag  93660
gacgaatgac gactgtcatt ccgtccgaat gcaaatgcgg gagagaccac tgaaataaga  93720
gatatacaaa aggaattgat aatttttcat acagacttgt tttccgtggg catgtaataa  93780
cagagaaatt caaaccataa gattccagtc tctttataag tttatttatt cttgcaggag  93840
taaagagatg tgaatgcata acaatggttt catcattatt aattgctttt gatatcagaa  93900
aaagtaacac atcccagtgt ttcctcattg actccgggca acgtgtatcg gcataggggc  93960
taagatgtat gcttgattct ttactgccat tttttttcgc aaagaatgtg aagttgtatt  94020
tagatacaga ccttacgata agaagcacgc atctgaaaag tagtggggaa aagcaaataa  94080
taaccactat acagaaatat aatatataag atagtgatat gtggtcagtg tatagataac  94140
ggaagtattg ccacggggta gtgatgtaca ggcaaaacgt acaccaaagt aaccatagat  94200
ataatggtac gttattattt ttcatgttag ttgatgccgg cgactaagat aacagagtaa  94260
gggggattaa ctgtttaatt ctttggaacg aaaaaatgca gttcctgaac atcacacacc  94320
attatttcca caggcttacc atttttatcc agtaaattg aattggtttc aaaagatttg  94380
cagttgtttt tacttttaaa tgaatcaagg tacagggtgt taatgtcaga ttcgtcatct  94440
gttgtttctc ttgaaataat actgttttct atcaccacat tttcatgtac ctcatttggc  94500
attttgtact gttgcaaata ttgttggcgg cggatgcgtg cctgttcact gctttctatg  94560
aacaccaccg tgatgattgc ccagtacatg ataatcagga aaacccagaa atcttttggt  94620
atcttccaaa aaagtgcgga cagtttgtta tctgatgaaa ttaaaatcgg aaaaaggatt  94680
gcaaagacaa tcaaaatcgc gatggttaat ttaaataaaa acgacatggt cccctcctgt  94740
tttgacgagg tcttttgttt ttgttgtttt tacgacagcc agtcctgcag gtgctgatgg  94800
cgggagcggc tacccttgcg ccagcggcag tggctaccgg gtgcacgttc caggcggaac  94860
agaaatcggt tgttgcatag taccaccaca aggcagttat ccggcgtgca gaagcgtcgg  94920
gcaagctcat cgggatctgt ctgtgttttc gttgaaaaca gcttgcgttt gcagtgcgtg  94980
tcgacgacca gtacctgtag tcgtccggga tgttgctgtg gcatcaaaga ctccttccgg  95040
aacggggaaa aaaagcagct gtaccgtcat aactgcaggt accggttgcg aaaaaaacgg  95100
cacaagcgag tggtgacaga aagaattccg gaaacggcag aaagggcggt acaggctgcg  95160
```

```
aagacgggaa acgggttgtg ttgggaatta acgcacgtga ggtgtgatga gaacgacgcg  95220
cttttcgcca gctccgtctc cggtgaatcc attcacgaca agggactgtt ccggtctgag  95280
agaaatgctt tgttcaacag tctgttttcg tttctggtct gtggtcgaga gtcgcagagt  95340
gatatttccg ggcgcaccgt gaatatccgg tgatacctgc attctgacac cgggagagac  95400
atctgcagtg aaggtatccg gacctacgga cgttaccagt gattcaacac agggcgtatt  95460
ctgtatcatc ccgtggagcg tttcaggtgt cagcgtcagg ctgtcattaa aaaatgcact  95520
gcgtgaaata ctcccctgag caccggcaaa caggtccgga tggcgctcat taagaaggct  95580
tccgtatttt tccgccaggc agattgggtt gctggccgtt gtgtctgttc gcacggtatc  95640
gaccgtgaat gtcacctgcg ggtgatgttc cctgtggcct gtgcagccgg acagcagtgc  95700
ggcggctatc gtcatccaga gtagtggttg ttttttcatg ctgttaattt cctctcaggg  95760
taaaaagaaa gactcgcacc gtcatgtcga tgggggccgc ttgcgaaaaa atggcacaag  95820
cgagtagtga cagaaagaat gtcggaaacg gcaggaaggg cggtacaggc tgcgaagact  95880
ggaaacgggg tatgccgggg attacacatc ctcagtgtaa tgtgatagtc gtctgctcct  95940
gtgttgcacc ccagacatct tctggcaggc tgggcagccc gataaatagg gtgtgaaaga  96000
gggtttctct gcgttcgatc ccgaattgat gttcgtatcc tctcaccacc tgaaatcctt  96060
cgtcggagaa tattaactct gccgtttcca gaagctgcat agttttgcgg tgtagtggag  96120
tgatcagctg caacgtaact ggtgccctca tatcgcctgt cggtagaaaa cactcttcgg  96180
tgcgacttag ttgtagcaga tgacgtttcc cggaacaggc ccgttcaatg gattcattga  96240
acaccctctc aggccatggg cagacatatg tgcgccagcc tgctttctgt aatttaccca  96300
gtgcagcccg aaaacgaaac aacggacatt ccccgacagt ggcagagctg agaaagagcg  96360
tattcagcgt tccgatgatg ggaatattgc gatctttttc ggtcaatgct tttaacgcca  96420
tgatttcgcc agggagacta cggaactcag gatgtctgct ggcaccagaa agccattcaa  96480
gcaggtaatg ccgtaatccg gtttcactgg ttatattgtg gttttcctgt gccgttttca  96540
gggcattcag tgcacaccag agcaactggc gcacgggatg ttctgtcgtg gtcatgcgaa  96600
tgtcctactg tgagatgaaa agaagaccgg tatccgctct ctccgccaca cgtgatggca  96660
cgggccggcc tttgataaaa cgaatcaata ctctggggtg aagcctttta tttctttcgc  96720
cattaagaaa tacacgattc catcaaaaga cagggggagt ccatggtggg gatggcttcg  96780
tgcaggcttc actccagaat attctctgaa ttgaaaaaag cccggcccga aggccgggaa  96840
atactggcta tgggatgttt acaaggcgct ccataaagcc gtgatgttcg gcatttgata  96900
ccagttccag gagcagggat atcctcgact caggctggag agtattttcc attctgagga  96960
gatactgata ttgtgctttt gtcagccata tgctggaagc cgcattcagc tcttccctgg  97020
ctcccggatt tagcacaggg tccgggtaaa tcttcattaa tccatcaaca atatctttat  97080
tgacgggttt tatttcaccg ccaaacttca cgaaatcaat gaaggcgcta tggcgacgta  97140
atgccgatac tggttgaatg tcaaaattag ccagaataaa aaagtaccct ggaaaaatag  97200
cgaatattct ttcacggtaa cagcgcctgg agtctgcccg tcttatcttt cttgttatta  97260
atggagtcca tggtacgacg ttttgctcat tcagccatga gaataaagat tctctgtttt  97320
tgccggctgt attatattgc gcaagatacc agttccggtt attcaggtgt tctatattca  97380
cgaagttcaa cgctccgcgc aaaaccgatc catgatggac gattttgcga tgtcaggcga  97440
atatgctaaa tcatatgtct gaagcagtgt ccagcccata tctggataaa ctgcagttct  97500
```

```
gacaggcata taaccagcag actctagtac gttctgtatc ggtgatttgg cgaactcaca  97560
gataaagaac ggctaagcac taatatcagc aatacagtgg cacagtattg tgatacgcga  97620
aataaaacat cagcacgtca gttcagagta agatcgccat atatcgggca tgagccagat  97680
acaaataact gggacaccgt ctgaagtgat ttgctttatt aaagtaactt gtgcttggtg  97740
tttatgttta tcaatttggg atcgcctgta aagtgcaaaa tgcaatttcc atgaaagtgt  97800
ccccttttaat ggggacacct gttcacattt tttcgttttc tttagctgta ttgctaatca  97860
tgaaaacgaa agttcgcatc agcacagcag agcgaagtgc atcatatcct tccagattta  97920
aattcttcag gcttcgcttc aggtaggttc gtaccgtttc gggagaaagc cgacagttct  97980
gagcaatggc gtcgtaagga acacccattg cgtaaaaaac gcagacttta agctggtttg  98040
ttgatagctc gggaaacatg ccttccaaca gagtgatggc cgggagtttc tgtatcagtt  98100
gaggtgacat agcaaaggtc tccgatgaca actaaaaacg ctatcaccga gttcctacgc  98160
tcattggtga tagcccagac gggggtagga ataccggcgt catcggaaac cggccaggct  98220
aatgcctgcc ccgcctgagc taccatagat gacgacaaga aatacaagtt cctgtcttta  98280
tggtatggca aaaaacgacg ccaaatgaag aaattaactt ctgcgccgac gatgactacg  98340
cgggttccta cgcccgatca cagttttgcc tgtgaccagt aaagggtact tagtataacg  98400
caccgagtca actaacagct taaaaaacat acaaaaaagc gtcaaaactt aacgctccgc  98460
gccgaagcga tccaggcatg atgcttctgc tttgtggcgt tcgaacatgc tggtccatat  98520
gcacgaaacg gtgtctgacc ctcgcccaga caatccgcag ttctgacgaa catatgaaca  98580
aatatgctct tgtagaggct gttgttacac aattggcggg ttgtgtaaca aatggtttta  98640
tcttctaaga attattctat ttacgatcga atgatctaca aaatgatttt ttaaaggttt  98700
tttagatcgt ttaattacat taaaacagaa tattattctg ttaggtggat cggttgtaag  98760
ataaatgatc gtgagtagga caaaagtcga tcttttaatc caaaagaag              98809
```

<210> SEQ ID NO 34
<211> LENGTH: 4773
<212> TYPE: DNA
<213> ORGANISM: Escherichia coli

<400> SEQUENCE: 34

```
tcacctcctg ttggggtgat tatttatatt atgagttctg gcaggtcgat atgttatttc     60
cgaaaagtga ccatctctca gatacagaac tctgtctgcg gatgctattg tttctggtcg    120
atgagctatt aacagaacag gaattccgag ttggcgtaat gtctggctta tttctatttc    180
actttccaca tcaagatgac tggttgcttc gtccagtaat aatagaccgg gtttttttata    240
cagtgctctt gccagtagaa tacgttgctt ctgaccacct gaaagtcccc ctccggtttc    300
tccaagtaat gtttgatagc ccattggcat tgccataata tcactgtcta taagtgccag    360
acttgcgcat ttacgcatgt gttcatgatc tctaatttcg ctaaaaaaca ttatattatc    420
agctatagaa cctttgaaaa gatagtcatc ttgcaataca gtgccaattc gttgacgaac    480
ctgaaaataa tcagaatgtg tatgtggtat gccaaatgca ttaattcttc cttcacttgg    540
tgtatgaatt ccaagaataa gctttaccaa tgttgatttg ccacatcctg atttacctgt    600
tattgctaat atttctccag gaaagagcat tagtgacgcg ttatccaata tgggtttatc    660
tgcgccctta tggctaaatg ttattttttc gataagtaat ggtggatggg tattatcata    720
tttatgttct ctgtactggc ttgcagatat tgtttcatta tggtttgccc aatggtgctg    780
attctggtga ccttcctgtg gtgttagcac aatatcggca agtctctcgt tataaacatc    840
```

```
aagcatgcgc caggaaaaaa agttatcagt cagattgctt atactggatg aaaaacgcat    900
ctgataggat aagtaagcaa ccaacatacc cacggtaaat gtcccatcca gcacttctac    960
tgctccctgc cacaaaataa tggctgaaac tacactttcc gtcagtgtat gcgtcagttc   1020
atagctcatt tgtaaacgat tctggcgtag ctgtgtgttt ctgcgggtaa cgttgaggtt   1080
cagccaggcc gcttctctgt gaatagttac accgttgatt ctcagactct gaatgccgtt   1140
aagggtttcg agaaaatgcc ccgactcctt agttcctgca tcccagacat cttcaacaga   1200
ttgccgtaaa gccggatacc acaatgctct cagtgcgcca tatataatag ctgcaattac   1260
tgcgattaat gtcattcctg ggctatacaa cagcatcatg caaagagcag tcacaataag   1320
tagcatatcc agaatgcctt caagaacctg cgttgtcagc gcctgctgga ttatatctac   1380
tgcttcaaaa cgggcattaa tacttccttt acttcgggca tcgaaccatg caagagggag   1440
tcttacaaga tgatggaaaa ctctggcagt ccattgcatg ttaaaattga cggataaact   1500
gatcgttgcc cattgtcgtg ctagggagag taataattgt atgagtgata acaacagtag   1560
tgccactata atgacataca atagacttct gtctgctgcg accagaactt catcaattac   1620
cagttgatta agaagtggac cacctaaagc cagaatctca agggccagag caaaaataat   1680
aatttttgtc attgatgcta aaagccccgg ggttttccct gtcagttgac gcaggtggat   1740
tttttttctc tcgttccggg gggtgaaatc actggctgga gttaattcca gtgccactcc   1800
tgtaaaatgc ttacctgcgt ccaacagact tattgtaatt tttcctctgt ccggatcatg   1860
gatgtataac cggtttcccc gaactttatg gagaacgacg aaatggttca tatcccagtg   1920
cagaatagat ggaagattaa gacacctcag atcttcgggt tccagacgaa ctgcacgtga   1980
tgataaatgg atggacgctg cacattcgat caacctttgt agcgtcattc cctgaatacc   2040
tatattgaaa cgttcccgta atgtcgataa atctgttttc agtccatgcc agcaggcaat   2100
catagccaga cacgccagac cgcattcagc tgattcggtt tgacggataa cgggtagttg   2160
tttccttact ttccagttta ttgattccat tacagatttc ctttcatgct ccataggggc   2220
tctgtcagcc attcccataa atgacgagta tcaaggttga cgtctccttc cagagtcatg   2280
cctggtctta gcggttcttt ttttccgtat gcaaatataa atgtattttc aggttcaaca   2340
ataacgcgat aatgcccttc gttttctttc catgtgacgg gtgaaactgg taataagtcg   2400
gaaggagcca gagtcgtatg actgatttta cgaattgtgc cgtactggat accaaatttc   2460
tgataaggga aggccgaaaa cttcagagat acccgttgac ctggtcggat aaaaccggct   2520
ttctggctgg tagcataaag ctcaatttgt aaatgagcat tatcgggaat gagagtcatg   2580
accggttcag atgctttcac agactgcccc tgtttgatca gtacagcagc aatagtcccg   2640
gatactggag ccctcagtgt aaatttttct tgtccggcga gttcatcctg ttgttgtttt   2700
agcacctgca attgtctgtc gagttctgct ttacggcttt tcccctgaac aataagatga   2760
tttagttcat ctttggctgt gtccattgca gtatgtaact ggagaagccc ctgacgctga   2820
tcttcaacgt tttgttgagc ggcagaaaca tcaatttgtt tctgttggaa ttcgatatct   2880
gacacataat gcgtaccagc caattttttta tagcgttcca tgacggatat agccagttct   2940
gcctgacgtt cagcaagctg aagtctttgt tctgcacttc ttatttgcgg ctcaagtgat   3000
atcatccttt gccgtatggc ttcctgttgt tgactattat ctcgcgactc aaaggattgc   3060
tgggaggcca acataatata ctgagtcttc agggaaatac tcatcgttgc taatgtgcca   3120
gttccgttac cgttataatg ttctccactt atatgataga gttgtgtccc tgcagttacg   3180
```

```
tgttctcctt cggatacagt cagttgtgtt acatatcctg catattgagg aattattttt   3240
accagtcctg atgagggcat gacgatacct gtaagatgcg ctttccttgt atagctaccg   3300
taatatatga atacagtcag acttaacata atgaataatg taactgttgc acatacggat   3360
aggctaaatg atgttggtaa aataatgtca ccatattcag tgtcattatg atgttctatt   3420
gcttcacttc tgaatatatt cattattttt aatacaataa gtaacctttc cgtcaacaag   3480
agggtttggt tgaataatat tgatatttga tatacatctg acctgtgtga tgttaaagtt   3540
ttatactata atatatttaa caatataaca aagccgttta ttcccgcatg taacagcatt   3600
ggatagaaaa tccccttact gcaaatcctt atattcaaca ataacattga cataataaac   3660
agaataattt gatcagccac attataatac tgcggatgca tcaggcagaa aaataaagat   3720
gtacacacgc agggggtaaa taattctttt ttataagtcg tacatagaag accgaataga   3780
catgttcggt aaacaatttc ttcataatac ggaactgtca ggaccagtat aaatatttca   3840
atccaattaa gtgaagttga ttcactattg ttcaaattgt ctctataagc aaaaataagc   3900
agttgcatga gagcaatcac agcaaatgat attactaata gctttaatgt tttcgcattt   3960
gtctttatgg tgattttaca acctggtatt cttcttaagt aaaaaatata aaatgaagtt   4020
gacattaaaa tttcagtaat aaagacaaag gaaaatgcca gatccaaacc aatatattgt   4080
atggtgaatg ccggtgtgaa tatcacaact gttgatataa caacaagtag aagaaacgct   4140
atcgcattat ctttactata tttatatatg ttatcattca taatgctatt tcgcggagat   4200
tgttcttatt ttttctatga tatagtccat gaatcttgcc gtggaaaaaa gagtgatcag   4260
catgactaca atctttgaaa actcggaagg tagtgaaaac cagtataaat caataacaga   4320
ggagccactc aatagtgcaa atcccagtaa caaaccacat ataaaggaaa gtaatttaat   4380
aaacatagta gcgccctcca ttatatctat ttatcggtta catgttccgc caacattatt   4440
acctgaacaa ctactggaac ttcctctgtt accacttcca tttccactac catgatctga   4500
gagacattga ccaacaacgg ctccaccaat ggtacctctt gccattccta tgggacctcc   4560
tttgatcgca ccaccaatca ttccactaaa tacagcgtta gcgcatttta cagtgcttgg   4620
atcactataa atatgagttg gtgcgtttcg acccagtgag ttacgagccc cactggaacg   4680
gtcattacgg gggccacctt caaagttgct gtttgcgttt cctccgctga caagcgttat   4740
ctcatctaaa gttaattctc ttatatttgc cat                                4773
```

<210> SEQ ID NO 35
<211> LENGTH: 102
<212> TYPE: PRT
<213> ORGANISM: Escherichia coli

<400> SEQUENCE: 35

```
Asn Ala Asn Ser Asn Phe Glu Gly Gly Pro Arg Asn Asp Arg Ser Ser
1               5                   10                  15

Gly Ala Arg Asn Ser Leu Gly Arg Asn Ala Pro Thr His Ile Tyr Ser
            20                  25                  30

Asp Pro Ser Thr Val Lys Cys Ala Asn Ala Val Phe Ser Gly Met Ile
        35                  40                  45

Gly Gly Ala Ile Lys Gly Gly Pro Ile Gly Met Ala Arg Gly Thr Ile
    50                  55                  60

Gly Gly Ala Val Val Gly Gln Cys Leu Ser Asp His Gly Ser Gly Asn
65                  70                  75                  80

Gly Ser Gly Asn Arg Gly Ser Ser Ser Ser Cys Ser Gly Asn Asn Val
                85                  90                  95
```

```
Gly Gly Thr Cys Asn Arg
            100


<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 36

tgctgcgatg gaaaaacgtc                                                   20


<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 37

ttctggacgc ttgcgatctt                                                   20


<210> SEQ ID NO 38
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 38

cttgcagacg tcttgcagtc ttaaggggac tggagc                                 36


<210> SEQ ID NO 39
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 39

gccttgcggc ctgccctaag gcaagccgcc agacgt                                 36


<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 40

atcgctgtag gtctgggtct                                                   20


<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 41

atgtcctgcc agcgttctac                                                   20


<210> SEQ ID NO 42
<211> LENGTH: 36
```

<212> TYPE: DNA
<213> ORGANISM: Artificial Sequence
<220> FEATURE:
<223> OTHER INFORMATION: Synthetic oligonucleotide primer

<400> SEQUENCE: 42
aatatcagaa cgttaactaa atagaggcat tgtgct 36

<210> SEQ ID NO 43
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 43
ctaccgtaat aaattcagac atcagcccct ccctcc 36

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 44
agcggcagga tgcattatca 20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 45
gggaagatta ctggctgcga 20

<210> SEQ ID NO 46
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 46
gtgaatattc acgggcttta tgtaatttac attgaa 36

<210> SEQ ID NO 47
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 47
aattaacacc tatgtattaa tcggagagag tagatc 36

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 48
caatggcaga tgaagcgagc 20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 49
tgcaaatggg ctggatagca 20

<210> SEQ ID NO 50
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 50
aactgcgcac tctatgcata ttgcagggaa atgatt 36

<210> SEQ ID NO 51
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 51
caggaaaaaa gcgctcccgc aggagcgctg aaggga 36

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 52
cgctatcagg gtaacgggag 20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 53
agcactttca cggtagcgaa 20

<210> SEQ ID NO 54
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 54
gttgtcagaa tcgatctggt tgatgatgta gtcaac 36

<210> SEQ ID NO 55
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 55
gtgatcgtcc ctgctctgtt agtagcaggt actgca 36

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 56
tgttgcgaac ctttgggagt 20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 57
agcaaggtga cgatgagcaa 20

<210> SEQ ID NO 58
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 58
gggcaaatga acttcgtggc gagaagcgca atcgcc 36

<210> SEQ ID NO 59
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 59
cttacaaatt gttgcgaacc tttgggagta caaaca 36

<210> SEQ ID NO 60
<211> LENGTH: 22
<212> TYPE: DNA
<213> ORGANISM: Artificial Sequence
<220> FEATURE:
<223> OTHER INFORMATION: Synthetic oligonucleotide primer site

<400> SEQUENCE: 60
tgtgtaggct ggagctgctt cg 22

<210> SEQ ID NO 61
<211> LENGTH: 19
<212> TYPE: DNA
<213> ORGANISM: Artificial Sequence
<220> FEATURE:
<223> OTHER INFORMATION: Synthetic oligonucleotide primer site

<400> SEQUENCE: 61
catatgaata tcctcctta 19